US012697448B2

(12) United States Patent
Chamtie et al.

(10) Patent No.: US 12,697,448 B2
(45) Date of Patent: Aug. 4, 2026

(54) ACOUSTIC MEASUREMENT SYSTEMS AND METHODS

(71) Applicant: ResMed Pty Ltd, Bella Vista (AU)

(72) Inventors: Hayat Chamtie, Sydney (AU); Liam Holley, Sydney (AU); Phillip Anthony Burns, Cremorne (AU)

(73) Assignee: ResMed Pty Ltd (AU)

( * ) Notice: Subject to any disclaimer, the term of this patent is extended or adjusted under 35 U.S.C. 154(b) by 550 days.

(21) Appl. No.: 18/312,871

(22) Filed: May 5, 2023

(65) Prior Publication Data

US 2023/0381435 A1 Nov. 30, 2023

Related U.S. Application Data

(63) Continuation of application No. 16/626,082, filed as application No. PCT/AU2018/050683 on Jul. 3, 2018, now Pat. No. 11,679,213.

(30) Foreign Application Priority Data

Jul. 4, 2017 (AU) ................................. 2017902594

(51) Int. Cl.
| | |
|---|---|
| *A61M 16/00* | (2006.01) |
| *A61M 16/06* | (2006.01) |
| A61M 16/16 | (2006.01) |

(52) U.S. Cl.
CPC .... *A61M 16/0006* (2014.02); *A61M 16/0069* (2014.02); *A61M 16/06* (2013.01);
(Continued)

(58) Field of Classification Search
CPC ............ A61M 16/006; A61M 16/0069; A61M 2016/003; A61M 2205/3375; A61M 2016/0039; A61M 2205/183
See application file for complete search history.

(56) References Cited

U.S. PATENT DOCUMENTS

| | | | |
|---|---|---|---|
| 2,794,341 | A | 6/1957 | Bernard |
| 4,683,796 | A | 8/1987 | Salaman et al. |
| | | (Continued) | |

FOREIGN PATENT DOCUMENTS

| | | |
|---|---|---|
| AU | 2013201312 A1 | 3/2013 |
| AU | 2014271343 A1 | 1/2015 |

OTHER PUBLICATIONS

Extended European Search Report issued in corresponding European Patent Application No. 22208348.7, mailed Jun. 13, 2023, 7 pages.

(Continued)

*Primary Examiner* — Margaret M Luarca
(74) *Attorney, Agent, or Firm* — Botos Churchill IP Law LLP

(57) ABSTRACT

A respiratory therapy (RT) system may be configured for acoustic operations. Such a system may include one or more acoustic generators to produce an inaudible acoustic signal that may be implemented for different uses. The acoustic generator(s), such as when coupled to a patient interface or air circuit of a respiratory therapy device, may provide inaudible acoustic signals whereby data concerning respiratory therapy may be collected at low cost, reducing cost of care in providing respiratory therapy. For example, the acoustic generator(s) may be configured to generate an acoustic signal indicative of one or more parameters, such as a flow rate or a pressure of the flow of air, or a type of or useable life of a component (e.g. patient interface). The system may have an acoustic receiver that may detect one or more acoustic signals from the acoustic generator, the RT system, the patient or the environment.

21 Claims, 18 Drawing Sheets

(52) U.S. Cl.
CPC . *A61M 16/0683* (2013.01); *A61M 2016/0027*
(2013.01); *A61M 2016/003* (2013.01); *A61M*
*16/16* (2013.01); *A61M 2205/186* (2013.01);
*A61M 2205/3368* (2013.01); *A61M 2205/3375*
(2013.01)

(56) References Cited

U.S. PATENT DOCUMENTS

| | | | |
|---|---|---|---|
| 4,944,310 | A | 7/1990 | Sullivan |
| 7,093,501 | B2 | 8/2006 | Kudo et al. |
| 9,138,167 | B1 | 9/2015 | Leydon |
| 9,347,932 | B2 | 5/2016 | Tao et al. |
| 2006/0107755 | A1 | 5/2006 | Kuo et al. |
| 2013/0239655 | A1 | 9/2013 | Rai et al. |
| 2014/0116438 | A1 | 5/2014 | Reed |
| 2014/0260667 | A1 | 9/2014 | Berkcan et al. |
| 2015/0367092 | A1 | 12/2015 | Goff et al. |
| 2016/0166785 | A1 | 6/2016 | Morrison et al. |
| 2017/0197056 | A1* | 7/2017 | Van Schalkwyk ...... G01F 25/15 |

OTHER PUBLICATIONS

Extended European Search Report for Application No. EP18828293 dated March Mar. 13, 2021.
International Preliminary Report on Patentability issued in application No. PCT/AU2018/050683 on Aug. 27, 2019.
Ravichandran, Balaje Dhanram, "Development of acoustic sensor for flow rate monitoring," A Thesis Presented in Partial Fulfillment of the Requirements for the Degree Master of Science, Jun. 2012, pp. 1-53.
West, John B., "Respiratory Physiology", Lippincott Williams & Wilkins, 9th Edition published 2012.
Extended European Search Report in EP Application No. 42400771. 4, dated Mar. 17, 2025. 11 pages.

* cited by examiner

Nasal cavity

Oral cavity

Larynx

Vocal folds

Oesophagus

Trachea

Bronchus

Lung

Heart

Diaphragm

Alveolar sacs

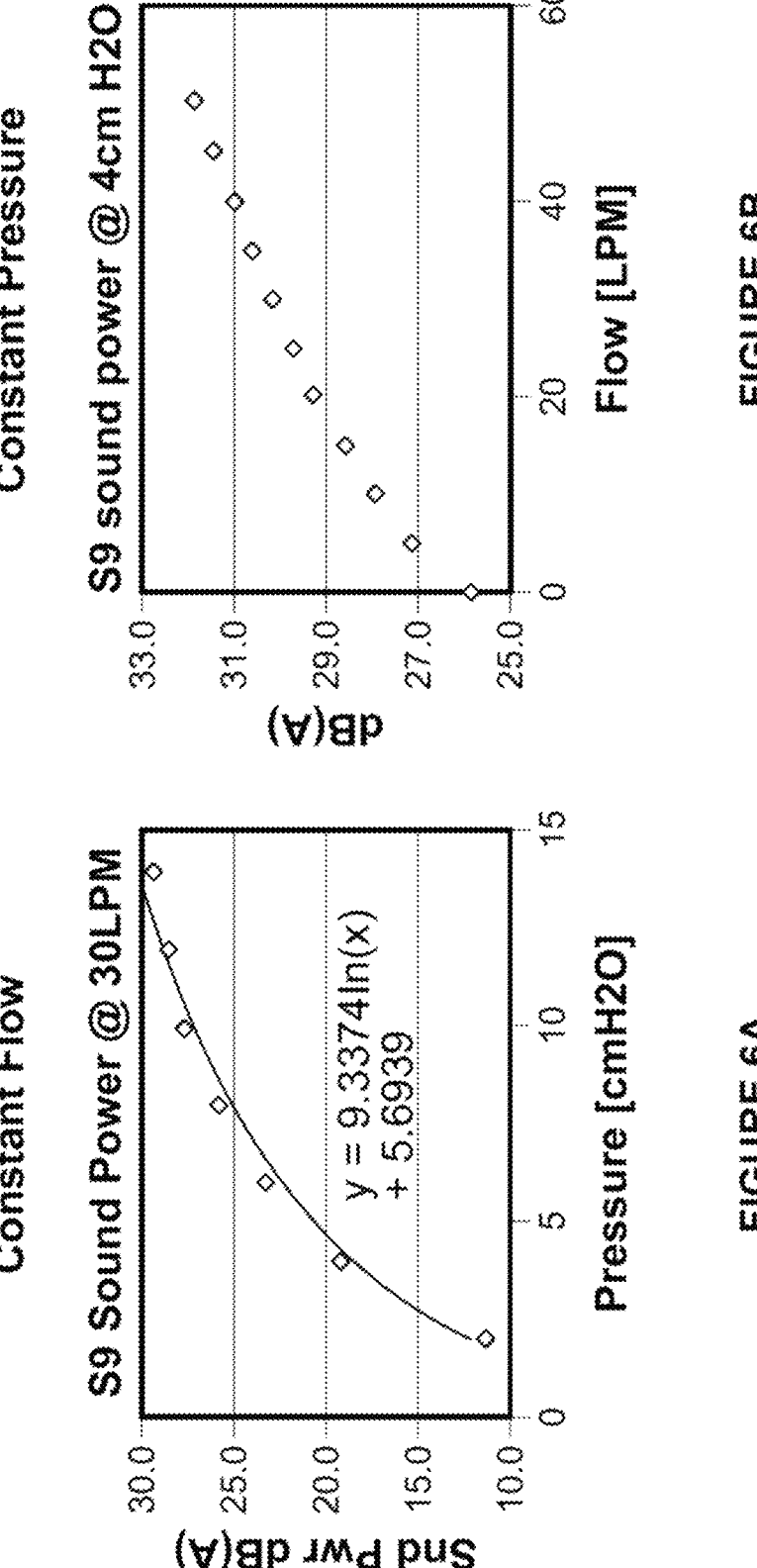

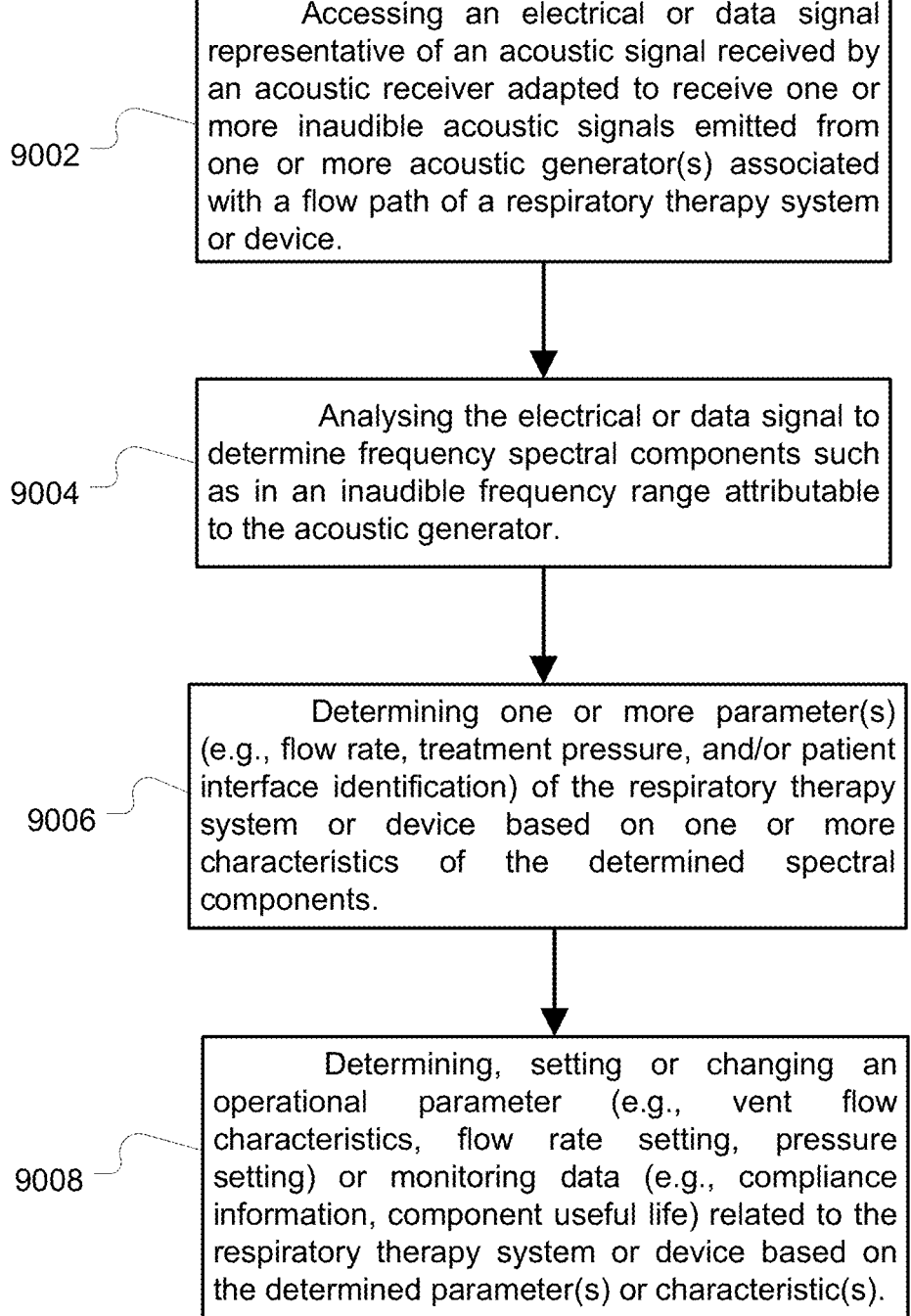

9002 — Accessing an electrical or data signal representative of an acoustic signal received by an acoustic receiver adapted to receive one or more inaudible acoustic signals emitted from one or more acoustic generator(s) associated with a flow path of a respiratory therapy system or device.

9004 — Analysing the electrical or data signal to determine frequency spectral components such as in an inaudible frequency range attributable to the acoustic generator.

9006 — Determining one or more parameter(s) (e.g., flow rate, treatment pressure, and/or patient interface identification) of the respiratory therapy system or device based on one or more characteristics of the determined spectral components.

9008 — Determining, setting or changing an operational parameter (e.g., vent flow characteristics, flow rate setting, pressure setting) or monitoring data (e.g., compliance information, component useful life) related to the respiratory therapy system or device based on the determined parameter(s) or characteristic(s).

FIGURE 9

ACOUSTIC MEASUREMENT SYSTEMS AND METHODS

1 CROSS-REFERENCE TO RELATED APPLICATIONS

This application is a continuation of U.S. patent application Ser. No. 16/626,082, filed on Dec. 23, 2019, which is a national phase entry under 35 U.S.C. § 371 of International Application No. PCT/AU2018/050683 filed Jul. 3, 2018, published in English, which claims priority from Australian Provisional Application No. 2017902594, filed Jul. 4, 2017, all of which are incorporated herein by reference.

2 BACKGROUND OF THE TECHNOLOGY

2.1 Field of the Technology

The present technology relates to one or more of the detection, diagnosis, treatment, prevention and amelioration of respiratory-related disorders. The present technology also relates to medical devices or apparatus, and their use.

2.2 Description of the Related Art 2.2.1 Human Respiratory System and its Disorders The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the inhaled air into the venous blood and carbon dioxide to move in the opposite direction. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "*Respiratory Physiology*", by John B. West, Lippincott Williams & Wilkins, 9th edition published 2012.

A range of respiratory disorders exist. Certain disorders may be characterised by particular events, e.g. apneas, hypopneas, and hyperpneas.

Obstructive Sleep Apnea (OSA) is a respiratory disorder characterised by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods known as apneas, typically of 30 to 120 seconds in duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

A range of therapies have been used to treat or ameliorate such conditions. Furthermore, otherwise healthy individuals may take advantage of such therapies to prevent respiratory disorders from arising. However, these have a number of shortcomings.

2.2.2 Therapy

Various therapies, such as Continuous Positive Airway Pressure (CPAP) therapy, high flow therapy (HFT), non-invasive ventilation (NIV) and invasive ventilation (IV) have been used to treat one or more of the above respiratory disorders.

2.2.3 Treatment Systems

These therapies may be provided by a treatment system or device. Such systems and devices may also be used to diagnose a condition without treating it.

A treatment system may comprise a Respiratory Pressure Therapy Device (RPT device), an air circuit, a humidifier, a patient interface, and data management.

2.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 $cmH_2O$ relative to ambient pressure. For other forms of therapy, such as the delivery of oxygen, the patient interface may not include a seal sufficient to facilitate delivery to the airways of a supply of gas at a positive pressure of about 10 $cmH_2O$.

2.2.3.2 Respiratory Therapy (RT) Device

A respiratory therapy (RT) device, such as a respiratory pressure therapy (RPT) device, may be used to deliver one or more of a number of therapies described above, such as by generating a flow of air for delivery to an entrance to the airways. The flow of air may be pressurised. Examples of RPT devices include a CPAP device and a ventilator. A respiratory therapy (RT) device in some cases may be a high flow therapy (HFT) device, which provides a high flow respiratory therapy.

Air pressure generators are known in a range of applications, e.g. industrial-scale ventilation systems. However, air pressure generators for medical applications have particular requirements not fulfilled by more generalised air pressure generators, such as the reliability, size and weight requirements of medical devices. In addition, even devices designed for medical treatment may suffer from shortcomings, pertaining to one or more of: comfort, noise, ease of use, efficacy, size, weight, manufacturability, cost, and reliability.

Examples of RPT devices include the S9 Sleep Therapy System, manufactured by ResMed Limited, ventilators such as the ResMed Stellar™ Series of Adult and Paediatric Ventilators and the ResMed Astral™ 150 ventilator.

The designer of a device may be presented with an infinite number of choices to make. Design criteria often conflict, meaning that certain design choices are far from routine or inevitable. Furthermore, the comfort and efficacy of certain aspects may be highly sensitive to small, subtle changes in one or more parameters.

2.2.3.3 Humidifier

Delivery of a flow of air without humidification may cause drying of airways. The use of a humidifier with an RPT device and the patient interface produces humidified gas that minimizes drying of the nasal mucosa and increases patient airway comfort. In addition in cooler climates, warm air applied generally to the face area in and about the patient interface is more comfortable than cold air.

2.2.3.4 Vent Technologies

Some forms of treatment systems may include a vent to allow the washout of exhaled carbon dioxide. The vent may allow a flow of gas from an interior space of a patient interface, e.g., the plenum chamber, to an exterior of the patient interface, e.g., to ambient.

2.2.3.5 Sensing and Data Management

One (e.g. a user, a caregiver, a clinician, an insurance company or a technician) may wish to collect data in relation to a respiratory therapy, whether they relate to the user, individual components used for therapy, or the therapy system as a whole. There exist numerous situations in providing respiratory therapy to a patient where one or more parties involved therein may benefit from collection of therapy related data, and leveraging the collected data.

In the past, an array of solutions have been employed, or proposed, in the field of respiratory therapy in relation this endeavour. For example, sensors/transducers have been used, and proposed in a plethora of forms to collect data in relation to environmental conditions, information in relation to the user, identification of components, therapy operating conditions or the like. Indeed, many RPT devices comprise one or more sensors, such as a flow rate sensor, a pressure sensor, a humidity sensor, a temperature sensor and the like.

However, sensors/transducers typically require a suite of additional componentry, which may hinder their adoption in many forms. For instance, data collected by the sensors/transducers must then be communicated to be saved and/or analysed, for example from the sensor to a memory and/or a processor. This, and the aforementioned sensors, may further increase cost of design, testing, and/or manufacturing to the medical device manufacturer, and/or may increase the cost and complexity to the end user or patient.

It is also noted that some components of a respiratory therapy system are to be replaced at a higher frequency than others for effective performance and therefore therapy. For example, a patient interface comprising a silicone seal-forming portion may be replaced by some users in periods of months (e.g. 3 months), whereas RT devices may be replaced or upgraded every few years (e.g. 3 years). In such situations, integrating costly electrical and/or mechanical features to the oft-replaced component(s), such as the patient interface, may be detrimental to providing a most cost-effective therapy, and potentially environmentally unfriendly due to the increased waste.

For those components that are to be replaced at regular intervals (e.g. a patient interface), a user or caregiver regularly face challenges in being reliably and accurately notified, at a low cost, when their component is due to be replaced. When they are replaced, the component may then necessitate the user or caregiver to change one or more settings in the therapy system (e.g. a software setting in the RT device) to ensure that the system is taking full advantage of the component being used.

Furthermore, many proposed solutions in relation to sensors and/or transducers may be limited in that if a sensor is proposed to be located at a distance to where its data is to be saved and/or analysed, often this may further increase a complexity and/or cost of implementation. For example, where a patient interface comprises a sensor, they may often require an electrical connection to the RT device, which may further increase a complexity and/or cost of implementation.

Also, designers of RT devices face numerous choices, and often arrive at different solutions when compared to other devices on the market such as by a competitor, or indeed, by the same manufacturer but produced at a different time. As a result, the associated electrical connector provided may be only connectible to a particular RT device. This may have an unintended effect of creating incompatibility which can be a disadvantage to a particular sub-segment of consumers, and/or it may reduce consumer choice.

3 BRIEF SUMMARY OF THE TECHNOLOGY

The present technology is directed towards providing medical devices used in the diagnosis, amelioration, treatment, or prevention of respiratory disorders having one or more of improved comfort, cost, efficacy, ease of use, user engagement, and manufacturability.

A first aspect of the present technology relates to apparatus used in the diagnosis, amelioration, treatment or prevention of a respiratory disorder.

Another aspect of the present technology relates to methods used in the diagnosis, amelioration, treatment or prevention of a respiratory disorder.

One form of the present technology comprises an acoustic resonance sensor.

Another aspect of one form of the present technology is an acoustic resonance sensor for detection of air flow rate and/or air pressure in a medical device.

Another aspect of one form of the present technology is an acoustic resonance sensor for determination of compliance with a medical treatment regime.

Another aspect of one form of the present technology is an acoustic resonance sensor for identifying a patient interface. The sensor may be implemented to provide data to inform a medical treatment device of suitable operational particulars specific to an identified patient interface.

Another aspect of one form of the present technology is an acoustic resonance sensor for monitoring medical treatment. The monitoring sensor may be implemented to provide data to a health management system for determination of one or more clinical factors, such clinical factors including at least: patient compliance data in relation to compliance with a prescribed medical treatment; data in relation to the physical condition of the patient interface for determination of suitability of the patient interface to support a prescribed medical treatment; data in relation to real-time medical treatment operational factors affecting the efficacy of a prescribed medical treatment.

Another aspect of one form of the present technology is an acoustic resonance sensor for determining respiratory therapy operating parameters including, but not limited to: air flow rate delivered to a patient interface, air pressure in the plenum chamber or other conduits coupled with a patient interface; humidity of air delivered to or present in the plenum chamber or conduits coupled with the patient interface; the relative or absolute partial concentration of a gas (e.g. carbon dioxide, carbon monoxide, or ammonia) in the air expired by a patient.

Another aspect of one form of the present technology comprises a respiratory therapy (RT) device; a patient interface adapted to receive a flow of breathable gas from the RT device, the flow being provided at a flow rate suitable for therapy of a patient; and an acoustic generator adapted to produce an inaudible acoustic signal having a frequency representative of the flow rate and/or pressure of breathable gas received by or directed to the patient interface. The present aspect of one form of the present technology may also comprise an acoustic receiver adapted to receive the inaudible or near inaudible acoustic signal generated by the acoustic generator and to convert the signal into a pressure or flow rate signal for a processor that is adapted to receive the pressure or flow rate signal and to process the pressure or flow rate signal to determine one or more treatment parameters.

The aspect of one form of the present technology addresses a need for a simple, reliable, low cost, acoustic resonance flow rate or pressure measurement method and device.

Some versions of the present technology may include a device for measuring a gas characteristic associated with a gas flow. The device may include an acoustic generator configured to generate an acoustic signal as a function of a gas characteristic of the gas flow. The acoustic signal being substantially inaudible to human hearing.

In some versions, the acoustic signal may be a substantially ultrasonic acoustic signal. The ultrasonic acoustic signal may comprise a dominant acoustic component having a frequency greater than at least 20,000 Hz. The ultrasonic acoustic signal may comprise a dominant acoustic component having a frequency greater than at least 18,000 Hz. The ultrasonic acoustic signal may comprise a dominant acoustic component having a frequency greater than at least 17,000 Hz. The acoustic generator may be adapted to be incorporated into a patient interface suitable for a respiratory therapy. The acoustic generator may be located in fluid communication with a plenum chamber of the patient interface for measurement of a gas pressure of a respiratory therapy gas within the plenum chamber. The acoustic generator may be adapted to be incorporated into an air flow conduit suitable for a respiratory therapy. The acoustic generator may be located in fluid communication with an internal flow path of the air flow conduit for measurement of either a gas pressure or a gas flow rate of a respiratory therapy gas flow within the internal flow path.

In some versions, the acoustic generator may be provided or configured in a connector module adapted to be connected to an air flow circuit intermediate between a patient interface and a respiratory therapy device for measurement of a flow rate of a gas between the respiratory therapy device and the patient interface. The acoustic generator may be adapted to be incorporated into a respiratory therapy device for monitoring of gas flow rates associated with the respiratory therapy device. The acoustic generator may be located adjacent an air flow outlet port of the respiratory therapy device for measurement of a gas flow rate of a gas exiting the respiratory therapy device via the air flow outlet port. The acoustic generator may be a whistle. In some versions, the gas flow may be associated with a respiratory therapy delivered by a respiratory therapy device and wherein the acoustic generator may be adapted to generate the acoustic signal to provide an indication attributable to the respiratory therapy or to a component of the respiratory therapy device. In some versions, the acoustic generator may be selected from a group consisting of: a whistle, a resonant pipe, a reed, a Helmholtz resonator, a membrane, and a tensioned string. The acoustic generator may be configured to generate the acoustic signal in a detectable range of inaudible sound frequencies as the gas characteristic varies within a predetermined range of a respiratory therapy.

Some versions of the present technology may include an acoustic generator for measuring a gas characteristic associated with a gas flow. The acoustic generator may include a windway comprising a windway inlet and a windway outlet. The windway inlet may be adapted to receive, into said windway, a sample portion of said gas flow. The acoustic generator may include a blade formation adjacent said windway outlet and adapted to interact with said sample portion of said gas flow to produce a turbulent flow of air.

The acoustic generator may include an acoustic chamber in fluid communication with said windway and comprising a gas flow inlet at a first end of said acoustic chamber and a gas flow outlet at a second end of said acoustic chamber. The acoustic chamber may be configured to produce a back pressure dependent upon a flow rate of the sample portion of said gas flow. The acoustic generator may be configured to generate an inaudible acoustic signal having an acoustic frequency dependent on said back pressure.

Some versions of the present technology may include an acoustic generator for measuring flow rate or pressure of a gas flow. The acoustic generator may include a windway comprising a windway inlet and a windway outlet. The windway inlet may be adapted to receive, into said windway, a sample portion of said gas flow. The acoustic generator may include a blade formation adjacent said windway outlet and adapted to interact with said sample portion of said gas flow to produce a turbulent flow of air. The acoustic generator may include an acoustic chamber in fluid communication with said windway and comprising a gas flow inlet at a first end of said acoustic chamber and a gas flow outlet at a second end of said acoustic chamber. The acoustic generator may be configured to generate an inaudible acoustic signal having an acoustic frequency dependent on a gas characteristic of the gas flow.

In some versions, a device may include an acoustic receiver in communication with the acoustic generator. The acoustic receiver may be configured to measure an acoustic frequency of the inaudible acoustic signal produced by the acoustic generator and to provide an indication of a gas characteristic of said gas flow based on the measured acoustic frequency. The inaudible acoustic signal may be generated at a frequency which may be inaudible to humans. The acoustic generator may generate an ultrasonic acoustic signal.

Some versions of the present technology may include an acoustic generator in a system for treating a respiratory disorder in a patient. The system may include a patient interface, a pressure generator configured to generate, for treating the respiratory disorder, a downstream air flow having a flow rate and a pressure, and an air path in fluid communication with an air outlet of the pressure generator and an air inlet of the patient interface. The acoustic generator may be located adjacent to or in the patient interface. The acoustic generator may be being in fluid communication with said downstream air flow and with ambient air. The acoustic generator may include a windway inlet adapted to receive a sample portion of said downstream air flow into a windway. The windway may have a windway outlet. The acoustic generator may include a blade formation adjacent said windway outlet and adapted to interact with said sample portion of said downstream air flow to produce a turbulent flow of air. The acoustic generator may include an acoustic chamber in fluid communication with said windway. The acoustic chamber may include a gas flow inlet at a first end of said acoustic chamber and a gas flow outlet at a second end of said acoustic chamber. The acoustic generator may be adapted to generate an inaudible acoustic signal having an acoustic frequency dependent upon: the flow rate of the downstream air flow delivered to the patient interface; or the pressure in the patient interface.

Some versions of the present technology may include an acoustic generator in a system for treating a respiratory disorder in a patient. The system may include a patient interface, a pressure generator configured to generate, for treating the respiratory disorder, a downstream air flow having a flow rate and a pressure, and/or an air path in fluid communication with an air outlet of the pressure generator and an air inlet of the patient interface. The acoustic generator may be located adjacent to or in said patient interface. The acoustic generator may include a whistle in fluid communication with said downstream air flow. The whistle may be adapted to generate an inaudible acoustic signal having an acoustic frequency dependent on: the flow rate of the downstream air flow delivered to the patient interface; or the pressure in the patient interface.

In some versions, the inaudible acoustic signal may include an ultrasonic signal. The inaudible acoustic signal may include a frequency that may be inaudible to humans. The inaudible acoustic signal may include a dominant acoustic component having a frequency greater than at least 20,000 Hz. The inaudible acoustic signal may include a dominant acoustic component having a frequency greater than at least 18,000 Hz. The inaudible acoustic signal may include a dominant acoustic component having a frequency greater than at least 17,000 Hz. The acoustic generator may include a windway comprising a windway inlet and a windway outlet. The windway inlet may be adapted to receive, into the windway, a sample portion of said downstream air flow. The acoustic generator may include a blade formation that may be adjacent to said windway outlet and may be adapted to interact with said sample portion of said downstream air flow to produce a turbulent flow of air. The acoustic generator may include an acoustic chamber in fluid communication with said windway and may comprise a gas flow inlet at a first end of said acoustic chamber and a gas flow outlet at a second end of said acoustic chamber. The acoustic chamber may be configured to produce a back pressure dependent upon a flow rate of the sample portion of said downstream air flow. The turbulent flow of air may interact with said back pressure to produce the inaudible acoustic signal.

In some versions, windway may have a length of between about 3 mm and about 7 mm. The windway may have a length of between about 5 mm and about 7 mm. The windway may have a width of between about 0.7 mm and about 1.5 mm. The windway may have a height of between about 0.6 mm and about 0.7 mm. The acoustic chamber may have a horn region at a distal end of said acoustic chamber. The horn region may have a length of between about 2 mm and about 4.5 mm. The horn region may have a radius of curvature of between about 2 degree and about 8.5 degrees. The blade formation may include a leading edge that may be adapted to minimise human audible turbulent noise in operation. The windway outlet and the leading edge of the blade formation may be separated by a distance of between about 0.5 mm and about 2 mm. The leading edge may be rounded to reduce audible turbulent noise generated by the acoustic generator. The leading edge may include either an undercut or an overcut to reduce audible turbulent noise generated by the acoustic generator. The leading edge may be located between about 1 mm and about 5 mm from the windway outlet. The leading edge of the blade formation may be positioned in line with a central axis of the windway. The leading edge of the blade formation may be positioned below a centre of the windway. The blade formation may include a first blade formation surface substantially aligned with a central axis of the windway. The blade formation may include a second blade formation surface aligned at a blade angle with respect to the central axis of the windway. The blade angle may be between about 20 degrees and about 40 degrees. The blade angle may be about 30 degrees.

In some versions of the acoustic generator, the pressure generator may include another acoustic generator located adjacent the air outlet of the pressure generator and may be in fluid communication with the downstream air flow. The another acoustic generator may include a windway including a windway inlet and a windway outlet. The windway inlet may be adapted to receive, into the windway, a sample portion of said downstream air flow. The another acoustic generator may include a blade formation adjacent said windway outlet that may be adapted to interact with said sample portion of said downstream air flow to produce a turbulent flow of air. The another acoustic generator may include an acoustic chamber in fluid communication with said windway and may include a gas flow inlet at a first end of said acoustic chamber and a gas flow outlet at a second end of said acoustic chamber. Said acoustic chamber may be configured to produce a back pressure dependent upon a flow rate of the sample portion of said downstream air flow exiting said air outlet of said pressure generator. The turbulent flow of air may interact with said back pressure to produce another acoustic signal having an acoustic frequency dependent upon the flow rate or the pressure of the downstream air flow exiting the air outlet of said pressure generator.

In some versions, said another acoustic generator and said acoustic generator may be matched such that the inaudible acoustic signal and the another acoustic signal have substantially equal acoustic frequencies in response to a given flow rate or pressure of the downstream air flow. In use, the acoustic signals may be generated by said acoustic generator and said another acoustic generator to interact to produce a combined acoustic beat signal representative of a difference in flow rate or pressure between the downstream air flow exiting the air outlet of said pressure generator and the downstream air flow delivered to said patient interface.

In some versions of the acoustic generator(s) described herein, the system may further include an acoustic receiver configured to detect acoustic signals generated by the acoustic generator(s). The acoustic receiver may be adapted to detect an acoustic beat frequency formed from interaction of the acoustic signals generated by said acoustic generator and said another acoustic generator.

Some versions of the present technology may include a flow rate sensor for measuring a gas flow rate of a flow of breathable gas being directed to a patient interface for treatment of a respiratory disorder. The flow rate sensor may include first and second acoustic generators. The first and second acoustic generators may be separated by a distance along a flow path to the patient interface. The first and second acoustic generators may be configured to sample the flow of breathable gas within the flow path. The first and second acoustic generators may be are configured to generate acoustic signals that produce a detectable beat frequency representative of a flow rate of the flow path.

Some versions of the present technology may include a system for measuring a characteristic of a flow of breathable gas being directed to a patient interface for treatment of a respiratory disorder. The system may include an acoustic generator in communication with said flow of breathable gas. The acoustic generator may be configured to generate an inaudible acoustic signal representative of said characteristic of said flow of breathable gas. The system may include an acoustic receiver operatively coupled to receive said inaudible acoustic signal. The acoustic receiver may be configured to generate an electrical signal representative of said inaudible acoustic signal. The system may include a processor. The processor may be configured to receive said electrical signal. The processor may be configured to determine a frequency spectrum of said electrical signal. The processor may be configured to determine said characteristic of said flow of breathable gas from said frequency spectrum.

In some versions, said characteristic may be a pressure of said flow of breathable gas. The inaudible acoustic signal may be an ultrasonic acoustic signal. The ultrasonic acoustic signal may have a frequency of between about 16 kilohertz and about 24 kilohertz. The ultrasonic acoustic signal may be representative of positive gas pressures directed to said patient interface of between about 4 $cmH_2O$ and about 20 $cmH_2O$ above ambient atmospheric pressure. The acoustic generator may be configured to generate the inaudible acoustic signal in a frequency range that may be inaudible to humans over a pressure range of between about 4 $cmH_2O$ and about 20 $cmH_2O$ above ambient atmospheric pressure. The acoustic generator may be coupled adjacent to or integrated with the patient interface. The acoustic generator may be provided adjacent to or integrated with an airflow exit port of a respiratory therapy device adapted to provide said flow of breathable gas. In some versions, an inline connector may be insertable in an air flow path between an air conduit for directing said flow of breathable gas and said patient interface. The inline connector may include the acoustic generator.

In some versions, the acoustic generator may include a windway comprising a windway inlet and a windway outlet. The acoustic generator may include an acoustic outlet. The acoustic generator may include a blade formation. The acoustic generator may include an acoustic chamber in fluid communication with said windway and said acoustic outlet. The acoustic chamber may include a gas flow inlet at a first end of said acoustic chamber and a gas flow outlet at a second end of said acoustic chamber. The acoustic chamber may be configured to produce a back pressure dependent on a gas flow rate or a pressure in the acoustic chamber. The acoustic generator may be located in said patient interface such that said windway inlet may be in fluid communication with a plenum chamber of said patient interface and the acoustic outlet of the acoustic generator may be in fluid communication with ambient air. The acoustic generator may be located in-line with said flow of breathable gas such that the windway inlet may be in fluid communication with said flow of breathable gas.

In some versions, the acoustic generator may include a windway inlet adapted to receive a flow of air. The acoustic generator may be adapted to generate an acoustic signal having a frequency dependent upon a relative or absolute humidity of the flow of air received by said windway inlet. In some versions, the acoustic generator may include a windway inlet adapted to receive a flow of air. In some versions, the acoustic generator may be adapted to generate an acoustic signal having a frequency dependent upon relative or absolute partial concentration of a gas in the flow of air received by said windway inlet. The acoustic generator may be adapted to generate an acoustic signal having a frequency dependent upon a relative or absolute partial concentration of a gas in the flow of air expired by a patient. The gas may comprise or be carbon dioxide or carbon monoxide.

Some versions of the present technology may include a patient interface. The patient interface may include a plenum chamber pressurisable to a therapeutic pressure (e.g., of at least 6 $cmH_2O$) above ambient air pressure. The plenum chamber may include a plenum chamber inlet port. The plenum chamber inlet port may be sized and structured to receive a flow of air at the therapeutic pressure for breathing by a patient. The patient interface may include a seal-forming structure constructed and arranged to maintain said therapeutic pressure in the plenum chamber throughout a patient's respiratory cycle in use. The patient interface may include a positioning and stabilising structure configured to hold the seal-forming structure in a therapeutically effective position on the patient's head. The patient interface may include a washout vent structure configured to allow a vent flow from an interior of the plenum chamber to ambient whilst pressure within the plenum chamber may be positive with respect to ambient. The patient interface may include an acoustic generator. The acoustic generator may include a windway inlet adapted to receive, into a windway, a sample portion of said flow of air. The windway may have a windway outlet. The acoustic generator may have a blade formation adjacent said windway outlet that may be adapted to interact with said sample portion of said flow of air to produce a turbulent flow of air. The acoustic generator may include an acoustic chamber in fluid communication with said windway and may include a gas flow inlet at a first end of said acoustic chamber and a gas flow outlet at a second end of said acoustic chamber. The acoustic generator may be configured to generate an inaudible acoustic signal having an acoustic frequency dependent upon a flow rate of said flow of air delivered into said plenum chamber or a pressure in said plenum chamber.

In some versions, the acoustic generator may be in fluid communication with said plenum chamber. The acoustic generator may be further in fluid communication with ambient air.

Some versions of the present technology may include a method for determining operational parameters associated with a respiratory therapy. The method may be in a respiratory therapy system for treating a respiratory disorder in a patient. The respiratory therapy system may include a pressure generator configured to generate a flow of air having a flow rate for treating the respiratory disorder; and an air conduit in fluid communication with an air outlet of the pressure generator and an air inlet of a patient interface. The method may include, with an acoustic receiver adapted to receive one or more acoustic signals emitted from said pressure generator and/or said patient interface in use, receiving an acoustic signal of the one or more acoustic signals and generating an electrical signal representative of the acoustic signal. The method may include receiving the electrical signal with a processor adapted to analyse said electrical signal. The method may include analysing the electrical signal with said processor to determine frequency spectral components in the acoustic signal.

In some versions, the method may include, in the processor, correlating the frequency spectral components to characteristic signals generated by one or more mechanical components of the pressure generator. The method may include, in the processor, correlating the frequency spectral components to characteristic pneumatic noise signals generated by either the pressure generator, the air conduit or the patient interface. The method may include, in the processor, calculating one or more operational parameters associated with said respiratory therapy system based on the frequency spectral components. The one or more operational parameters may be selected from the group consisting of: gas flow rate; gas pressure; vent flow rate; leak flow rate; blower rotation speed; and impeller blade pass frequency.

Some versions of the present technology may include a method for automatic configuration of a respiratory therapy (RT) device adapted for treating a respiratory disorder in a patient. The respiratory therapy (RT) device may include a blower and a controller configured to control the blower. The method may include controlling, by the controller, a flow of breathable gas through an air circuit to a patient interface such that an acoustic generator located adjacent to or in the patient interface generates an inaudible acoustic signal having a frequency spectrum dependent on a type of the patient interface. The method may include receiving the inaudible acoustic signal with an acoustic receiver. The method may include generating, with the acoustic receiver, a signal representative of the inaudible acoustic signal. The method may include determining the frequency spectrum of the signal representative of the inaudible acoustic signal. The method may include determining the type of the patient interface based on the frequency spectrum. The method may include configuring one or more operational parameters of the controller of the RT device based on the type of patient interface.

Some versions of the present technology may include a method for monitoring a respiratory therapy provided by a respiratory therapy (RT) device comprising a blower and a controller configured to control the blower. The respiratory therapy may be for treating a respiratory disorder in a patient. The method may include with an acoustic receiver, receiving an inaudible acoustic signal and generating an electrical signal representative of the inaudible acoustic signal. The inaudible acoustic signal may be generated by an acoustic generator that may be located adjacent to or in a patient interface receiving a flow of breathable gas from the blower. The inaudible acoustic signal may have a frequency spectrum dependent upon either a gas flow rate or a pressure of the flow of breathable gas as the flow of breathable gas may be provided to the patient interface. The method may include analysing the electrical signal with an acoustic processor to determine frequency spectral components in an inaudible frequency range attributable to the acoustic generator. The method may include determining, in the acoustic processor, the pressure or the gas flow rate of the flow of breathable gas based on the frequency spectral components.

In some versions, the acoustic receiver comprises a microphone connected to the RT device. The acoustic receiver may include a microphone of a mobile computing device located in acoustic vicinity of the acoustic generator. The acoustic processor may include a processor of the mobile computing device.

Some versions of the present technology may include a processor readable medium having processor control instructions recorded therein for automatic configuration of a respiratory therapy (RT) device for treatment of a respiratory disorder. The processor control instructions may include instructions to receive with an acoustic receiver an inaudible acoustic signal, the inaudible acoustic signal being generated by an acoustic generator coupled to a patient interface suitable for providing a respiratory therapy, wherein the inaudible acoustic signal has a frequency spectrum dependent on a type of the patient interface. The processor control instructions may include instructions to determine the frequency spectrum of the inaudible acoustic signal. The processor control instructions may include instructions to determine the type of the patient interface based on the frequency spectrum. The processor control instructions may include instructions to determine one or more operational parameters for the RT device based on the type of the patient interface. The processor control instructions may include instructions to control operation of the RT device using the one or more operational parameters.

Some versions of the present technology may include a processor readable medium having processor control instructions recorded therein for monitoring a respiratory therapy provided by a respiratory therapy (RT) device comprising a blower and a controller configured to control the blower. The respiratory therapy may be for treating a respiratory disorder in a patient. The processor control instructions may include instructions to, with an acoustic receiver, receive an inaudible acoustic signal. The inaudible acoustic signal may be generated by an acoustic generator coupled to a patient interface suitable for the respiratory therapy. The inaudible acoustic signal may have a frequency spectrum dependent upon either a gas flow rate or a pressure of a flow of breathable gas as the flow of breathable gas may be supplied to the patient interface. The processor control instructions may include instructions to determine frequency spectral components in an inaudible frequency range attributable to the acoustic generator from the received inaudible acoustic signal. The processor control instructions may include instructions to determine the gas flow rate or gas pressure of the flow of breathable gas based on the frequency spectral components.

Some versions of the present technology may include a method for identifying a patient interface configured for use with a respiratory therapy (RT) device. The patient interface may be suitable for providing a respiratory therapy to a patient. The method may include receiving an inaudible acoustic signal with an acoustic receiver. The inaudible acoustic signal may be generated by an acoustic generator coupled to a patient interface receiving a downstream air flow from a respiratory therapy device. The acoustic generator may be configured to sample the downstream air flow. The method may include determining, in a processor coupled to the acoustic receiver, a frequency spectrum of the inaudible acoustic signal. The method may include identifying, from a plurality of different types of patient interface, a type of patient interface associated with one or more characteristics of the determined frequency spectrum.

In some versions, the method may include determining an operational parameter of the respiratory therapy device based on the identified type of patient interface. The operational parameter may be or include a treatment pressure or a flow rate. The determining the operational parameter may include determining a vent flow characteristic of a vent of the patient interface. The operational parameter may be determined in a setup process that updates configuration settings for the respiratory therapy device. The method may include enabling a configuration feature of the respiratory therapy device based on the identified type of patient interface. The configuration feature otherwise being disabled in an absence of the identified type of patient interface. The configuration feature may include a type of respiratory therapy suitable for the identified type of patient interface.

In some versions, the method may include repeating (a) the receiving the inaudible acoustic signal and (b) the determining the frequency spectrum of the inaudible acoustic signal. The method may include evaluating, in the processor, long-term changes in frequency spectral characteristics of the determined frequency spectrum. The method may include generating a message concerning useable life of the patient interface based on the evaluating. The evaluating may detect an increase of baseline pressure and/or air flow leakage attributable to sealing properties of the patient interface. In some versions of the method, a mobile processing device may include the acoustic receiver, determine the frequency spectrum and/or communicate data representing the identified type of patient interface to the respiratory therapy device.

The methods, systems, devices and apparatus described herein can provide improved functioning in a processor, such as of a processor of a specific purpose computer, respiratory monitor and/or a respiratory therapy apparatus. Moreover, the described methods, systems, devices and apparatus can provide improvements in the technological field of automated management, monitoring and/or treatment of respiratory conditions, including, for example, sleep disordered breathing.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

4 BRIEF DESCRIPTION OF THE DRAWINGS

The present technology is illustrated by way of example, and not by way of limitation, in the figures of the accompanying drawings, in which like reference numerals refer to similar elements including:

4.1 Therapy Systems

FIG. 1A shows a system including a patient 1000 wearing a patient interface 3000, in the form of nasal pillows, receiving a supply of air at positive pressure from an RPT device 4000. Air from the RPT device 4000 is humidified in a humidifier 5000, and passes along an air circuit 4170 to the patient 1000. A bed partner 1100 is also shown. The patient is sleeping in a supine sleeping position. As illustrated in FIG. 1A, the air circuit may be implemented with an acoustic generator 8500, such as one or more acoustic generators as described in more detail herein. Such an acoustic generator may be through a coupling portion or integrated with a conduit coupler of a conduit of the air circuit.

FIG. 1B shows a system including a patient 1000 wearing a patient interface 3000, in the form of a nasal mask, receiving a supply of air at positive pressure from an RPT device 4000. Air from the RPT device is humidified in a humidifier 5000, and passes along an air circuit 4170 to the patient 1000. As illustrated in FIG. 1B, the patient interface, such as through a coupling portion, coupler/connector or connection port, may be implemented with an acoustic generator 8500, such as an acoustic generator as described in more detail herein.

FIG. 1C shows a system including a patient 1000 wearing a patient interface 3000, in the form of a full-face mask, receiving a supply of air at positive pressure from an RPT device 4000. Air from the RPT device is humidified in a humidifier 5000, and passes along an air circuit 4170 to the patient 1000. The patient is sleeping in a side sleeping position. As illustrated in FIG. 1C, the patient interface and/or the air circuit, may be implemented with an acoustic generator 8500, such as an acoustic generator as described in more detail herein.

4.2 Respiratory System and Facial Anatomy

FIG. 2 shows an overview of a human respiratory system including the nasal and oral cavities, the larynx, vocal folds, oesophagus, trachea, bronchus, lung, alveolar sacs, heart and diaphragm.

4.3 Patient Interface

FIG. 3 shows an example of a patient interface in the form of a nasal mask in accordance with one form of the present technology.

4.4 RPT Device

4.5 Breathing Waveforms

Figure 5:
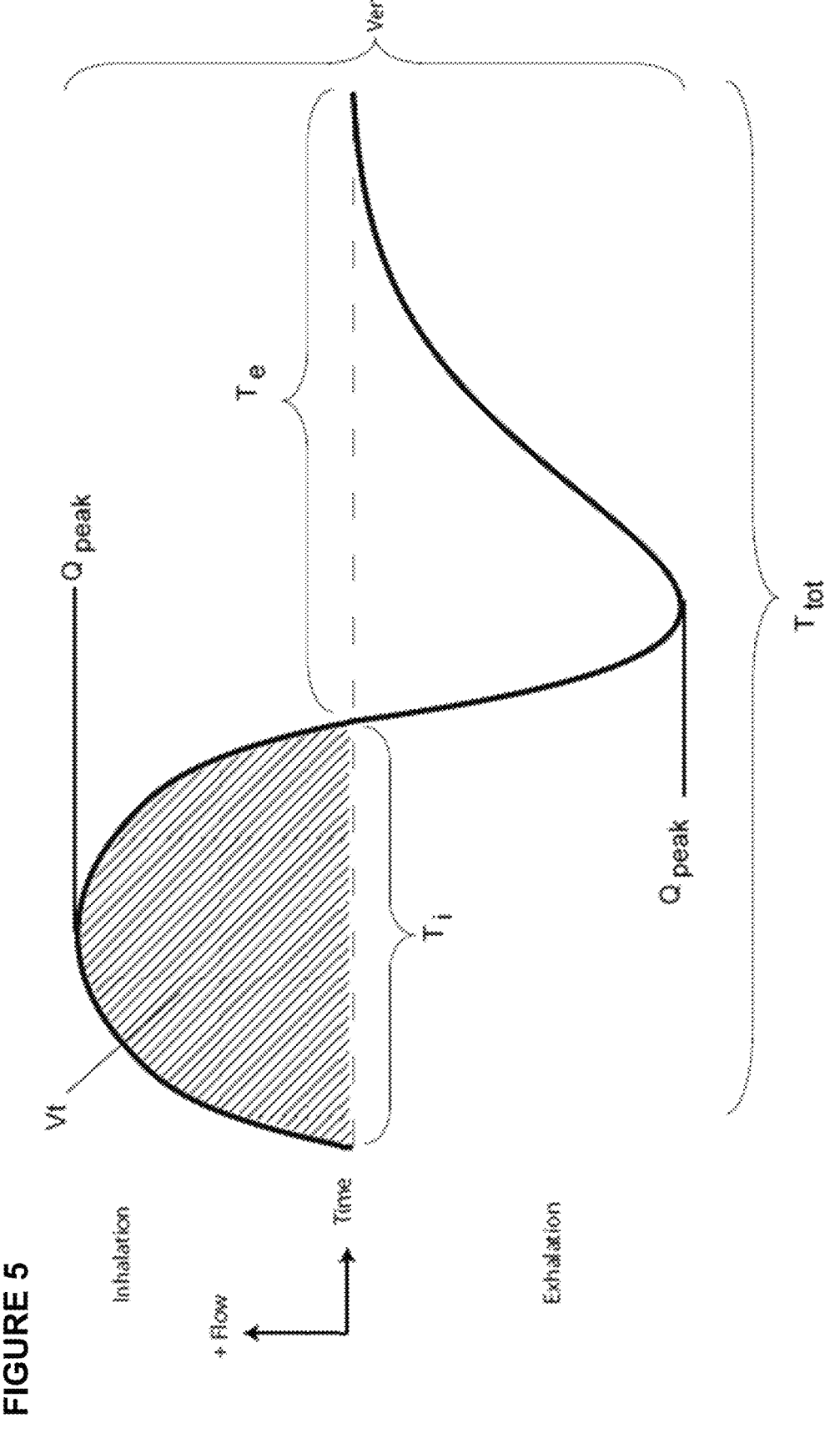

FIG. 5 shows a model typical breath waveform of a person while sleeping. The horizontal axis is time, and the vertical axis is respiratory flow rate. While the parameter values may vary, a typical breath may have the following approximate values: tidal volume, Vt, 0.5 L, inhalation time, Ti, 1.6 s, peak inspiratory flow rate, Qpeak, 0.4 L/s, exhalation time, Te, 2.4 s, peak expiratory flow rate, Qpeak, −0.5 L/s. The total duration of the breath, Ttot, is about 4 s. The person typically breathes at a rate of about 15 breaths per minute (BPM), with Ventilation, Vent, about 7.5 L/min. A typical duty cycle, the ratio of Ti to Ttot, is about 40%.

4.6 Passive Acoustic Analysis

FIG. 6A shows a graph of the noise produced by an exemplary RPT device and a patient interface as a function of pressure at a constant flow rate:

FIG. 6B shows a graph of the noise produced by an exemplary RPT device and a patient interface as a function of flow rate at a constant pressure.

Figure 6C:
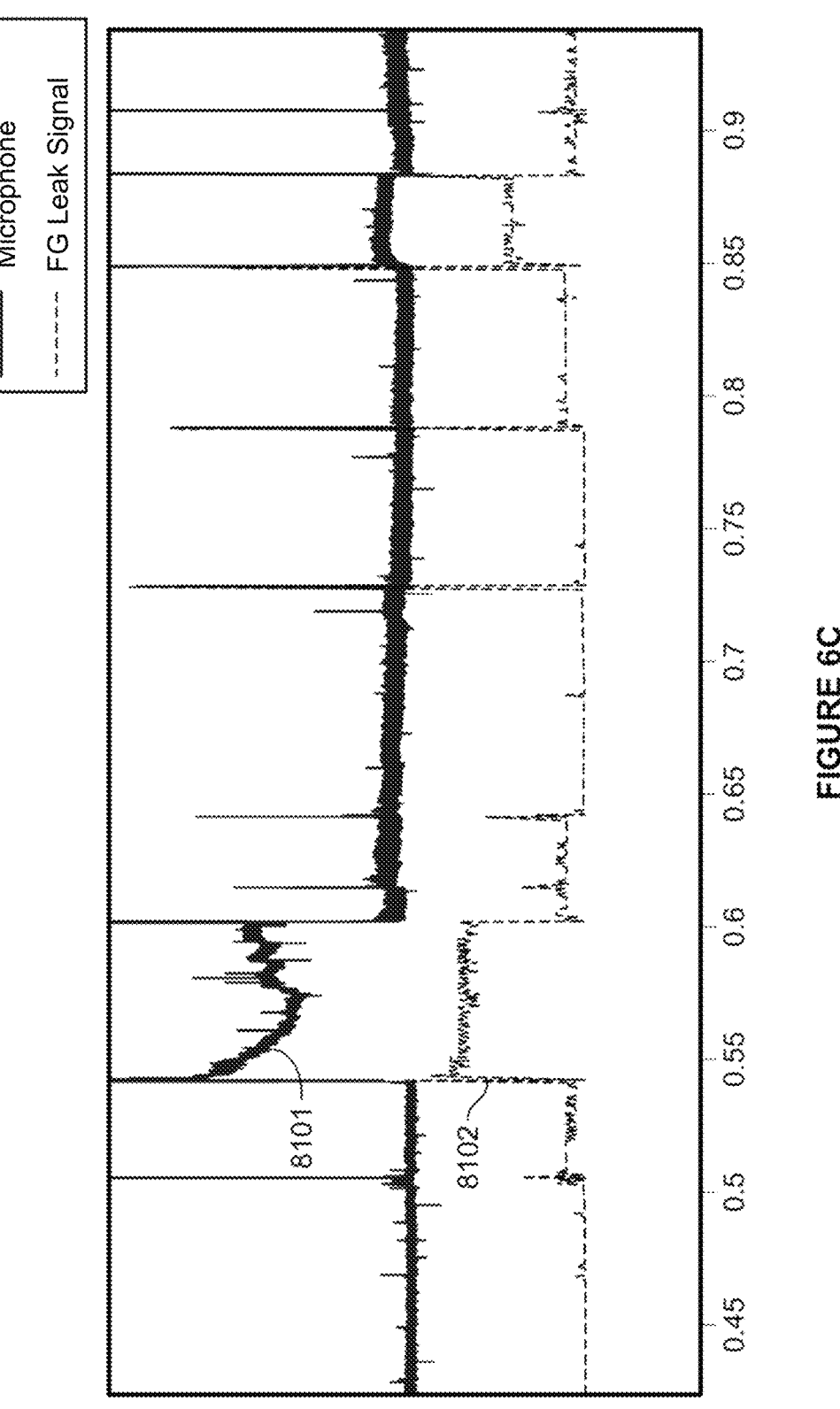

FIG. 6C shows a comparison of a microphone sound signal and a RPT device (flow generator) sound signal.

Figure 6D:
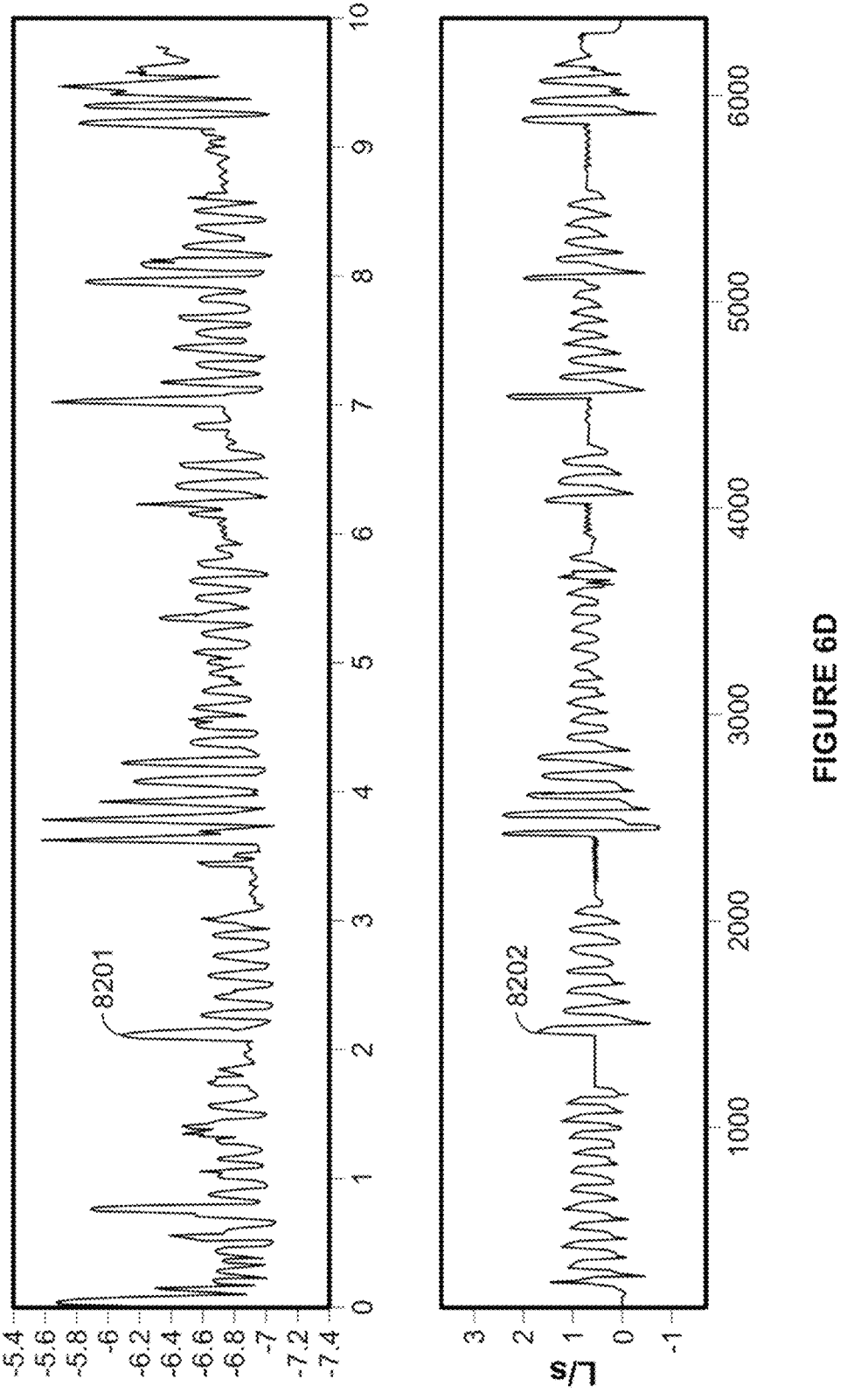

FIG. 6D shows another comparison of a microphone sound signal and a RPT device (flow generator) sound signal

4.7 Active Acoustic Analysis System

Figure 7A:
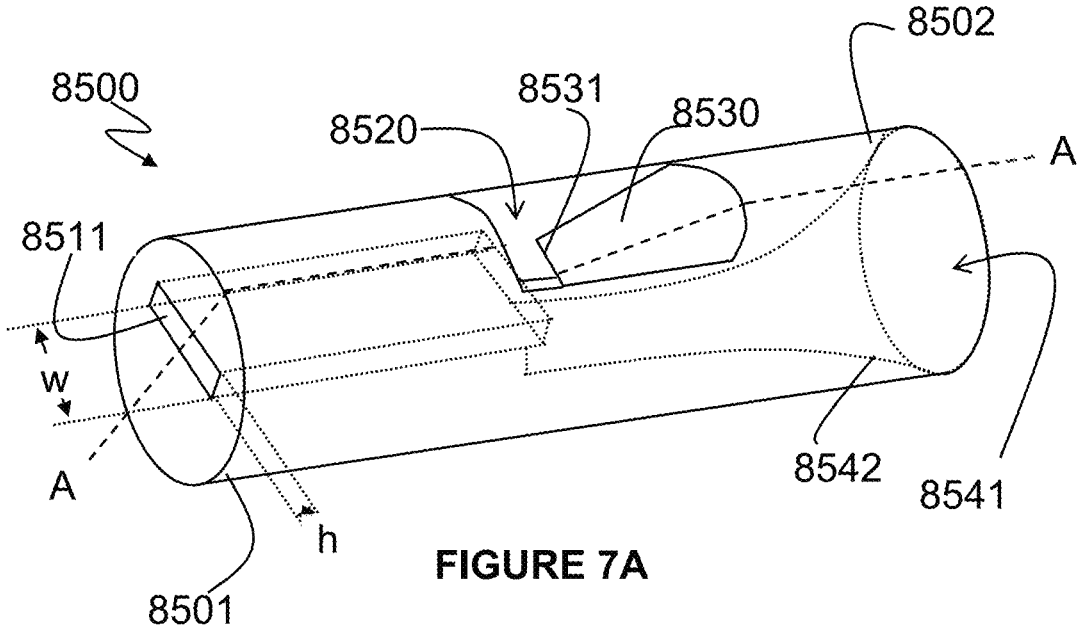
Figure 7B:
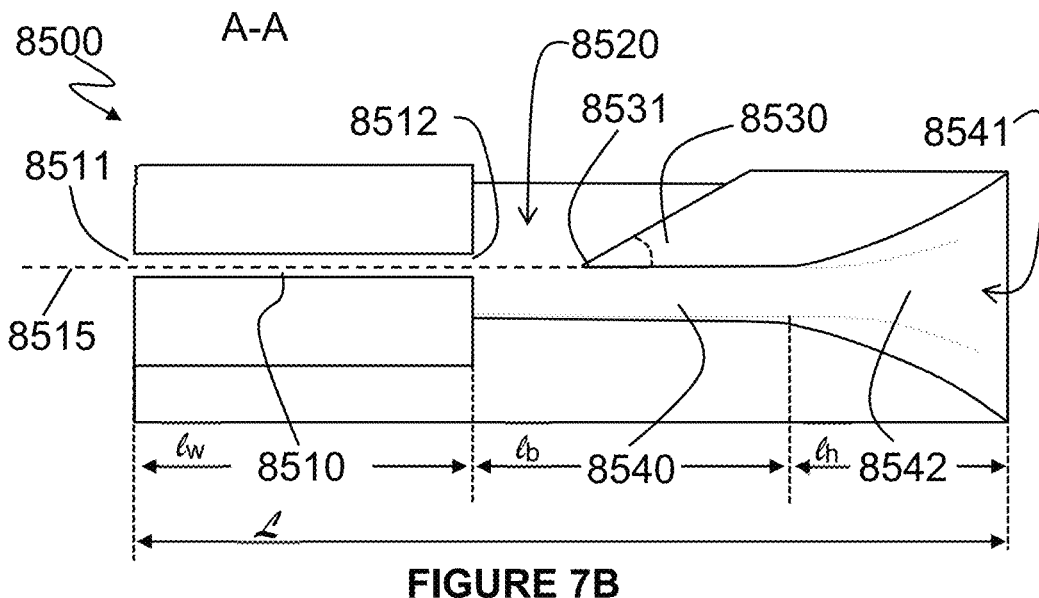
Figure 7C:
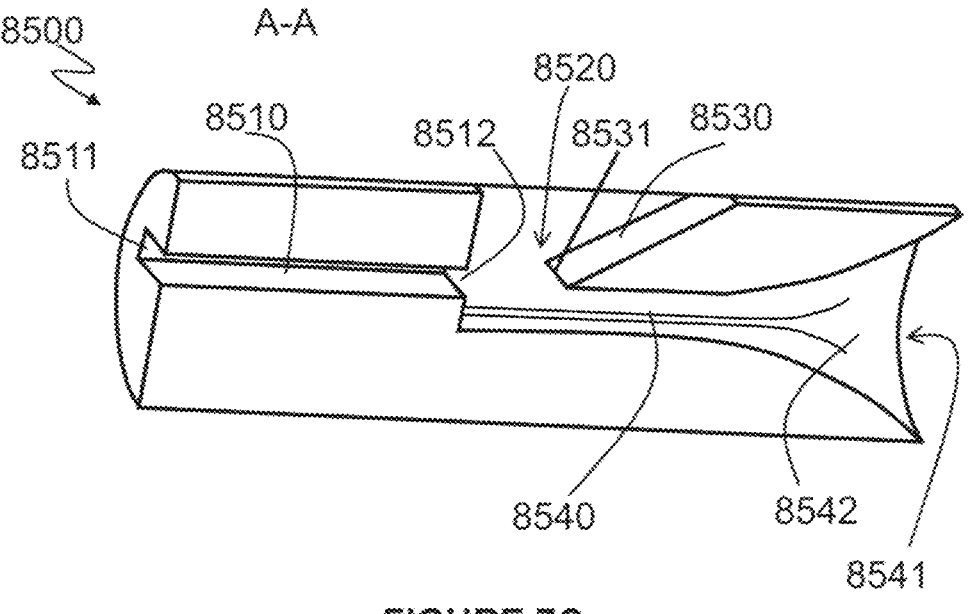

FIGS. 7A to 7C show an example acoustic generator that may be implemented in active acoustic analysis of respiratory pressure therapy systems.

Figure 7D:
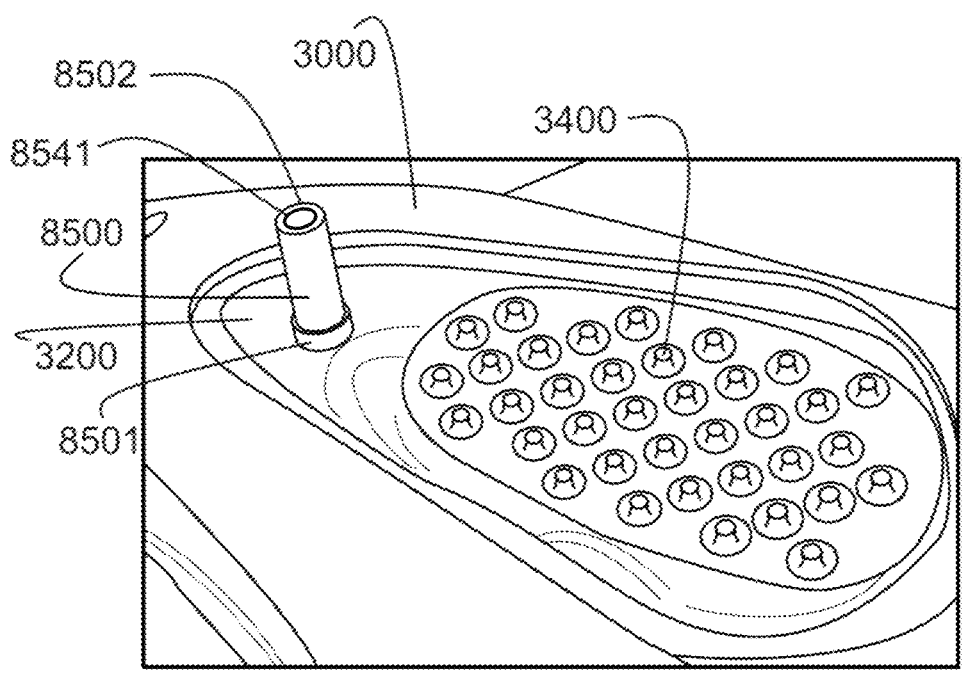

FIG. 7D shows an example implementation of an acoustic generator of FIG. 7A incorporated into a patient interface.

Figure 7E:
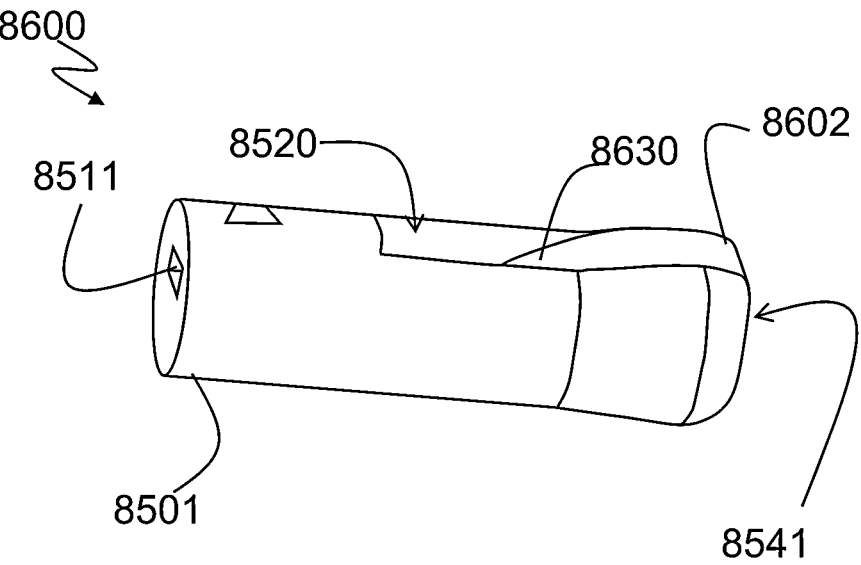
Figure 7F:
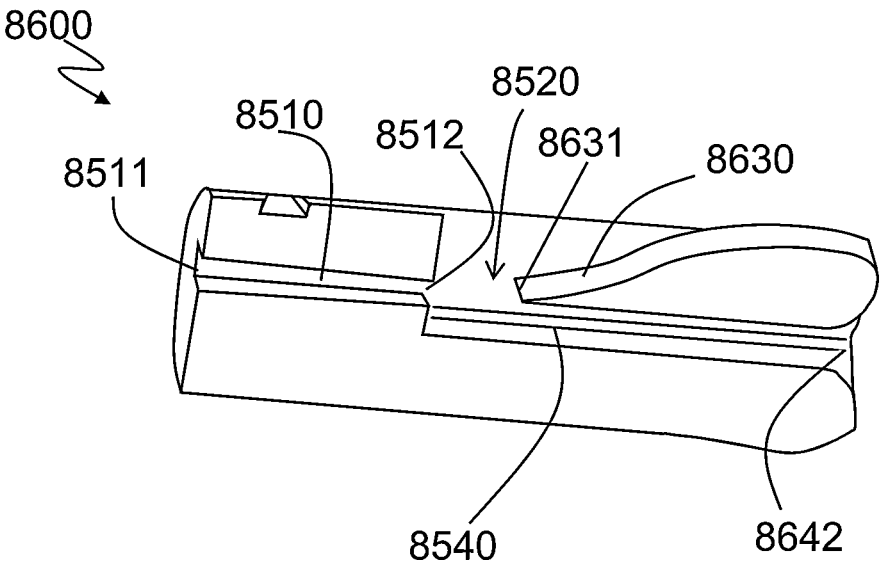

FIGS. 7E and 7F show an alternative configuration of an acoustic generator that may be implemented in active acoustic analysis of respiratory pressure therapy systems.

Figure 7G:
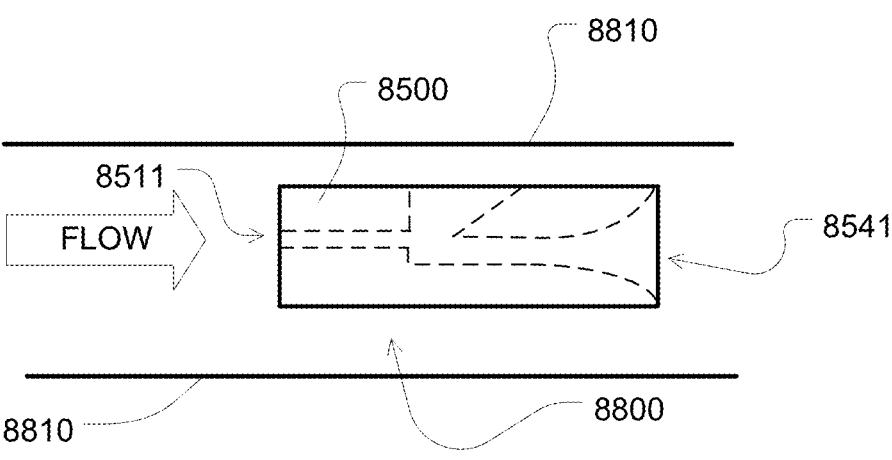
Figure 7H:
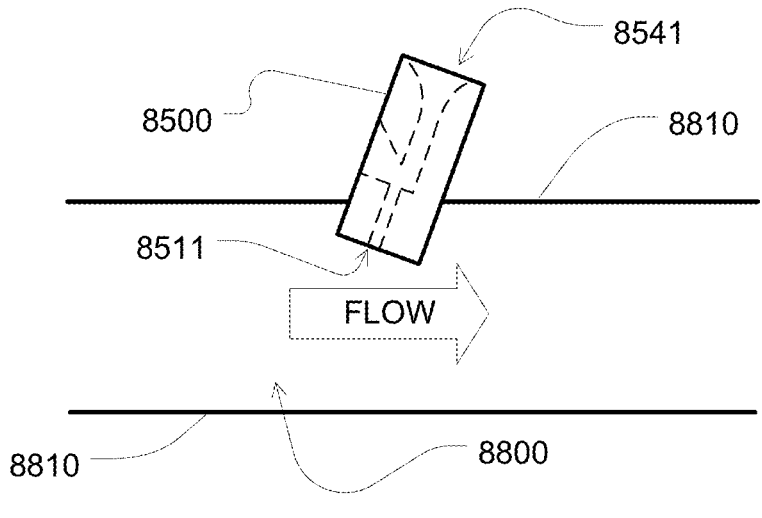

FIGS. 7G and 7H schematically illustrate example implementations of acoustic generators in an in-line configuration and a tapped configuration respectively.

4.8 Active Acoustic Analysis

Figure 8A:
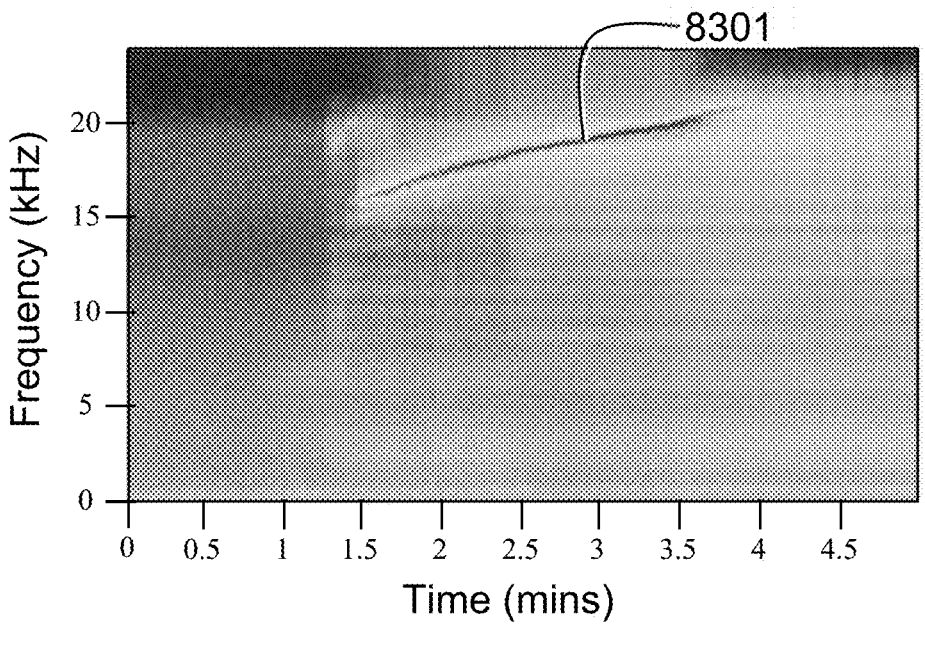

FIG. 8A is a 3-dimensional graph of the frequency detected in an acoustic signal generated by an example acoustic generator of the present technology in conjunction with an RPT system with increasing treatment pressure.

Figure 8B:
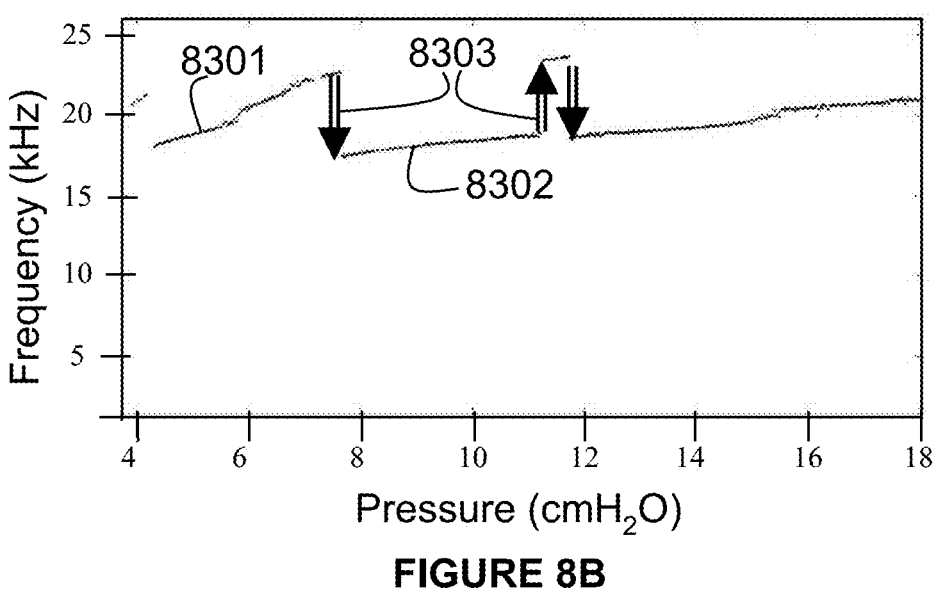

FIG. 8B is a 3-dimensional graph of the frequency detected in an acoustic signal generated by an acoustic generator in conjunction with an RPT system with increasing treatment pressure showing mode hops in the dominant output frequency of the generated acoustic signal.

Figure 8C:
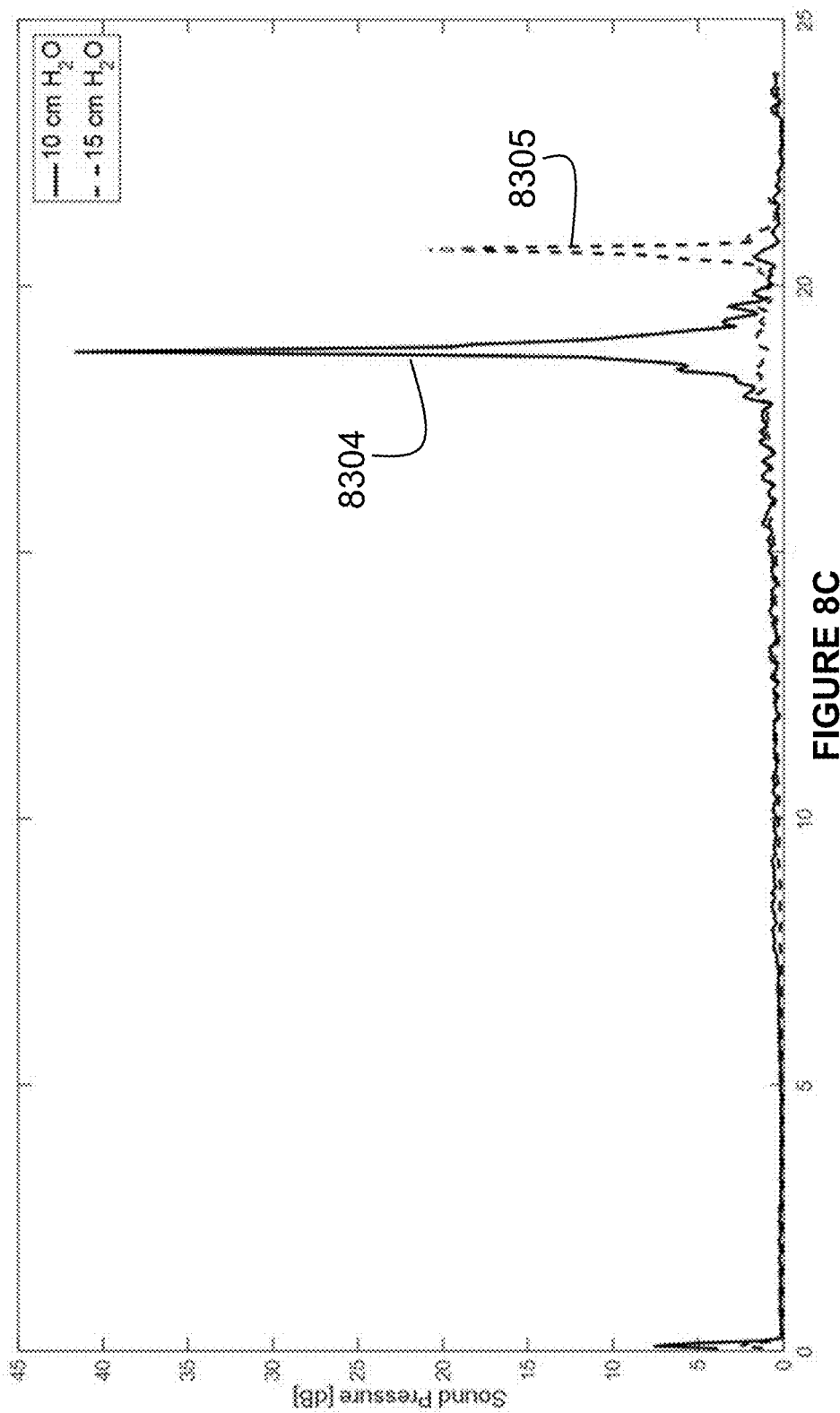

FIG. 8C shows a frequency spectrum of an acoustic signal generated by an acoustic generator in conjunction with an RPT system.

FIG. 9 is a flow chart illustrating example control process (es) that may be implemented in some versions of the present active acoustic analysis technology, such as using one or more processors of a respiratory therapy device, server and/or electronic processing device(s) (e.g., smart phone, smart speaker, tablet or laptop).

5 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

5.1 Therapy

In one form, the present technology comprises a method for treating a respiratory disorder comprising the step of applying positive pressure to the entrance of the airways of a patient 1000.

In certain examples of the present technology, a supply of air at positive pressure is provided to the nasal passages of the patient via one or both nares.

In certain examples of the present technology, mouth breathing is limited, restricted or prevented.

5.2 Therapy Systems

In one form, the present technology comprises a system for treating a respiratory disorder. The respiratory therapy (RT) system may comprise an RPT device 4000 for supplying pressurised air to the patient 1000 via an air circuit 4170 to a patient interface 3000.

5.3 Patient Interface

Figure 1A:
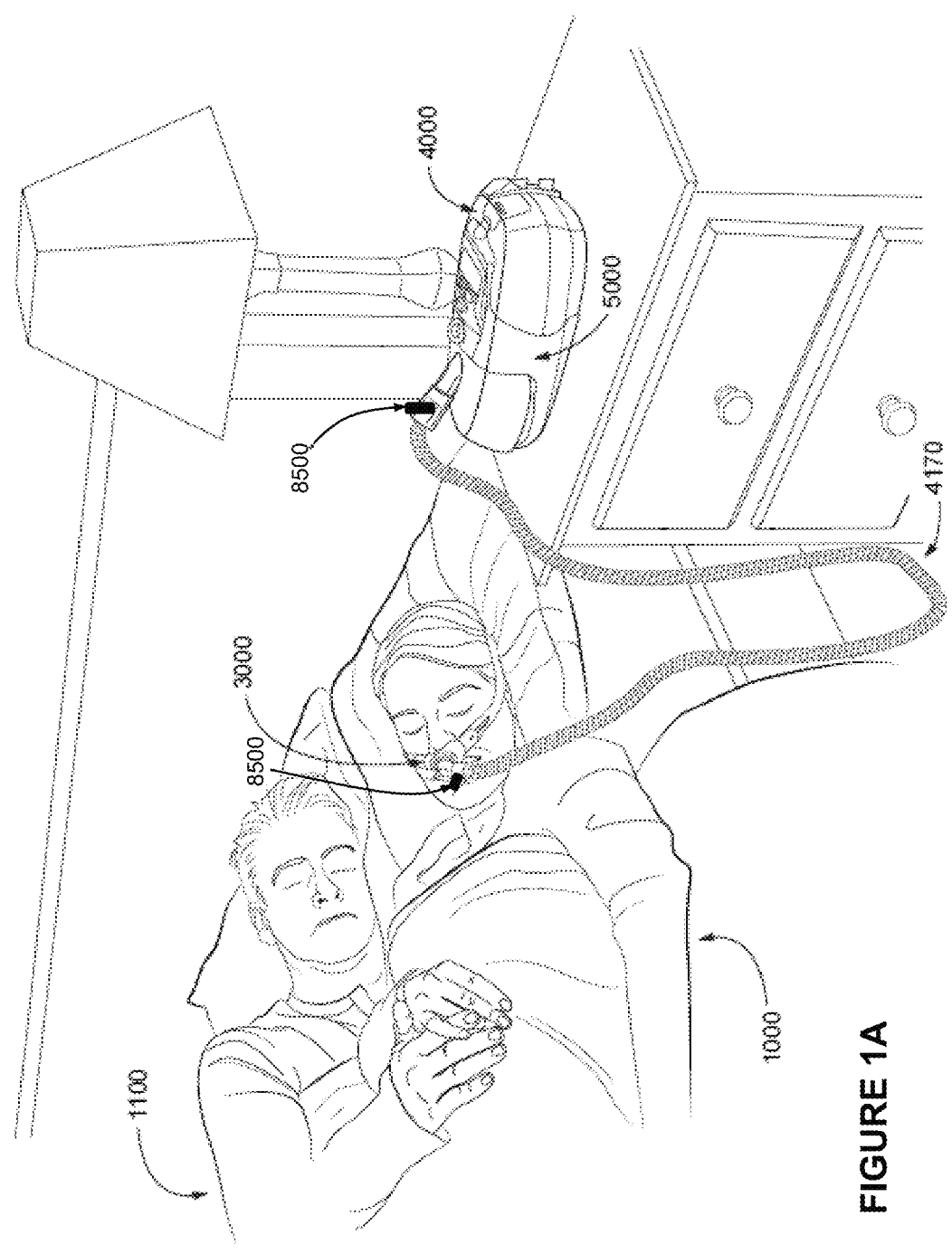
Figure 1B:
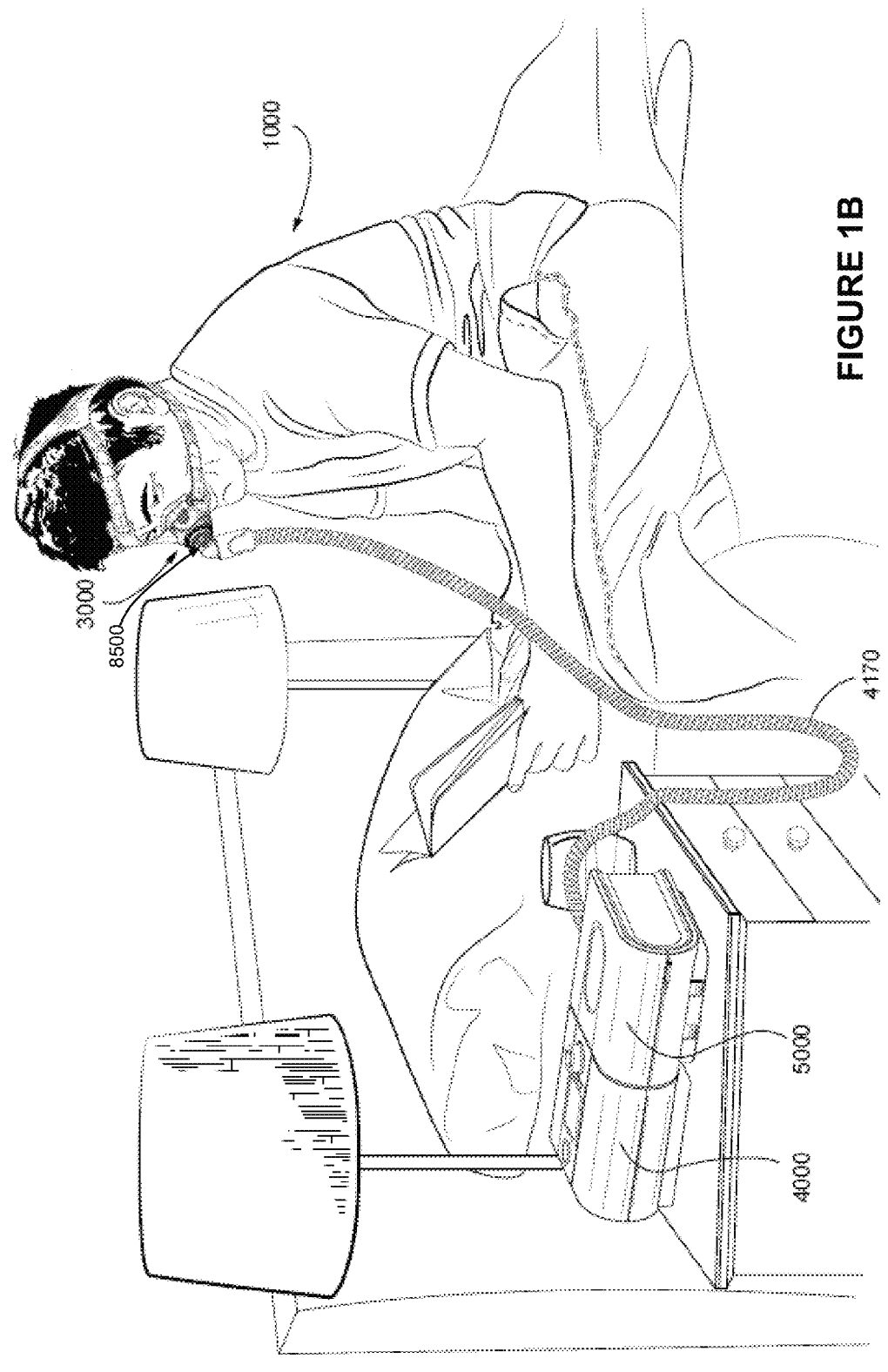
Figure 1C:
Figure 2:
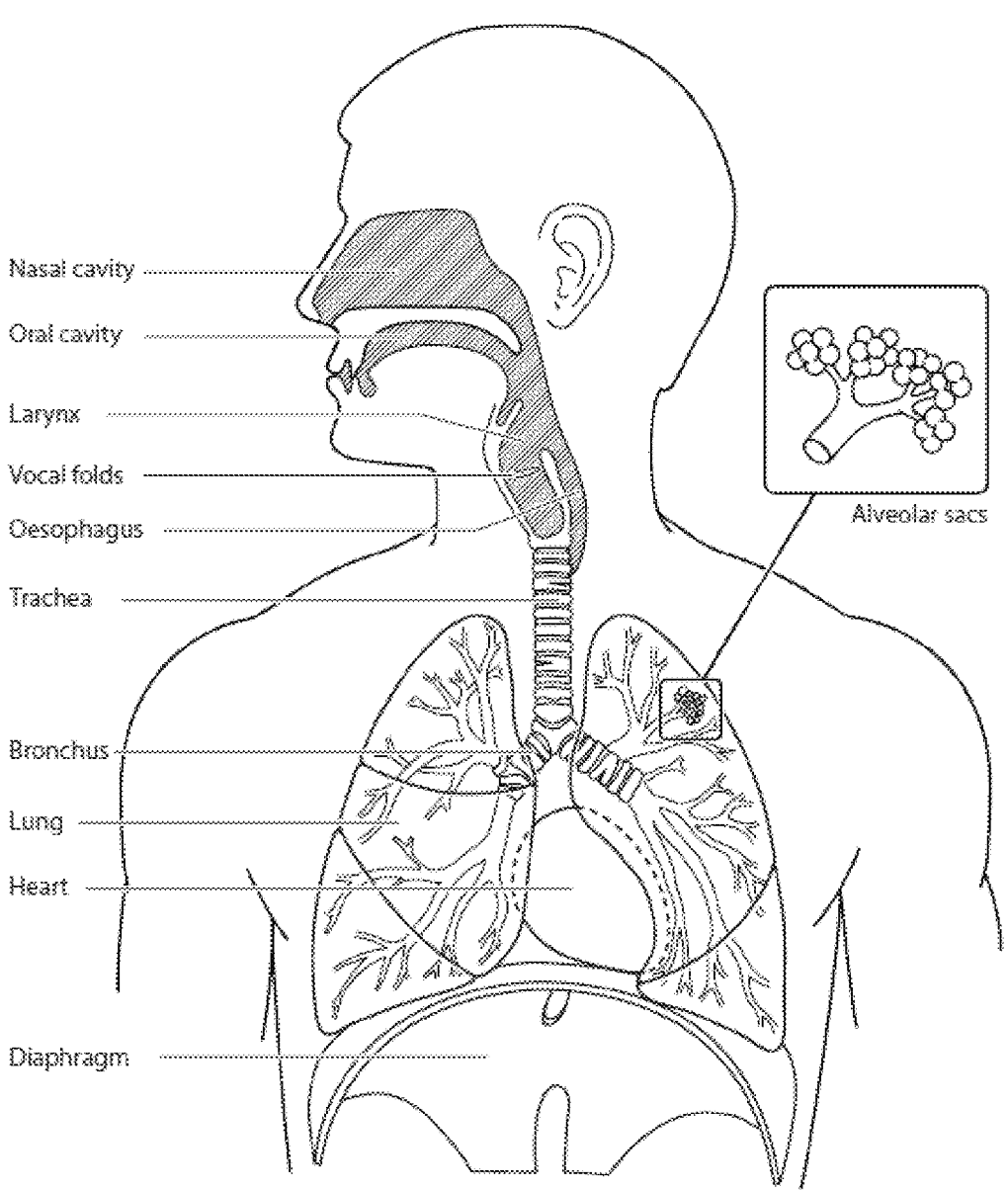
Figure 3:
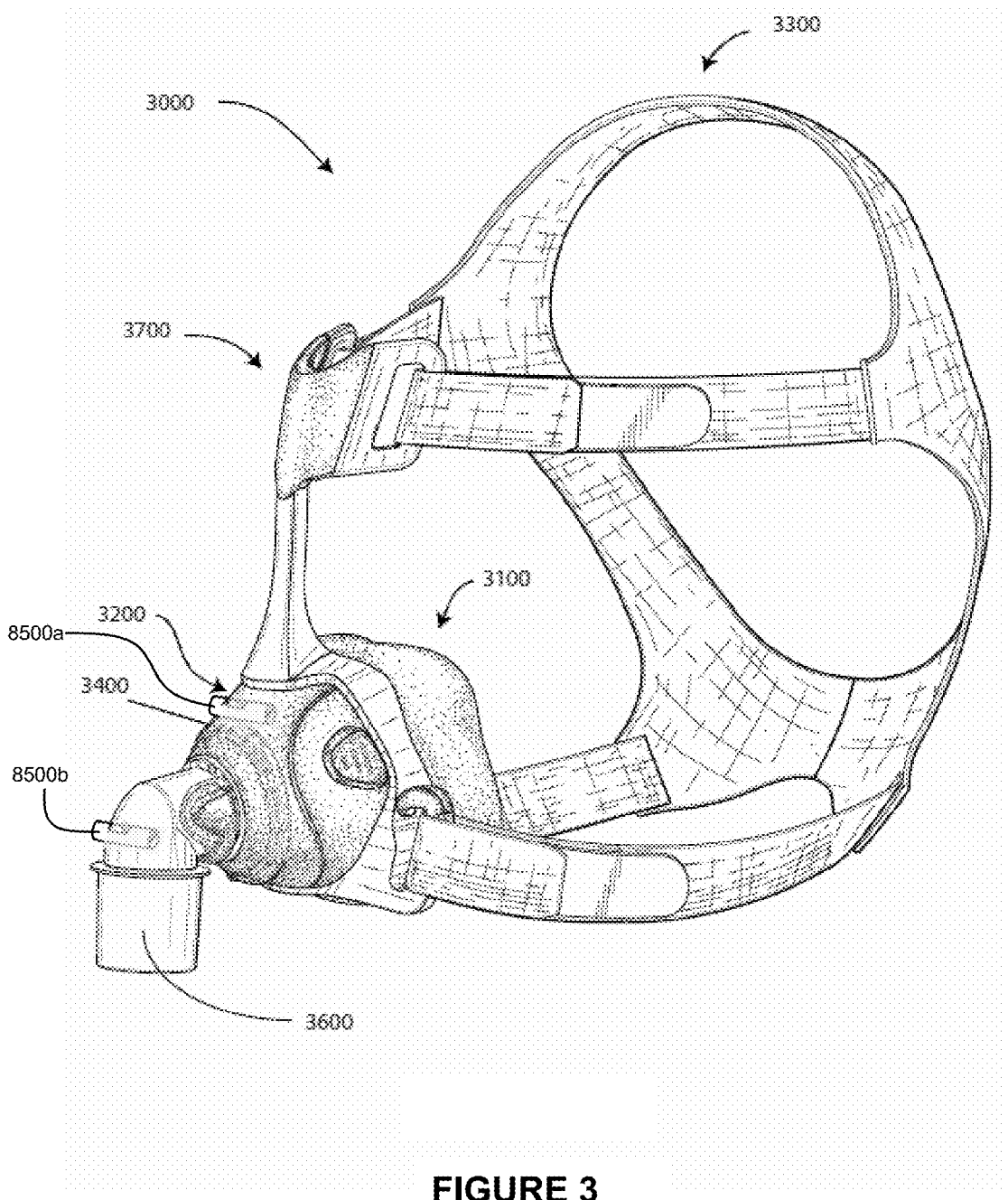

An example non-invasive patient interface 3000 is shown in FIG. 3 and comprises the following functional aspects: a seal-forming structure 3100, a plenum chamber 3200, a positioning and stabilising structure 3300, a vent 3400, one form of connection port 3600 for connection to air circuit 4170, and a forehead support 3700. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

The patient interface 3000 in accordance with one form of the present technology is constructed and arranged to be able to provide a supply of air at a positive pressure, such as of at least 4 cmH$_2$O, or at least 10cmH$_2$O, or at least 20 cmH$_2$O, or at least 25 cmH$_2$O with respect to ambient.

As illustrated in FIG. 3, the patient interface may be implemented with an acoustic generator 8500a or 8500b, such as an acoustic generator as described in more detail herein, located in or on the patient interface 3000, such as through a patient interface portion to the plenum chamber 3200, or on the connection port 3600. Thus, in some versions, the acoustic generator(s) may be arranged or otherwise adapted to couple to a gas path such as of the air circuit, or the RT device, so as to sample a portion of the gas of the path as discussed in more detail herein.

5.3.1 Seal-Forming Structure

In one form of the present technology, a seal-forming structure 3100 provides a target seal-forming surface region, and may additionally provide a cushioning function. The target seal-forming region is a region on the seal-forming structure 3100 where sealing may occur. The region where sealing actually occurs—the actual sealing surface—may change within a given treatment session, from day to day, and from patient to patient, depending on a range of factors including for example, where the patient interface was placed on the face, tension in the positioning and stabilising structure and the shape of a patient's face.

5.3.2 Plenum Chamber

The plenum chamber 3200 has a perimeter that is shaped to be complementary to the surface contour of the face of an average person in the region where a seal will form in use. In use, a marginal edge of the plenum chamber 3200 is positioned in close proximity to an adjacent surface of the face. Actual contact with the face is provided by the seal-forming structure 3100. The seal-forming structure 3100 may extend in use about the entire perimeter of the plenum chamber 3200. In some forms, the plenum chamber 3200 and the seal-forming structure 3100 are formed from a single homogeneous piece of material. An acoustic generator 8500 may be formed as a part of, or through a shell of, the plenum chamber 3200.

5.3.3 Positioning and Stabilising Structure

The seal-forming structure 3100 of the patient interface 3000 of the present technology may be held in sealing position in use by the positioning and stabilising structure 3300.

5.3.4 Vent

In one form, the patient interface 3000 includes a vent 3400 constructed and arranged to allow for the washout of exhaled gases, e.g. carbon dioxide.

In certain forms the vent 3400 is configured to allow a continuous vent flow from an interior of the plenum chamber 3200 to ambient whilst the pressure within the plenum chamber is positive with respect to ambient. The vent 3400 is configured such that the vent flow rate has a magnitude sufficient to reduce rebreathing of exhaled CO2 by the patient while maintaining the therapeutic pressure in the plenum chamber in use. One form of vent 3400 in accordance with the present technology comprises a plurality of holes, for example, about 20 to about 80 holes, or about 40 to about 60 holes, or about 45 to about 55 holes.

The vent 3400 may be located in the plenum chamber 3200. Alternatively, the vent 3400 is located in a decoupling structure, e.g., a swivel.

5.3.5 Connection Port

Connection port 3600 allows for connection to the air circuit 4170, and may optionally include an integrated acoustic generator 8500.

5.3.6 Anti-Asphyxia Valve

In one form, the patient interface 3000 includes an anti-asphyxia valve.

5.3.7 Ports

In one form of the present technology, a patient interface 3000 includes one or more ports that allow access to the volume within the plenum chamber 3200. In one form this allows a clinician to supply supplemental oxygen. In one form, this allows for the direct measurement of a property of gases within the plenum chamber 3200, such as the pressure. Such a port may couple to a conduit that leads to a transducer, such as a pressure sensor.

5.4 RPT Device

Figure 4A:
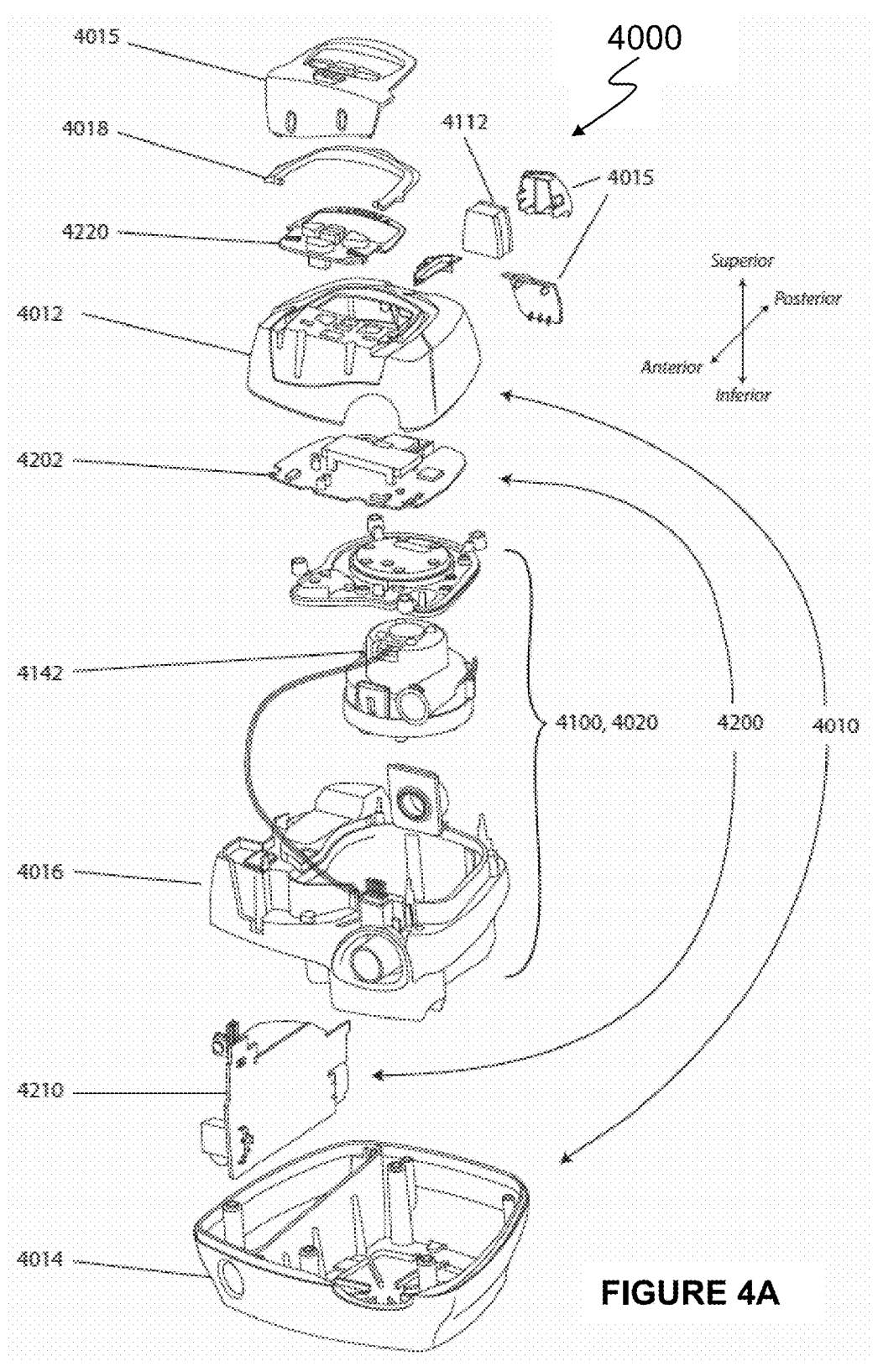
FIG. 4A shows an exploded view of an example respiratory pressure therapy (RPT) device 4000 in accordance with one form of the present technology.
Figure 4B:
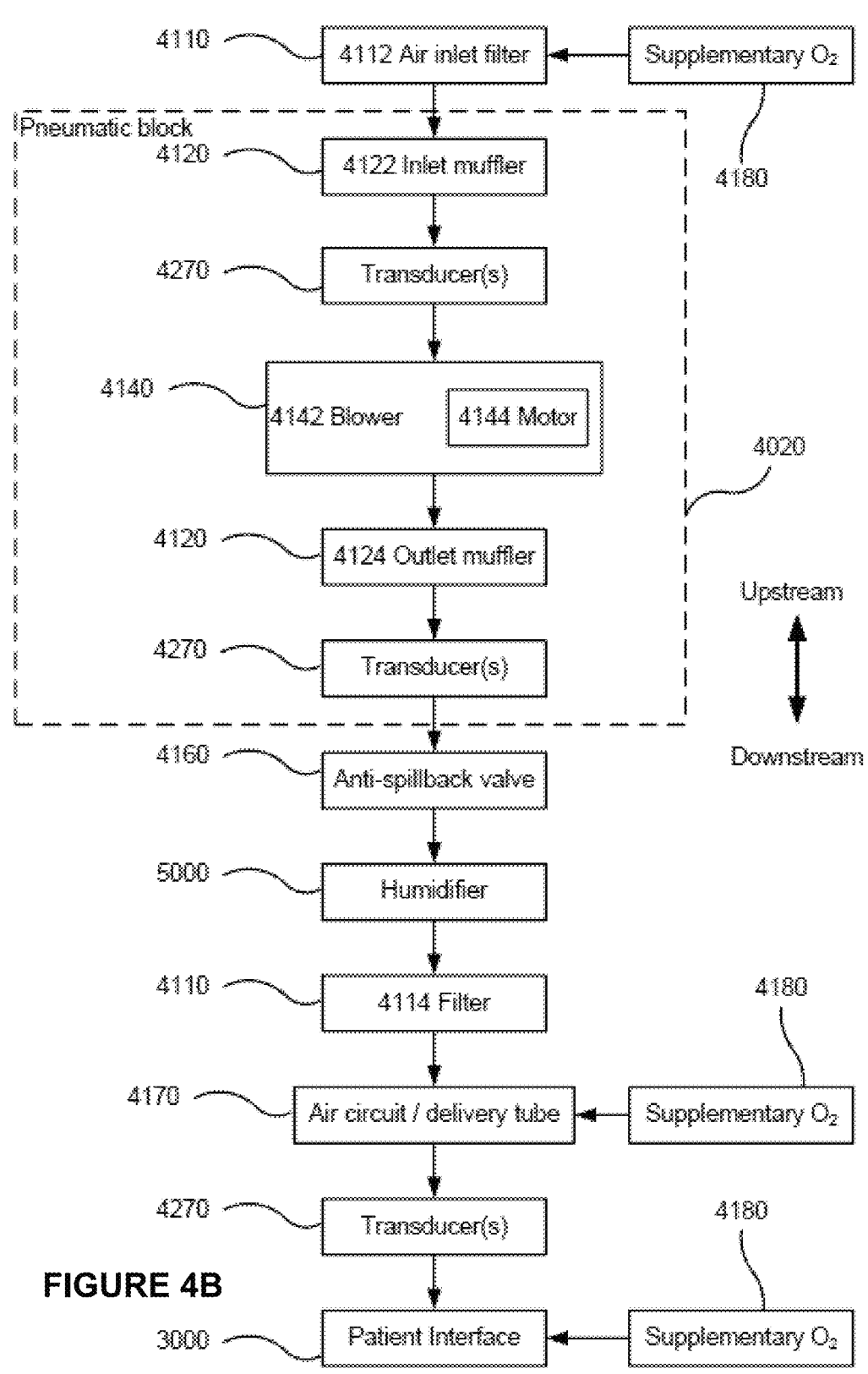
FIG. 4B is a schematic diagram of the pneumatic path of an RPT device in accordance with one form of the present technology. The directions of upstream and downstream are indicated.

A respiratory pressure therapy (RPT) device 4000 in accordance with one aspect of the present technology is shown in exploded view in FIG. 4A and comprises mechanical, pneumatic, and/or electrical components and is configured to execute one or more algorithms 4300. The RPT device 4000 may be configured to generate a flow of air for delivery to a patient's airways, such as to treat one or more of the respiratory conditions described elsewhere in the present document.

In one form, the RPT device 4000 is constructed and arranged to be capable of delivering a flow of air in a range of −20 L/min to +150 L/min while maintaining a positive pressure of at least 4 cmH$_2$O, or at least 10cmH$_2$O, or at least 20 cmH$_2$O, or at least 25 cmH$_2$O.

The RPT device may have an external housing 4010, formed in two parts, an upper portion 4012 and a lower portion 4014. Furthermore, the external housing 4010 may include one or more panel(s) 4015. The RPT device 4000 comprises a chassis 4016 that supports one or more internal components of the RPT device 4000. The RPT device 4000 may include a handle 4018.

The pneumatic path of the RPT device 4000 may comprise one or more air path items, e.g., an inlet air filter 4112, an inlet muffler 4122, a pressure generator 4140 capable of supplying air at positive pressure (e.g., a blower 4142), an outlet muffler 4124 and one or more transducers 4270, such as pressure sensors and flow rate sensors.

One or more of the air path items may be located within a removable unitary structure which will be referred to as a pneumatic block 4020. The pneumatic block 4020 may be located within the external housing 4010. In one form a pneumatic block 4020 is supported by, or formed as part of the chassis 4016.

The RPT device 4000 may have an electrical power supply 4210, one or more input devices 4220, a central controller 4230, a therapy device controller 4240, a pressure generator 4140, one or more protection circuits 4250, memory 4260, transducers 4270, data communication interface 4280 and one or more output devices 4290. Electrical components 4200 may be mounted on a single Printed Circuit Board Assembly (PCBA) 4202. In an alternative form, the RPT device 4000 may include more than one PCBA 4202.

5.4.1 RPT Device Mechanical & Pneumatic Components

An RPT device may comprise one or more of the following components in an integral unit. In an alternative form, one or more of the following components may be located as respective separate units.

5.4.1.1 Pressure Generator

In one form of the present technology, a pressure generator 4140 for producing a downstream air flow such as a flow, or a supply, of air at positive pressure is a controllable blower 4142. The blower may be capable of delivering a supply of air, for example at a rate of up to about 120 litres/minute, at a positive pressure in a range from about 4 cmH$_2$O to about 20 cmH$_2$O, or in other forms up to about 30 cmH$_2$O. The blower may be as described in any one of the following patents or patent applications the contents of which are incorporated herein by reference in their entirety: U.S. Pat. Nos. 7,866,944; 8,638,014; 8,636,479; and PCT Patent Application Publication No. WO 2013/020167.

The pressure generator 4140 is under the control of the therapy device controller 4240.

In other forms, a pressure generator 4140 may be a piston-driven pump, a pressure regulator connected to a high pressure source (e.g. compressed air reservoir), or a bellows.

5.4.1.2 Memory

In accordance with one form of the present technology the RPT device 4000 includes memory 4260, e.g., non-volatile memory. In some forms, memory 4260 may include battery powered static RAM. In some forms, memory 4260 may include volatile RAM.

Memory 4260 may be located on the PCBA 4202. Memory 4260 may be in the form of EEPROM, or NAND flash.

Additionally or alternatively, RPT device 4000 includes a removable form of memory 4260, for example a memory card made in accordance with the Secure Digital (SD) standard.

In one form of the present technology, the memory 4260 acts as a non-transitory computer readable storage medium on which is stored computer program instructions or processor control instructions expressing the one or more methodologies described herein, such as the one or more algorithms 4300.

5.4.1.3 Data Communication Systems

In one form of the present technology, a data communication interface 4280 is provided, and is connected to the central controller 4230. Data communication interface 4280 may be connectable to a remote external communication network 4282 and/or a local external communication network 4284. The remote external communication network 4282 may be connectable to a remote external device 4286. The local external communication network 4284 may be connectable to a local external device 4288.

In one form, data communication interface 4280 is part of the central controller 4230. In another form, data communication interface 4280 is separate from the central controller 4230, and may comprise an integrated circuit or a processor.

In one form, remote external communication network 4282 is the Internet. The data communication interface 4280 may use wired communication (e.g. via Ethernet, or optical fibre) or a wireless protocol (e.g. CDMA, GSM, LTE) to connect to the Internet.

In one form, local external communication network 4284 utilises one or more communication standards, such as Bluetooth, or a consumer infrared protocol.

In one form, remote external device 4286 is one or more computers, for example a cluster of networked computers. In one form, remote external device 4286 may be virtual computers, rather than physical computers. In either case, such a remote external device 4286 may be accessible to an appropriately authorised person such as a clinician.

The local external device 4288 may be a personal computer, mobile computing device such as a smartphone or tablet device, or a remote control.

5.4.2 RPT Device Algorithms

As mentioned above, in some forms of the present technology, the central controller 4230 may be configured to implement one or more algorithms 4300 expressed as computer programs stored in a non-transitory computer readable storage medium, such as memory 4260. The algorithms 4300 are generally grouped into groups referred to as modules.

5.5 Air Circuit

An air circuit 4170 in accordance with an aspect of the present technology is a conduit or a tube constructed and arranged to allow, in use, a flow of air to travel between two components such as RPT device 4000 and the patient interface 3000.

In particular, the air circuit 4170 may be in fluid connection with the outlet of the pneumatic block and the plenum chamber of the patient interface.

5.6 Transducer(s)

An RPT system may comprise one or more transducers (sensors) configured to measure one or more of any number of parameters in relation to an RPT system, its user and/or an environment. A transducer may be configured to produce an output signal representative of the one or more parameters that the transducer is configured to measure.

The output signal may be one or more of an electrical signal, a magnetic signal, a mechanical signal, a visual signal, an optical signal, an acoustic signal or any number of others which are known in the art.

A transducer may be integrated with another component of an RPT system, where one exemplary arrangement would be the transducer being internal of an RPT device. A transducer may be substantially a 'standalone' component of an RPT system, where an exemplary arrangement of which would be the transducer being external of the RPT device.

Transducers may be configured to communicate its output to one or more components of an RPT system, such as with an RPT device, a local external device, or a remote external device. External transducers may be for example located on a patient interface, or in an external computing device, such as a smartphone. External transducers may be located for example on or form part of the air circuit, e.g., the patient interface.

In some forms, a transducer may be configured to work in conjunction with another component of an RPT system, such as an acoustic generator, as will be discussed in further detail elsewhere in the present document. In such configurations, a subset of an RPT system, such as comprising an acoustic generator, and an acoustic sensor, may be referred to as a sensing system.

The one or more transducers 4270 may be constructed and arranged to generate signals representing properties of air such as a flow rate, a pressure or a temperature. The air may be a flow of air from the RPT device to a patient, a flow of air from the patient to the atmosphere, ambient air or any others. The signals may be representative of properties of the flow of air at a particular point, such as the flow of air in the flow path between the RPT device and the patient. In one form of the present technology, one or more transducers 4270 are located in a pneumatic path of the RPT device, such as upstream and/or downstream of the pressure generator 4140.

In another form of the present technology, a sensing system may comprise an acoustic generator located in the flow path, and an acoustic sensor configured to receive a signal from the acoustic generator.

In one form of the present technology, one or more transducers 4270 may be located proximate to the patient interface 3000.

In one form, a signal from a transducer 4270 may be filtered, such as by low-pass, high-pass or band-pass filtering.

5.6.1 Flow Rate Sensor

A flow rate sensor in accordance with the present technology may be based on a differential pressure transducer, for example, an SDP600 Series differential pressure transducer from SENSIRION.

In one form, a signal representing a flow rate from the flow rate sensor is received by the central controller 4230.

5.6.2 Pressure Sensor

A pressure sensor in accordance with the present technology is located in fluid communication with the flow path. An example of a suitable pressure sensor is a transducer from the HONEYWELL ASDX series. An alternative suitable pressure sensor is a transducer from the NPA Series from GENERAL ELECTRIC.

In one form, a signal from the pressure sensor is received by the central controller 4230.

5.7 Acoustic Sensing

According to one or more aspects of the present technology, acoustic analysis may be used to determine one or more parameters in relation to respiratory disorders, or systems for treatment of respiratory disorders, such as with or without the use of an acoustic generator described herein.

Acoustic analysis according to aspects of the present technology may have one or more advantages over the prior art, such as reducing cost of care, delivering higher quality of therapy, improving ease of use of a therapy system, reducing waste, and providing digital connectivity at a low cost.

As will be clear in the context of the remainder of the document, the terms 'acoustic', 'sound', or 'noise' in the present document are generally intended to include airborne vibrations, regardless of whether they may be audible or inaudible. As such, the terms 'acoustic', 'sound', or 'noise' in the present document are intended to include airborne vibrations in the ultrasonic, or subsonic ranges, unless specifically stated otherwise.

5.7.1 Passive Acoustic Sensing

In some forms, one or more parameters in relation to a patient, a therapy or a therapy system may be determined by detecting and analysing external sounds being emitted by the respiratory therapy system. Thus, an RT system may comprise one or more acoustic receivers, each acoustic receiver configured to detect sounds from one or more components of the respiratory therapy system.

For example, an acoustic receiver may be located in, on or around the respiratory pressure device (RPT) 4000 to detect sounds emitted by the RPT device 4000 and communicate a representative signal to a processor to determine one or more parameters therefrom 5.7.1.1 Acoustic Receiver An acoustic receiver may be adapted to receive acoustic signals (sounds) originating in the vicinity of the patient 1000 and/or the RPT device 4000. The acoustic receiver may be optimised for detection of acoustic signals of a predetermined frequency or frequency range, and for converting the detected acoustic signals into one or more electrical signals.

The acoustic receiver may be, for example, a microphone. In use, the microphone may be located in close proximity to the patient undergoing respiratory therapy and/or in close proximity to an RPT device 4000.

In particular arrangements, the acoustic receiver may be provided by a microphone comprised in a mobile computing device such as, for example, a smart phone, phablet or tablet device. In alternate arrangements, the RPT device 4000 may comprise an acoustic receiver, such as in a housing thereof, or external to a main housing comprising a pressure generator of the RPT device, such as in a second housing.

The acoustic receiver may be adapted to detect acoustic signals representative of the respiratory therapy in use (e.g. either: passive acoustic signals from the RPT device and/or the patient interface; or, active acoustic signals generated by an acoustic generator coupled to at least one component of the RT system).

In one example, the acoustic receiver may be configured to detect sounds in a typical audible range of a human being.

In another example, the acoustic receiver may be configured to detect sounds in frequencies in at least the 16-25 kHz range, and configured to produce signals (e.g. electrical) representative of the detected acoustic signal. The signals may be analysed (e.g. via a fast Fourier transform (FFT)) to obtain a frequency spectrum thereof, and determination of the dominant output frequency may then be correlated to determine a treatment pressure or flow rate. In such an example, an acoustic sensing system may comprise the acoustic receiver, and an acoustic generator configured to generate sounds in frequencies in at least the 16-25 kHz range.

5.7.1.2 Acoustic Analysis Processor

The acoustic receiver is, in particular arrangements, connected to an analysis module adapted to receive the electrical signals generated by the acoustic receiver and perform analyses on the received electrical signals. The analysis module may comprise an acoustic analysis processor.

The acoustic analysis processor may form a part of the RPT device 4000, for example as a discrete processor, or a controller of the RPT device (e.g. the central controller) may be configured to perform as the acoustic analysis processor. In particular arrangements, the acoustic receiver and acoustic analysis processor may be located externally to an RPT device 4000, such as in a mobile computing device such as, for example, a mobile phone, phablet, or tablet computing device.

Acoustic analyses may be carried out to determine one or more of: a sound pressure level, variations in sound pressure level, a baseline sound pressure level over a predetermined length of time, and frequency components included in the detected acoustic signal.

To carry out the acoustic analysis/analyses, the acoustic analysis processor may execute an acoustic analysis software application installed in a memory. The acoustic analysis software application may include computer-readable instructions (code) adapted for receiving an electrical signal generated by the acoustic receiver in response to acoustic signals in the vicinity of the mobile computing device. The acoustic analysis software application may also include computer-readable instructions (code) adapted for determining the operational parameters for the treatment in use of a respiratory disorder in a patient, and correlating such operational parameters with one or more of the determined operational parameters in accordance with requirements. For example, depending on the analysis of sound from the acoustic analysis processor, pressure control or flow control parameters (e.g., control settings) may be set or adjusted so as to change or control treatment produced with the patient interface. In such examples, the acoustic analysis processor may output one or more input signals for a pressure and/or flow control loop of the system.

5.7.1.3 Passive Acoustic Monitoring and Analysis

In particular arrangements, the acoustic receiver is adapted to measure ambient acoustic signals (e.g. sounds in the vicinity of the acoustic receiver which are not directly related to the treatment of a respiratory disorder in the patient) and/or treatment acoustic signals (e.g. sounds in the vicinity of the acoustic receiver which are directly or indirectly related to the treatment of a respiratory disorder in the patient). Acoustic analyses may identify one or more events captured in the detected sounds.

Examples of events captured in ambient acoustic signals which may be measured by an acoustic receiver and identified by an acoustic analysis may include: patient snore, patient respiratory rate, patient respiratory effort, traffic in the vicinity of the patient receiving the respiratory therapy, motion of the patient's bed sheets (e.g. from rustling) which may be indicative of restlessness in the patient, speech (usually being indicative of the patient being in a wakeful state), animal/pet sounds (e.g. a dog barking), respiratory events (e.g. coughing, wheezing or crackling sounds being made by the patient), and others including, but not being limited to administration of a respiratory support medication (e.g. Ventolin™ Puffer or nasal spray), or a pill packet being opened by the patient.

Detection of such ambient sounds may, in particular arrangements, allow events identified therein to be added to a sleep diary which may be used to inform the patient or their medical practitioner of the patient's sleep habits and determine possible risk factors (e.g. screening and monitoring of the patient for a respiratory and/or sleep disorder such as, for example, insomnia). In particular, summary statistics such as the Apnea Hypopnea Index (AHI) indicative of severity of obstructive sleep apnea may be computed from the identified events. This may be useful in prescribing a particular respiratory and/or sleep treatment to the patient, e.g. CPAP treatment methods where the patient is at a risk of having obstructive sleep apnea, or sleep scheduling treatment methods such as for insomnia.

Conventional monitoring of respiratory pressure therapy relies on measurements of pressure and flow rate from transducers 4270 at the RPT device 4000. The patient's respiratory flow rate waveform may be estimated from these measurements in a known manner. Events such as apneas, hypopneas, respiratory effort-related arousals (RERAs), snores, etc. may be identified in the respiratory flow rate waveform, and summary statistics such as the AHI may be computed from the identified events. In one implementation, such statistics are computed according to known methods while the patient 1000 is using the respiratory pressure therapy, and compared with statistics computed according to the described passive acoustic monitoring methods when the patient is not using the respiratory pressure therapy. The results of such a comparison (e.g. an AHI of 40 being reduced to less than 5 by the therapy) may be used to demonstrate to the patient the benefits of the respiratory therapy.

As an example of passive acoustic monitoring of a patient undergoing a CPAP treatment for a respiratory disorder, FIGS. 6A and 6B show graphs of measured sound power levels emitted by a RPT device 4000 (in the present example the RPT device 4000 is an S9 Series CPAP flow generator available from ResMed™ Limited) and a CPAP-suitable patient interface 3000. The acoustic signal was detected with the microphone of a mobile computing device (i.e. smartphone). Respectively, FIGS. 6A and 6B show the increase in the sound power level (in dBA) of acoustic noise from the RPT device 4000 and/or the patient interface 3000 due to increasing treatment pressure and air flow rate respectively.

As a pressure or air flow rate generated by the RPT device 4000 increases, typically the sound power generated by the RPT device 4000 and/or the patient interface 3000 increases proportionally. This effect can be seen in FIGS. 6A and 6B, as an example. Such increases may be a result of one or more of an increased rotational speed of a blower 4142, increased flow rate through a vent 3400, and an increased flow rate through the RPT system, as well as other effects associated with an increased pressure and/or flow rate.

As a corollary, the pressure and/or the air flow rate may be estimated by the measured sound of the RPT device 4000 and/or the patient interface 3000 alone (treatment acoustic signals). This may be beneficially applied to design of a RPT device 4000, since a suitable acoustic receiver and acoustic processor may perform one or more functions of the pressure and/or air flow rate sensors normally included with an RPT device 4000. This may thus reduce a cost of the RPT device and also reduce complexity of the control circuitry and processing algorithms of the RPT device, whilst still providing control and feedback data for provision of an effective respiratory therapy.

Furthermore, passive monitoring of treatment acoustic signals generated by the RPT system (e.g. by RPT device 4000 and/or patient interface 3000) can be adapted for monitoring of further mechanical parameters associated with respiratory therapy. For example, a resonance at a particular frequency may be correlated to one or more mechanical components of the RPT device 4000 such as, for example, the shaft speed of the drive shaft driving the impeller of the RPT device blower 4142, or alternatively one or more harmonic ratios of the shaft speed resonance may be correlated to one or more mechanical features of the drive components of the blower 4142 such as, for example, bearing tones, shaft misalignment, impeller blade pass frequency, or cogging among many others as would be appreciated by the skilled addressee.

In some examples of the present technology, one or more parameters such as air flow rate, air pressure, or other operational parameters may be determined based on information determined from the passive monitoring of treatment acoustic signals generated by the RT system. For example, acoustic analysis may determine a rotational speed of the blower, which, in conjunction with a fan curve may be used to determine a pressure of the flow of air, such as at an outlet of the RPT device.

In another example, FIG. 6C shows a time-based trace of a microphone signal 8101 and an RPT device signal 8102 (showing leak) as determined by an RPT device with a differential pressure flow rate sensor and a pressure sensor. FIG. 6C shows that when increased leak is reported by the RPT device signal 8102 (where the leak indication suddenly increases), the microphone signal 8101 reports a corresponding increase. Thus, the inventors have advantageously put into practice an acoustic analysis algorithm configured to carry out leak monitoring based on acoustic signals generated by the RPT system.

In a yet another example, FIG. 6D shows another time-based trace of a microphone signal 8201 and an RPT device signal 8202 (showing flow rate) as determined by an RPT device comprising a differential pressure flow rate sensor. FIG. 6D also shows a strong correlation between the two signals, allowing derivation of parameters such as respiratory rate.

It will be understood that any other information derived or measured from one or more transducers associated with the RT system may be used in addition to, or instead of, a fan curve, in conjunction with outputs from acoustic analyses of the passive monitoring of acoustic signals.

5.7.2 Acoustic Generator

FIG. 7A shows an acoustic generator suitable for the systems and methods disclosed herein. A single such acoustic generator can be implemented to serve as a pressure sensor and/or a flow rate sensor. In some versions, several such acoustic generators, such as two working in concert as discussed in more detail herein, can also serve as a differential flow rate sensor or differential pressure sensor.

The acoustic generator is configured to sample or receive a gas flow or downstream air flow produced by a pressure source or pressure generator of an RPT device, and provide a signal representative of one or more characteristics (e.g. the pressure or flow rate) of the gas flow or the downstream air flow. Thus, the acoustic generator can generate the signal so as to provide it as a measure of the gas characteristic(s). The acoustic generator may be configured to generate the signal as an acoustic signal substantially inaudible to human hearing (e.g., limit its production of sound to an inaudible sound frequency range), that is yet detectable by an acoustic receiver, thus allowing communication via the acoustic signal without disturbing those nearby. Moreover, depending on the desired implementation, it may be configured to generate this inaudible signal so that the signal can proportionally represent variations in the gas characteristics in an expected range (e.g., a therapy range), such that the changing gas characteristic(s) remains within the detectable inaudible frequency range. Such configurations may be beneficial for use in or with an RPT system, which may be placed close to a user/patient, sometimes bedside, and/or used during sleep.

For example, if an expected treatment pressure range of therapy during use typically varies between a range of 4 to 18 cmH$_2$O, or 4 to 25 or 4 to 20, etc., the acoustic generator may be configured to maintain its output signal within an inaudible frequency range as the sampled gas characteristic varies across this expected or predetermined therapy pressure range. Thus, the acoustic generator may remain inaudible as desired during a sleep therapy session. Moreover, such a configuration may also be implemented so as to maintain the output within an inaudible frequency range that is readily detectable across the desired range by typical microphones (e.g., a typical smart phone microphone). Configuring the acoustic generator to do so, such as in relation to the examples of the present technology, may be accomplished by selection of suitable design characteristics (e.g., design parameters), such as those illustrated and discussed herein in reference to, for example, FIGS. 7A to 7F.

Thus, the acoustic generator may be configured to produce a sound or acoustic signal at a frequency inaudible to humans, such as in an 'ultrasonic' range.

A frequency range of over 20 kHz is generally cited to be 'ultrasonic', and thus inaudible to humans. In practice, however, due to natural degradation of the frequency response of a person's hearing as they age, in practice the highest audible frequency can often be as low as about 16-18 kHz for most people, especially the elderly.

Additionally, acoustic signals at higher ends of audible frequency ranges are typically highly attenuated. This is demonstrated by the 'A-weighting curve', which is a standard weighting curve defined in International standard IEC 61672:2003 and designed to represent a sensitivity of the ear to different frequencies. According to A-weighting, sounds at 20 kHz are perceived 9.3 dB lower than a sound at 1 kHz, and sounds at 16 kHz are perceived 6.6 dB lower than a sound at 1 kHz. These are extremely significant attenuations when considering the fact that dB scales are logarithmic. Thus, low-amplitude acoustic signals having an amplitude less than typical hearing capabilities of the patient may also be advantageously utilised, as they may be still detectible by an acoustic receiver.

In one example, an acoustic generator may be configured to generate an acoustic signal in a frequency range between about 16 kHz and about 25 kHz. The acoustic generator may be configured to vary a characteristic of its output as a function of an air flow rate. In some forms, the acoustic generator may deliver an acoustic signal at a resonant frequency, where the frequency is a function of the flow rate of air travelling therethrough. The flow rates for which the acoustic resonance is optimised may correlate to typical treatment pressures for continuous positive airway pressure (CPAP) treatment systems such as in the range of between about 4 cmH$_2$O and about 25 cmH$_2$O.

FIG. 7A shows a schematic view of an example acoustic generator 8500 configured as a transducer for generating an acoustic signal in accordance with the systems and methods disclosed herein. FIGS. 7B and 7C show cross sectional views of acoustic generator 8500 taken alone dotted line A-A of FIG. 7A. The gas enters the narrow air channel or windway 8510 though windway inlet 8511 and travels towards the windway outlet 8512 which is in fluid communication with a vortex outlet 8520 and a resonance chamber or bore 8540. A blade formation 8530 having a blade leading edge 8531 is located within the vortex outlet 8520. Air flow exiting windway outlet 8512 moves above and below the blade formation 8530 causing the blade leading edge 8531 to oscillate, thus generating an acoustic signal by generation of vortices within the vortex outlet 8520. The portion of the air flow which moves below the blade formation 8530 enters acoustic chamber or bore 8540.

The frequency and intensity of the acoustic signal emitted by the acoustic generator 8500 depend on the direction and speed of the gas flow. In use, air enters windway inlet 8511 and flows through the windway 8510 and the resistance that is present from the slower air in between the windway outlet 8512 and blade formation 8530 generates vortices that cause the flow exiting the windway 8510 to oscillate. Repetitive vortex shedding takes place on alternative sides of the air flow and a tone is produced when a sharp edge (such as the leading edge 8531 of the blade formation 8530) separates the vortices. This oscillation sustains the tone and the frequency is proportional to the airstream velocity exiting the windway 8510 and inversely proportional to the distance between the windway outlet 8512 and the leading edge 8531 of the blade formation 8530. The remaining body of the whistle comprising an acoustic chamber or bore 8540 has a pipe resonance depending on the bore length. Bore 8540 terminates in a bore outlet 8541 in fluid communication with ambient air. The horn-like end 8542 of the bore 8540 raises the resonant frequency of the system. Long waves (low frequency oscillations) are not able to follow the curvature of the horn of the horn region 8542 and are reflected earlier than shorter waves, thereby causing a back-pressure feedback mechanism to the oscillation of the blade formation 8530. The shorter oscillations rapidly escape to atmosphere and longer waves see a shorter pipe in order to accommodate for this. Therefore, the horn like end (horn region 8542) shortens the effective length of the bore 8540 and allows for higher frequency tones to be observed. The horn like end (horn region 8542) of bore 8540 also helps with a gradual impedance matching of the air flowing from inside the acoustic generator (at higher pressures) to atmosphere. Thus the edge-tone produced by oscillation of the blade formation 8530 and vortex shedding is modulated by the back pressure produced by the bore chamber 8540.

Thus in use, in determining a gas pressure or flow rate of a gas in communication with the windway inlet 8511, the frequency spectrum of the acoustic signal generated by the acoustic generator typically comprises a dominant spectral frequency component dependent on the edge tone produced by oscillations of the blade formation 8530, the centre frequency of which is modulated by the free-spectral range of the bore 8540, such that as the pressure or air flow rate increases, the dominant frequency of the acoustic signal generated increases within the free-spectral range of the bore 8540 (see FIG. 8A). When the edge-tone frequency increases beyond the free-spectral range of the bore 8540, the dominant spectral frequency component of the generated acoustic signal experiences a mode hop to match the back-pressure modulation from the bore chamber 8540. Such mode hops 8303 in the spectral components (e.g. dominant sound frequency 8302) of the acoustic signal are evident in FIG. 8B.

FIG. 7D shows a portion of an example of a patient interface 3000 including an acoustic generator 8500 in a tapped configuration. In this particular implementation, acoustic generator 8500 is located such that a first end 8501 comprising the windway inlet 8511 of the acoustic generator 8500 is placed in fluid communication with the plenum chamber 3200 of patient interface 3000 (see acoustic generator 8500a in FIG. 3). Accordingly, a second end 8502 comprising the horn of the horn region 8542 of acoustic generator 8500 is in fluid communication with ambient air at ambient air pressure. In this configuration, the acoustic generator is configured to sample the gas pressure within plenum chamber 3200 of patient interface 3000 and to generate an acoustic signal dependent upon the gas pressure within the plenum chamber. Such a tapped configuration is also illustrated in FIG. 711 showing the windway inlet 8511 in fluid communication with a flow path 8800 that conducts a respiratory gas such as for a respiratory therapy. The flow path 8800 may be in a conduit, such as a portion of a patient circuit, or a portion of a patient interface. The outlet (e.g., bore outlet 8541) is outside the flow path (such as being located at ambient or environmental air) such as by passing across or through a wall boundary 8810 of the flow path.

In an alternate arrangement, the acoustic generator 8500 may be adapted to be inserted in-line with (e.g., within) a patient air circuit 4170. An example of such an in-line configuration is illustrated in FIG. 7G. For example, a downstream lateral flow following along a flow path 8800 in the air circuit (e.g., in a direction toward a patient interface) may be directed (e.g., laterally) to enter into the inlet of the acoustic generator's windway (windway inlet 8511), such as in a less tortuous path (e.g., by avoiding a substantial change in flow direction from the flow path direction and into the windway inlet). Such a configuration can reduce flow directional change to more readily permit the flow of the flow path to enter into the windway inlet. In an in-line case, the bore outlet and/or the vortex outlet of the acoustic generator may also be within the flow path of the patient circuit. Thus, the pressures at both ends of the acoustic generator (inlet end and outlet end) may generally correspond to the pressures in the patient circuit flow path. This can more readily permit the signal of the acoustic generator to correspond with the flow rate of the moving gas within the patient circuit. Thus, in an example, a connector module (not shown in FIG. 7D)

connectible to an RPT device 4000 and/or a patient interface 3000 may comprise an acoustic generator such that first end 8501 comprising the windway inlet 8511 of the acoustic generator 8500 is placed in fluid communication with a flow of air (e.g., "FLOW" in the flow path 8800 illustrated in FIG. 7G) generated by RPT device 4000, such as in the air circuit 4170. In this arrangement the acoustic generator is configured to sample the flow of air in air circuit 4170 and to generate an acoustic signal dependent upon the flow rate of air in the air circuit 4170. In particular arrangements, the acoustic generator is inserted in a connector module comprising an elbow module adapted to be connected between a distal end of air circuit 4170 and an air inlet port of patient interface 3000 (see acoustic generator 8500*b* in FIG. 3).

FIGS. 7E and 7F show an alternate configuration of an acoustic generator 8600 suitable for implementation in acoustic analysis of respiratory pressure therapy systems where like reference signs indicate like features. In this example of acoustic generator 8600, the blade formation 8630 is configured to provide a smooth transition from blade leading edge 8631 to the second end 8602 of the acoustic generator which smoothly transitions into horn region 8642.

This particular example acoustic generator is designed similarly to an aerofoil so as to minimise flow detachment which results in turbulent noise, thereby reducing generation of unwanted noise which may be audible.

The dimensions of the various component features of the acoustic generator 8500/8600 are responsible for determining the dominant acoustic signal output by the generator in use. Thus, strict control of the dimensional parameters of the acoustic generator are necessary to ensure that the dominant acoustic output frequency of the acoustic signal generated by the acoustic generator remains in the frequency range that is both inaudible to humans (so as not to disturb the sleep of a patient undergoing respiratory therapy in the vicinity of an acoustic generator as disclosed herein) and detectable by the acoustic receiver.

In one form, the dominant frequency output would be in the range of between about 20 kHz and about 25 kHz, to be outside the normal range of human hearing but still within the detectable range of typical acoustic receiver microphones. However, as noted above, an acoustic signal above a frequency of about 16 kHz is likely to be inaudible to human ears, especially for the elderly. Design of the acoustic generator also needs to consider other output frequencies which may be generated in addition to the dominant resonance frequency. Typically, an acoustic generator of the whistle type shown in FIG. 7A will also emit sound at a variety of other frequencies, some of which may be in the audible frequency range and thus undesirable when a patient is undergoing RPT (e.g. CPAP) treatment, typically while asleep. Any additional sounds in the audible frequency range may disturb the patient and thus impede the effectiveness of the respiratory therapy and will likely negatively impact the patient's compliance with the respiratory therapy.

In some implementations, as mentioned above, multiple acoustic generators may be located in fluid communication with the downstream air flow of a respiratory therapy and may be implemented to work in concert. The characteristics of the acoustic generators may be matched such that the respective generated inaudible acoustic signals have substantially equal acoustic frequencies in response to a given flow rate or pressure of the downstream air flow. In one implementation, a first acoustic generator may be located adjacent to or in the patient interface, while a second acoustic generator may be located adjacent the air outlet of the pressure generator. Optionally, the inlets of the acoustic generators may be within the flow path of the respiratory therapy while the outlets of the acoustic generators may be outside that flow path (e.g., at ambient pressure). Alternatively, both acoustic generators may be more completely within the flow path. In such implementations with matched acoustic generators, the acoustic signals generated by the first acoustic generator and the second acoustic generator interact to produce a combined acoustic "beat" signal whose amplitude modulates at a "beat" frequency representative of the difference in frequency between the two acoustic signals and therefore representative of a difference in flow rate or pressure between the downstream air flow exiting the air outlet of the pressure generator and/or the downstream air flow being delivered to the patient interface. The "beat" signal may be demodulated by the acoustic analysis processor to obtain the difference in flow rate or pressure.

In another implementation, a first acoustic generator may be separated by a small distance from a second acoustic generator along the air circuit. The "beat" frequency of the combined acoustic signal represents the difference in pressure between the two locations and therefore the flow rate of the air between the two locations.

Typical design parameters for an acoustic generator of the form shown in FIG. 7A (with reference to lengths as indicated in FIG. 7B) include:

length, $l_w$, of the windway 8510 between about 5 mm and about 7 mm;

width, w, of the windway 8510 and windway inlet 8511 and outlet 8512 between about 0.7 mm and about 1.5 mm;

height, h, of the windway 8510 and windway inlet 8511 and outlet 8512 between about 0.6 mm and about 0.7 mm;

length, $l_h$, of horn region 8542 between about 2 mm and about 4.45 mm;

radius of curvature of the horn region 8542 between about 2 degrees and about 8.5 degrees. In the horn region 8542, increasing the curvature will mean long waves will find it more and more difficult to follow and thus will see a shorter and shorter pipe. Therefore, increasing the curvature will have the effect of increasing the dominant frequency further in conjunction with the dimensions of the acoustic generator in other regions as noted above. The lower limit of the arc radius will generally be the length of horn region 8542 and it should transition smoothly to the horn from the bore region 8540 to avoid adding unwanted turbulent noise having a broad frequency spectrum which will likely be in the undesirable audible frequency range.

distance between the windway outlet 8512 and the leading edge 8531 of blade formation 8530 between 0.5 mm and about 2 mm;

Blade angle between about 25 degrees and about 50 degrees, preferably between about 25 degrees and about 35 degrees, typically about 30 degrees;

entire whistle length, L, less than about 15 mm;

length, $l_b$, of the non-horn section of the acoustic chamber (bore 8540) (i.e. not including the horn region 8542) between about 1 mm and about 3.2 mm.

Since such an acoustic generator is a component that does not require electrical power, it has advantages over traditional transducers since it needs no electrical connections or even communication lines. Such a component also has cost advantages relative to traditional transducers. It may be easier to manufacture as it does not require multiple discrete component parts typical of traditional transducers.

5.7.3 Active Acoustic Monitoring and Analysis

FIG. 8A shows a 2-dimensional waterfall chart (representing three axes of data) of the frequency output spectrum detected in an acoustic signal generated by an acoustic generator in conjunction with an RPT system with increasing treatment pressure. The brightness of the plot indicates an amplitude, along with time in the horizontal axis and frequency in the vertical axis.

In this present example, a mobile computing device (in the present example an iPhone™ Model 5S from Apple™ Inc. was used, however smartphones from other corporations such as, for example, Samsung, HTC™ or the like could also be used) was placed near to CPAP test system comprising an RPT device coupled to a patient interface to simulate an actual treatment mode of operation. An acoustic generator of the type shown in FIG. 7A was incorporated into the plenum chamber of the patient interface. The RPT device was programmed to generate an increasing treatment pressure to the patient interface of between 4 cmH$_2$O and about 20 cmH$_2$O over a time period of 4 minutes. The dominant output frequency 8301 can clearly be seen to turn on at about 16 kHz at a treatment pressure of approximately 7-8 cmH$_2$O and increase linearly with increasing treatment pressure applied to the patient interface to a final pressure of about 16 cmH$_2$O after 4 minutes.

FIG. 8B shows the frequency response of a differently configured acoustic generator having different design characteristics to the acoustic generator used to produce the acoustic signal shown in FIG. 8A. FIG. 8B shows a simplified waterfall plot, indicating only a peak (i.e. resonant) frequency.

In this case, the acoustic generator provides a dominant spectral component responsive to the applied treatment pressure over the full range of typical treatment pressures between about 4 cmH$_2$O and about 18 cmH$_2$O. As indicated above, the configuration of the particular acoustic generator used to obtain the frequency response spectrum of FIG. 8B exhibits a series of mode hops 8303 in the spectral dominant frequency of the acoustic output signal.

Despite presence of such mode hops, the acoustic analysis module may be configured to correlate the dominant output frequency with a provided treatment pressure with the addition of one or more secondary factors in the detected acoustic signal. For example, the sound intensity output by the acoustic generator may be unique for each of the modes seen across the operating frequency range. Other secondary factors in the detected acoustic signal may include one or more of: the slope of the dominant frequency output of each individual mode as the pressure or flow rate increases; and the shape and/or width of the peaks in the frequency spectrum of the acoustic output signal.

Thus, in determining a pressure or flow rate (such as a treatment pressure or treatment flow rate) from the inaudible acoustic signal generated by the acoustic generator, the acoustic analysis module may evaluate frequency, or dominant frequency, of the received acoustic signal and, optionally, also evaluate one or more secondary factor(s) that may be derived from the acoustic signal, such that the frequency and optional secondary factors(s) correlate with a pressure or flow rate value. For example, the determined frequency (and optional secondary factor(s)) may serve as an index or access information for accessing a look-up table of pressure values or flow rate values, such as in a memory, so that a pressure value or flow rate value that is correlated with the look-up information may be selected. Other methods of associating the values and the access information (e.g., frequency, or frequency and secondary factor(s)) may also be implemented. Such values may be determined experimentally or by a suitable conversion formula/relationship.

FIG. 8C is a graph of the spectrum of the detected acoustic signal at treatment pressures of 10 cmH$_2$O 8304 and at 15 cmH$_2$O 8305 clearly indicating the shift in the dominant frequency tone generated by the acoustic generator at different pressures, and showing that a measurement of a dominant frequency may be correlated to a pressure of the RPT system.

From the frequency spectrum shown in FIG. 8A it is clear that the acoustic generator is capable of replacing a traditional pressure or flow rate sensor, or serving as a back-up such as in event of a failure of the traditional sensor(s), in an RPT system for a simple, low cost monitoring solution. The treatment pressure may be determined by monitoring the change in the frequency of the dominant sound output from the acoustic generator.

In particular arrangements, detection of the acoustic signal may be facilitated using a mobile computing device comprising: a microphone sensitive to acoustic frequencies in at least the 16-25 kHz range; a processor for receiving electrical signals from the microphone representative of the detected acoustic signal, and a software application stored in a memory of the mobile computing device and comprising software code instructions for analysing the detected acoustic signal. The analysis may typically comprise determination of a frequency spectrum of the acoustic signal such as e.g. applying a fast Fourier transform (FFT) to obtain the frequency spectrum and determination of the dominant output frequency from the FFT output to be then correlated to a treatment pressure or flow rate.

5.7.3.1 Active Acoustic Analysis Processing Example

As described in more detail throughout this specification, one or more processors, such as a processor of a respiratory therapy device, a server and/or other electronic device (e.g., a smart phone or speaker) may execute processor control instructions, such as from any storage medium described herein, to conduct acoustic analyses using one or more acoustic generators according to the methodology illustrated in the flow chart FIG. 9. In an example of such a process, at 9002, a processor may be configured to access an electrical or data signal representative of an acoustic signal received by an acoustic receiver adapted to receive one or more inaudible acoustic signals emitted from one or more acoustic generator(s) associated with a flow path of a respiratory therapy system. At 9004, a processor may be configured to analyse the electrical or data signal to determine frequency spectral components such as in an inaudible frequency range attributable to the acoustic generator. At 9006, a processor may be configured to determine one or more parameters (e.g., flow rate, treatment pressure, and/or patient interface identification) of the respiratory therapy system based on one or more characteristics of the determined spectral components. At 9008, a processor may be configured to determine, set or change an operational parameter (e.g., vent flow characteristics, flow rate setting, pressure setting) or monitor data (e.g., compliance information, component useful life) related to the respiratory therapy system based on the determined parameter(s).

5.7.3.2 Applications for Active Acoustic Monitoring

For example, in addition to detecting and monitoring flow rates and or gas pressures in an RT system, acoustic generator 8500 described above may additionally, including concurrently, be utilised for a wide variety of applications in relation to a respiratory therapy regime including, but not limited to, for example:

5.7.3.2.1 Event Monitoring

OSA events such as apneas, hypopneas, respiratory effort-related arousals (RERAs), and snores may be detected in the flow rate waveform, and summary statistics such as the AHI may be computed from the identified events.

5.7.3.2.2 Sleep State Monitoring

Sleep state such as wake, deep sleep, and REM sleep may be inferred from the monitored flow rate waveform using known methods such as described in PCT published specification no. WO 2017/132726, the entire contents of which are herein incorporated by reference, and a hypnogram (time series of inferred sleep states of the patient over a therapy session) constructed based on the inferred sleep states.

5.7.3.2.3 Usage Monitoring

Conventional methods may be applied to the monitored flow rate waveform to determine whether the patient is using the respiratory therapy or whether the patient interface is off the patient's face at any given time. A record of therapy usage over a therapy session may be constructed based on the determined usage status at a series of time instants throughout the session, e.g. every thirty seconds. From the usage record, it may be determined whether the patient is compliant with a prescribed respiratory therapy regime.

5.7.3.2.4 Patient Interface Identification

A common problem with patient use of an RPT device and system is the selection of the correct patient interface (mask) type in the setup of the RPT device. Selection of an incorrect mask-type in the RPT device setup can cause discomfort to the patient, which may affect their compliance with the therapy regime, or may result in incorrect pressure and/or flow rates being delivered to the patient interface which may result in the patient's respiratory disorder being poorly managed. For instance, different types of masks (e.g. full face, nasal or nasal pillows type masks) each have unique vent flow characteristics which the RPT device must take into account when calculating the correct treatment pressure or flow rates to adequately treat the patient's condition.

This problem can conveniently be alleviated by incorporating an acoustic generator on patient interfaces for use with an RPT flow generator device 4000. In practice different mask types (e.g. full face, nasal or nasal pillows type masks), and even individual masks within a mask type will be provided with an acoustic generator having a characteristic frequency profile of their acoustic output when in use. Accordingly, an acoustic processor analysing the acoustic signal generated by the acoustic generator is therefore able, by configuring the processor, to inspect the characteristic frequency profile of the acoustic signal, and to accurately identify the mask type which the patient has connected to the RPT device, with the determined characteristic frequency profile such as by a table look-up associating mask type with characteristic frequencies.

The acoustic receiver, as discussed above, may comprise a microphone of a mobile computing device. A software application stored in memory of the mobile computing device comprising software instructions/code and adapted to be executed on a mobile computing device processor is advantageously adapted to determine the characteristic frequency profile of the acoustic signal emitted by the acoustic generator in use and correlate the characteristic frequency profile with the mask type. Once the mask type is known, the mobile computing device can advantageously communicate the mask type either directly to the RPT flow generator device 4000 or to a centralised server (e.g. cloud server/storage facility). The mobile computing device may communicate with the RPT generator either via a wired connection or a wireless communication protocol (e.g. WIFI, Bluetooth etc.) through an RPT device communication interface as would be appreciated by the skilled addressee.

Alternatively, the RPT device itself may optionally be fitted with a microphone adapted to function as the acoustic receiver to detect the acoustic signal generated by an acoustic generator. In this case the microphone generates an electrical signal representative of the acoustic signal and the electrical signal is provided to the processor of a diagnosis/monitoring device associated with RPT device 4000. Therein the processor may identify the mask type that the patient has connected to the RPT device, from the acoustic signal (e.g., with the determined characteristic frequency profile) such as by access to a lookup table.

5.7.3.2.5 RPT Device Setup

According to another aspect, once the mask type is known and has been communicated to, or determined by, the RPT device 4000, the configuration settings of the RPT device 4000 can be automatically updated to reflect the parameters (e.g., vent flow characteristics) for the particular type of mask which the patient 1000 has connected to the RPT system.

5.7.3.2.6 RPT System Features

Additionally, the RPT device 4000 may be configured to unlock particular enhanced configuration features when a patient 1000 connects a particular mask or mask type to the RPT device 4000. This may allow an RPT system to take full advantage of components that may be designed to work better together.

For example, the characteristic acoustic signal from an acoustic generator included with a patient interface 3000, when detected by a RPT device connected to the patient interface 3000 may cause the RPT device 4000 to offer the patient 1000 additional configuration(s) or usability features that would not otherwise be available to the patient 1000, such as Bi-Level treatments or APAP automatic CPAP titration features. Thus, the RPT system may be able to take full advantage of its componentry, by offering customised features suitable for an identified component, such as the patient interface 3000.

In particular arrangements, the RPT pressure generator device 4000 may be connected to a centralised server or cloud storage and processing system such that the centralised server may optionally be able to receive patient interface data collected from the RPT device 4000 and the patient interface 3000 for the purpose of providing the patient 1000 with a) enhanced sleep monitoring features, b) additional information regarding the type or brand of patient interface they have connected to the RPT device 4000. For example, upon identification of the patient interface by the RPT device 4000, the patient 1000 may be provided with helpful information about the particular mask-type they have connected, e.g. optimal mask set up and fitting instructions.

5.7.3.2.7 Enhanced Healthcare Informatics

In further arrangements, identification of the patient interface type which a patient connects to an RPT device 4000 capable of being connected to a centralised server or cloud data storage/processing infrastructure providing healthcare informatics data and monitoring of both connected populations and individual patient users on an as needed basis, will enable the healthcare informatics architecture to provide richer patient usage and/or therapy compliance data to both patients and their healthcare professionals.

In particular, the patient's therapy usage (determined as described above) may be associated with the identified patient interface type used during the therapy. This is particularly advantageous if the patient has access to multiple patient interfaces, as the usage of each interface type may be compared over time.

In some forms, a patient interface comprising an acoustic generator may advantageously allow a user to transmit and/or receive data between a local external device and a remote external device (e.g. server/cloud infrastructure) at a low cost. Thus, making use of the data transmitted via the acoustic generator:

the patient may be able to receive feedback, or coaching, a clinician may advantageously be able to view a patient's data, an equipment provider may be able to be notified that a component may require replacement, and/or a technician may be able to view the data and help the patient to troubleshoot any problems that they may be having with the RPT system or therapy. For example, a mismatch between the settings the patient has entered and the actual system properties, such as when the identity of the patient interface has been wrongly entered, may cause pressure swings at the patient interface that would be detectable by the disclosed active acoustic monitoring scheme. The patient would then receive a message to check the identity of the patient interface they had entered.

5.7.3.2.8 Patient Interface Lifecycle Monitoring

A common problem with RPT systems is that often a patient 1000 will continue to use a patient interface long past its recommended useable lifetime, thus resulting in the patient 1000 receiving less than adequate therapy due to natural degeneration of the mask.

According to one aspect of the present technology, an acoustic generator 8500 may be configured to generate an acoustic signal indicative of the health or age of the patient interface 3000. For example, as the patient interface 3000 ages, the sealing properties of the sealing-formation are likely to degrade thus resulting in an increase of baseline pressure/air flow leakage which must be compensated for by the RPT device 4000.

Such baseline leakage rate may be detectable by monitoring the long-term frequency spectral characteristics of the acoustic signal generated by the acoustic generator 8500.

When the detected baseline leakage rate changes, (e.g., it exceeds a predetermined value likely to compromise the effectiveness of the respiratory therapy regime), the patient 1000 may advantageously be provided with a reminder that their patient interface has exceeded its recommended useable life and may require replacement to ensure adequacy of the respiratory therapy required according to the patient's needs.

Alternatively, a blade formation 8530 of the acoustic generator 8500 may be configured to degrade over time in a predictable way. By monitoring the long-term frequency spectral characteristics of the acoustic signal generated by the acoustic generator 8500, this degradation may be measured and used to infer the age of the patient interface 3000. The patient 1000 may thereby advantageously be provided with a reminder that their patient interface has exceeded its recommended useable life and may require replacement to ensure adequacy of the respiratory therapy.

In another example, any particles dogging the patient interface would affect the generated acoustic signal. Therefore, the long-term frequency spectral characteristics of the acoustic signal generated by the acoustic generator 8500 may be used to infer the cleanliness of the patient interface 3000. The patient 1000 may thereby advantageously be provided with a reminder that their patient interface may require cleaning to ensure adequacy of the respiratory therapy.

5.7.3.2.9 Humidity Calculation

Respiratory therapies of the type discussed herein are often provided in conjunction with a humidifier 5000 to change the absolute humidity of air or gas for delivery to a patient relative to ambient air. Typically, the humidifier 5000 is used to increase the absolute humidity and increase the temperature of the flow of air (relative to ambient air) before delivery to the patient's airways thereby to improve the patient's level of comfort whilst undergoing treatment for a respiratory disorder.

The addition of water vapour to air (thus making the air humid) reduces the density of the air, which affects the operation of the acoustic generator 8500 thus causing a predictable change in the frequency of the acoustic signal generated. Accordingly, by closely monitoring the frequency shifts of the spectral components of the generated acoustic signal, changes in either the humidity of the air being delivered to the patient interface 3000 or the humidity of the air in the plenum chamber 3200 of the patient interface (depending on where the acoustic generator 8500 is located) may be estimated.

5.7.3.2.10 Measurement of Gas Parameters of Patient Expiratory Flow

Acoustic signals generated by an acoustic generator of the type disclosed herein may be used to monitor one or more additional parameters of the patient's expiratory flow. For example, under the assumption that expired air is saturated (i.e. relative humidity of 100%) and at a temperature of about 35 degrees Celsius, then the spectral output of the acoustic generator will be a function of such unknown factors as the patient's expired $CO_2$ levels, among others.

5.7.3.2.11 Measurement of Cardiac Output

One or more acoustic generators 8500 as disclosed herein may be used in conjunction with the Fick principle in a partial $CO_2$ rebreathing indirect Fick technique. The output provided by the RPT device 4000 in conjunction with known patient interface vent flow characteristics—known for example from acoustic fingerprinting identification of the patient interface connected as discussed above—to control the amount of partial $CO_2$ rebreathing by the patient 1000 in what is known as a deadspace manoeuvre. Changes in the spectral output of the acoustic generator 8500 under such conditions will be a function of expired $CO_2$ levels. Once the partial expired $CO_2$ levels are determined, then this can be used to provide an estimate of the patient's cardiac output (i.e. the volume of blood being pumped by the heart, in particular by a left or right ventricle, per unit time), and is an important indicator of how efficiently the patient's heart can meet the demands of the body.

5.7.3.3 Additional Illustrative Technology Examples

According to some versions of the present technology, there may be provided a device for measuring gas flow. The device may comprise an acoustic generator configured to generate an acoustic signal. The acoustic signal may be substantially inaudible to human hearing. Parameters of the acoustic signal such as but not limited to peak amplitude and frequency may be function of a gas flow rate or gas pressure or a combination of the gas flow rate and gas pressure of the gas flow.

According to a particular arrangement of the first aspect, there is provided a device for measuring gas flow, comprising an acoustic generator configured to generate an acoustic signal which may be substantially inaudible to human hearing as a function of a gas flow rate or gas pressure of the gas flow.

The acoustic signal may be substantially an ultrasonic acoustic signal. The ultrasonic acoustic signal may comprise a dominant acoustic component having a frequency greater than at least 20,000 Hz, or greater than at least 18,000 Hz, or greater than at least 17,000 Hz, or greater than at least 16,000 Hz.

The acoustic generator may be adapted to be incorporated into a patient interface suitable for a respiratory pressure therapy. The acoustic generator may be located in fluid communication with a plenum chamber or conduit of the patient interface for measurement of either a gas pressure or a gas flow rate of a respiratory therapy gas within the plenum chamber.

The acoustic generator may be provided in a connector module adapted to be connected to an airflow circuit, which may be intermediate between a patient interface and a respiratory pressure therapy device, for measurement of a flow rate of a gas between the respiratory pressure therapy device and the patient interface and vice versa.

The acoustic generator may be adapted to be incorporated into a respiratory pressure therapy device for monitoring of gas flow rates or pressures associated with the respiratory pressure therapy device.

The acoustic generator may be located adjacent an air flow outlet port of the respiratory pressure therapy device for measurement of a flow rate of a gas exiting the respiratory pressure therapy device via the air flow outlet port.

The acoustic generator may comprise any arrangement that causes energy in a fluid to oscillate between potential energy in the form of fluid pressure and kinetic energy in the form of fluid flow whereby the oscillation is naturally amplified at a specific frequency or frequency range, or a set of specific frequencies or frequency ranges.

The acoustic generator may be a whistle.

The acoustic generator may be a resonant pipe.

The acoustic generator may be a reed.

The acoustic generator may be a Helmholtz resonator.

The acoustic generator may be a membrane.

The acoustic generator may be a tensioned string.

According to another example of the technology, there may be provided an acoustic generator for measuring a gas flow. The acoustic generator may comprise a windway. The windway may comprise a windway inlet and a windway outlet. The windway inlet may be adapted to receive a sample portion of said gas flow into the windway. The acoustic generator may further comprise a blade formation adjacent the windway outlet. The blade formation may be adapted to interact with the sample portion of the flow of air to produce a turbulent flow of air. The acoustic generator may further comprise an acoustic chamber in fluid communication with the windway. The acoustic chamber may comprise a gas flow inlet at a first end of the acoustic chamber and a gas flow outlet at a second end of the acoustic chamber. The acoustic chamber may be configured to produce a back pressure dependent upon the flow rate of the sample portion of gas. The acoustic generator may generate an inaudible acoustic signal dependent on the back pressure.

According to a particular arrangement of these features, an example of such an acoustic generator for measuring a gas flow may include an acoustic generator comprising a windway. The windway may comprise a windway inlet and a windway outlet. The windway inlet may be adapted to receive a sample portion of said gas flow into the windway. The acoustic generator may further comprise a blade formation adjacent the windway outlet. The blade formation may be adapted to interact with the sample portion of the flow of air to produce a turbulent flow of air. The acoustic generator may further comprise an acoustic chamber in fluid communication with said windway. The acoustic chamber may comprise a gas flow inlet at a first end of the acoustic chamber and a gas flow outlet at a second end of the acoustic chamber. The acoustic chamber may be configured to produce a back pressure dependent upon the flow rate of the sample portion of gas. The acoustic generator may generate an inaudible acoustic signal dependent on the back pressure.

According to another example of the technology, there is provided an acoustic generator for measuring flow rate and/or pressure of a gas flow, the acoustic generator comprising:

a windway comprising a windway inlet and a windway outlet, the windway inlet adapted to receive a sample portion of said gas flow into said windway;

a blade formation adjacent said windway outlet and adapted to interact with said sample portion of said flow of air to produce a turbulent flow of air;

an acoustic chamber in fluid communication with said windway and comprising a gas flow inlet at a first end of said acoustic chamber and a gas flow outlet at a second end of said acoustic chamber; and wherein said acoustic generator generates an inaudible acoustic signal dependent on flow rate and/or pressure.

According to a particular arrangement of such an acoustic generator for measuring flow rate and/or pressure of a gas flow, the acoustic generator may comprise: a windway comprising a windway inlet and a windway outlet, the windway inlet adapted to receive a sample portion of said gas flow into said windway; a blade formation adjacent said windway outlet and adapted to interact with said sample portion of said flow of air to produce a turbulent flow of air; an acoustic chamber in fluid communication with said windway and comprising a gas flow inlet at a first end of said acoustic chamber and a gas flow outlet at a second end of said acoustic chamber; and wherein said acoustic generator generates an inaudible acoustic signal dependent on flow rate and/or pressure.

According to a still further example of the technology, there is provided an acoustic generator for measuring flow rate and/or pressure of a gas flow. The acoustic generator may comprise a windway. The windway may comprise a windway inlet and a windway outlet. The windway inlet may be adapted to receive a sample portion of the gas flow into the windway. The acoustic generator may further comprise a blade formation adjacent the windway outlet. The blade formation may be adapted to interact with the sample portion of the flow of air to produce a turbulent flow of air. The acoustic generator may further comprise an acoustic chamber in fluid communication with the windway. The acoustic chamber may comprise a gas flow inlet at a first end of the acoustic chamber and a gas flow outlet at a second end of the acoustic chamber. The acoustic generator may generate an inaudible acoustic signal dependent on the flow rate and/or pressure of the gas flow.

According to a particular arrangement, an acoustic generator for measuring flow rate and/or pressure of a gas flow, may include: a windway comprising a windway inlet and a windway outlet, the windway inlet adapted to receive a sample portion of said gas flow into said windway; a blade formation adjacent said windway outlet and adapted to interact with said sample portion of said flow of air to produce a turbulent flow of air; an acoustic chamber in fluid communication with said windway and comprising a gas flow inlet at a first end of said acoustic chamber and a gas flow outlet at a second end of said acoustic chamber; and wherein said acoustic generator generates an inaudible acoustic signal dependent on the flow rate and/or pressure of the gas flow.

An acoustic receiver may be provided adapted for communication with the acoustic generator. The acoustic receiver may be configured to detect the acoustic frequency produced by the acoustic generator and to provide an indication of a gas flow rate of said gas flow.

The acoustic signal may be generated at a frequency which is inaudible to humans. The acoustic generator may generate an ultrasonic signal.

According to another example of the technology, in a system for treating a respiratory disorder in a patient, the system may include a pressure generator configured to generate a flow of air having a flow rate and/or pressure for treating the respiratory disorder; an air conduit in fluid communication with an air outlet of the pressure generator; and an air inlet of a patient interface; there is provided an acoustic generator. The acoustic generator may be located adjacent to or in the patient interface. The acoustic generator may be in fluid communication with the flow of air and ambient air. The acoustic generator may comprise a windway inlet adapted to receive a sample portion of the flow of air into a windway. The windway may have a windway outlet. The acoustic generator may further comprise a blade formation adjacent the windway outlet. The blade formation may be adapted to interact with the sample portion of the flow of air to produce a turbulent flow of air. The acoustic generator may further comprise an acoustic chamber in fluid communication with the windway. The acoustic chamber may comprise a gas flow inlet at a first end of the acoustic chamber and a gas flow outlet at a second end of the acoustic chamber. The acoustic chamber may be configured to produce a back pressure dependent upon the flow rate of the sample portion of the flow of air. The turbulent flow of air may interact with the back pressure to produce an inaudible acoustic signal having an acoustic frequency dependent upon either: the flow rate of the gas flow delivered to the patient interface; or the pressure of pressurised air in the patient interface.

According to a particular arrangement of such a system for treating a respiratory disorder in a patient, the system may include a patient interface and a pressure generator configured to generate a flow of air having a flow rate and/or pressure for treating the respiratory disorder; an air conduit in fluid communication with an air outlet of the pressure generator; and an air inlet of a patient interface; there is provided an acoustic generator located adjacent to or in the patient interface, said acoustic generator being in fluid communication with said flow of air and ambient air, said acoustic generator comprising: a windway inlet adapted to receive a sample portion of said flow of air into a windway, said windway having a windway outlet; a blade formation adjacent said windway outlet and adapted to interact with said sample portion of said flow of air to produce a turbulent flow of air; an acoustic chamber in fluid communication with said windway and comprising a gas flow inlet at a first end of said acoustic chamber and a gas flow outlet at a second end of said acoustic chamber, said acoustic chamber configured to produce a back pressure dependent upon the flow rate of the sample portion of said flow of air; and wherein the turbulent flow of air interacts with the back pressure to produce an inaudible acoustic signal having an acoustic frequency dependent upon either: the flow rate of the gas flow delivered to the patient interface; or the pressure of pressurised air in the patient interface.

According to another example of the technology, in a system for treating a respiratory disorder in a patient, the system comprising a pressure generator configured to generate a flow of air having a flow rate and/or pressurised air having an air pressure for treating the respiratory disorder; an air conduit in fluid communication with an air outlet of the pressure generator and an air inlet of a patient interface; there is provided, a first acoustic generator. The first acoustic generator may be located adjacent to or within the patient interface. The acoustic generator may comprise a whistle in fluid communication with the flow of air or the pressurised air. The whistle may be adapted to generate an inaudible acoustic signal having an acoustic frequency dependent on the flow rate of the gas flow.

According to a particular arrangement of such an example, in a system for treating a respiratory disorder in a patient, the system comprising a pressure generator configured to generate a flow of air having a flow rate and/or pressurised air having an air pressure for treating the respiratory disorder; an air conduit in fluid communication with an air outlet of the pressure generator and an air inlet of a patient interface; there is provided, a first acoustic generator located adjacent to or within the patient interface, the acoustic generator comprising a whistle in fluid communication with the flow of air or the pressurised air; wherein the whistle may be adapted to generate an inaudible acoustic signal having an acoustic frequency dependent on the flow rate of the gas flow.

The acoustic signal may comprise an ultrasonic signal. The acoustic signal may comprise a frequency that is inaudible to humans. The acoustic signal may comprise a dominant acoustic component having a frequency greater than at least 20,000 Hz, or greater than at least 18,000 Hz, or greater than at least 17,000 Hz.

The acoustic generator may comprise a windway comprising an windway inlet adapted to receive a sample portion of the flow of air into a windway, and further comprising a windway outlet. The acoustic generator may further comprise a blade formation adjacent the windway outlet and adapted to interact with the sample portion of the flow of air to produce a turbulent flow of air. The acoustic generator may further comprise an acoustic chamber in fluid communication with the windway. The acoustic chamber may comprise a gas flow inlet at a first end of the acoustic chamber and a gas flow outlet at a second end of the acoustic chamber. The acoustic chamber may be configured to produce a back pressure dependent upon the flow rate of the sample portion of the flow of air. The turbulent flow of air may interact with the back pressure to produce an acoustic signal having an acoustic frequency dependent upon the flow rate of the gas flow.

The windway may have a length of between about 3 mm and about 7 mm. The windway may have a length of between about 5 mm and about 7 mm. The windway may have a width of between about 0.7 mm and about 1.5 mm. The windway may have a height of between about 0.6 mm and about 0.7 mm. The acoustic chamber may comprise a horn region at a distal end of the acoustic chamber. The he horn region may have a length of between about 2 mm and about 4.5 mm. The horn region may have a radius of curvature of between about 2 degree and about 8.5 degrees. The blade formation may comprise a leading edge, the leading edge being adapted to minimise human audible turbulent noise in operation. The windway outlet and the leading edge of the blade formation may be separated by a distance of between about 0.5 mm and about 2 mm. The length of the acoustic chamber, less the length of the horn region, may be between about 1 mm and about 3.5 mm.

The leading edge may be rounded to reduce audible turbulent noise generated by the acoustic generator or to improve the robustness of the design. Alternatively, the leading edge may comprise either an undercut or an overcut to reduce audible turbulent noise generated by the acoustic generator or to improve the robustness of the design. The leading edge may be located between about 1 mm and about 5 mm from the windway outlet. The leading edge of the blade formation may be positioned in line with a central axis of the windway. The leading edge of the blade formation may be positioned below the centre of the windway.

The blade formation may comprise a first blade formation surface substantially aligned with a central axis of the windway. The blade formation may further comprise a second blade formation surface aligned at a blade angle with respect to the central axis of the windway. The blade angle may be between about 20 degrees and about 40 degrees. The blade angle may be about 30 degrees.

The pressure generator may comprise a second acoustic generator located adjacent the air outlet of the pressure generator and in fluid communication with the flow of air. The second acoustic generator may comprise a windway inlet adapted to receive a sample portion of the flow of air into a windway the windway having a windway outlet. The second acoustic generator may further comprise a blade formation adjacent the windway outlet and adapted to interact with the sample portion of the flow of air to produce a turbulent flow of air. The second acoustic generator may further comprise an acoustic chamber in fluid communication with the windway and comprising a gas flow inlet at a first end of the acoustic chamber and a gas flow outlet at a second end of the acoustic chamber, the acoustic chamber configured to produce a back pressure dependent upon the flow rate of the sample portion of the flow of air exiting the air outlet of the pressure generator. The turbulent flow of air may interacts with the back pressure to produce an acoustic signal having an acoustic frequency dependent upon the flow rate of the gas flow exiting the outlet of the pressure generator.

The second acoustic generator and the first generator may be matched such that the acoustic generators each produce an acoustic signal having substantially equal acoustic frequencies in relation to a given flow rate. The acoustic signals generated by the first acoustic generator and the second acoustic generator may interact to produce a combined acoustic beat signal representative of a difference in the flow rate exiting the outlet of the pressure generator and the flow rate delivered to the patient interface. Thus, changes in the beat signal provides a representation of variations in flow rate within the system.

According to another example of the technology, there is provided an acoustic detector configured to detect acoustic signals generated by the acoustic generator as claimed in any one of the preceding aspects. The acoustic detector may be further adapted to detect an acoustic beat frequency formed from interaction of the acoustic signals generated by the first acoustic generator and the second acoustic generator.

According to an another example of the technology, there is provided a flow rate sensor for measuring a gas flow rate of a flow of breathable gas delivered to a patient for treatment of a respiratory disorder, the flow rate sensor comprising:

at least one acoustic generator;

an acoustic chamber connected to the acoustic generator, wherein the acoustic chamber may comprise at least one gas flow inlet at a first end of the acoustic chamber and a gas flow outlet at a second end of the acoustic chamber, the acoustic chamber configured to produce a back pressure dependent on gas flow rate or air pressure in the acoustic chamber; and wherein the acoustic generator generates an inaudible acoustic signal dependent on the back pressure, the acoustic signal being representative of the gas flow rate.

According to a particular arrangement of such an example, a flow rate sensor for measuring a gas flow rate of a flow of breathable gas delivered to a patient for treatment of a respiratory disorder, includes: at least one acoustic generator; an acoustic chamber connected to the acoustic generator, wherein the acoustic chamber may comprise at least one gas flow inlet at a first end of the acoustic chamber and a gas flow outlet at a second end of the acoustic chamber, the acoustic chamber configured to produce a back pressure dependent on gas flow rate or air pressure in the acoustic chamber; and wherein the acoustic generator generates an inaudible acoustic signal dependent on the back pressure, the acoustic signal being representative of the gas flow rate.

According to another example of the technology, there is provided a system for measuring gas flow rate of a flow of breathable gas delivered to a patient for treatment of a respiratory disorder, the system comprising:

an acoustic generator in communication with the flow of breathable gas for generating an inaudible acoustic signal representative of the gas flow rate or air pressure;

an acoustic receiver operatively coupled to the acoustic signal for generating an electrical signal representative of the acoustic signal; and a processor adapted to receive the electrical signal and process the electrical signal to determine a frequency spectrum of the electrical signal and determining the flow rate of the breathable gas from the frequency spectrum.

According to a particular arrangement of such an example, there is provided a system for measuring gas flow rate of a flow of breathable gas delivered to a patient for treatment of a respiratory disorder, the system comprising: an acoustic generator in communication with the flow of breathable gas for generating an inaudible acoustic signal representative of the gas flow rate or air pressure; an acoustic receiver operatively coupled to the acoustic signal for generating an electrical signal representative of the acoustic signal; and a processor adapted to receive the electrical signal and process the electrical signal to determine a frequency spectrum of the electrical signal and determining the flow rate of the breathable gas from the frequency spectrum.

The processor may be further adapted for determining a pressure of the breathable gas delivered to the patient.

The acoustic generator may generate an ultrasonic acoustic signal representative of the gas flow rate. The ultrasonic acoustic signal may have a frequency of between about 16 kilohertz and about 24 kilohertz. The ultrasonic acoustic signal may be representative of positive gas pressures delivered to the patient of between about 4 cmH$_2$O and about 20 cmH$_2$O above ambient atmospheric pressure. The acoustic signal generated by the acoustic generator may have a frequency that is inaudible to humans over a pressure range of between about 4 cmH$_2$O and about 20 cmH$_2$O above ambient atmospheric pressure.

The acoustic generator may be provided adjacent to or integrated with a patient interface adapted to receive the flow of breathable gas for delivery to a patient for treatment of a respiratory disorder. The acoustic generator may be provided adjacent to or integrated with an airflow exit port of a respiratory pressure device adapted to provide the flow of breathable gas for delivery to the patient for treatment of a respiratory disorder. The system may comprise an inline connector adapted to be inserted in an air flow path intermediate an air conduit for delivering the flow of breathable gas delivered to the patient and the patient interface. The connector may comprise the acoustic generator.

The acoustic generator may comprise: a windway comprising a windway inlet and a windway outlet; an acoustic outlet; a blade formation; and an acoustic chamber in fluid communication with the windway and the acoustic outlet the acoustic chamber comprising a gas flow inlet at a first end of the acoustic chamber and a gas flow outlet at a second end of the acoustic chamber, the acoustic chamber configured to produce a back pressure dependent on gas flow rate or air pressure in the acoustic chamber.

A first acoustic generator may be located in the patient interface such that the windway inlet is in fluid communication with a plenum chamber of the patient interface and an acoustic outlet of the acoustic generator is in fluid communication with ambient air. A second acoustic generator may be located in the patient interface. The second acoustic generator may comprise an acoustic chamber in fluid communication with the windway and the acoustic outlet. The acoustic chamber of the second acoustic generator may comprise a gas flow inlet at a first end of the acoustic chamber, and wherein a second end of the acoustic chamber may be sealed.

The acoustic generator may comprise a windway inlet port adapted to receive a flow of air. The acoustic generator may be adapted to generate an acoustic signal having a frequency dependent upon the relative or absolute humidity of air received by the windway inlet.

The acoustic generator may comprise a windway inlet port adapted to receive a flow of air. The acoustic generator may be adapted to generate an acoustic signal having a frequency dependent upon the relative or absolute partial concentration of a gas in the air in communication with the windway inlet port of the acoustic generator.

The acoustic generator may be adapted to generate an acoustic signal having a frequency dependent upon the relative or absolute partial concentration of a gas in the air expired by a patient. The partial concentration of gas may comprise a gas of either, carbon dioxide, carbon monoxide.

According to another example of the technology, a patient interface may comprise a plenum chamber pressurisable to a therapeutic pressure of at least 6 cmH$_2$O above ambient air pressure, the plenum chamber including a plenum chamber inlet port, the plenum chamber inlet port being sized and structured to receive a flow of air at the therapeutic pressure for breathing by a patient. The patient interface may further comprise a seal-forming structure constructed and arranged to maintain the therapeutic pressure in the plenum chamber throughout the patient's respiratory cycle in use. The patient interface may further comprise a positioning and stabilising structure to hold the seal-forming structure in a therapeutically effective position on the patient's head. The patient interface may further comprise a washout vent structure configured to allow a continuous vent flow from an interior of the plenum chamber to ambient whilst the pressure within the plenum chamber may be positive with respect to ambient. The patient interface may further comprise an acoustic generator in fluid communication with the plenum chamber. The acoustic generator may comprise a windway inlet adapted to receive a sample portion of the flow of air into a windway, the windway having a windway outlet. The acoustic generator may further comprise a blade formation adjacent the windway outlet and adapted to interact with the sample portion of the flow of air to produce a turbulent flow of air. The acoustic generator may further comprise an acoustic chamber in fluid communication with the windway and comprising a gas flow inlet at a first end of the acoustic chamber and a gas flow outlet at a second end of the acoustic chamber, the acoustic chamber configured to produce a back pressure dependent upon the flow rate of the sample portion of the flow of air. The turbulent flow of air may interact with the back pressure to produce an inaudible acoustic signal having an acoustic frequency dependent upon the flow rate of the gas flow delivered into the plenum chamber and/or the pressure of pressurised air in the plenum chamber.

According to a particular arrangement of such an example, the patient interface may include: a plenum chamber pressurisable to a therapeutic pressure of at least 6 cmH$_2$O above ambient air pressure, the plenum chamber including a plenum chamber inlet port, the plenum chamber inlet port being sized and structured to receive a flow of air at the therapeutic pressure for breathing by a patient; a seal-forming structure constructed and arranged to maintain the therapeutic pressure in the plenum chamber throughout the patient's respiratory cycle in use; a positioning and stabilising structure to hold the seal-forming structure in a therapeutically effective position on the patient's head; a washout vent structure configured to allow a continuous vent flow from an interior of the plenum chamber to ambient whilst the pressure within the plenum chamber may be positive with respect to ambient; and an acoustic generator in fluid communication with the plenum chamber, the acoustic generator comprising: a windway inlet adapted to receive a sample portion of the flow of air into a windway, the windway having a windway outlet; a blade formation adjacent the windway outlet and adapted to interact with the sample portion of the flow of air to produce a turbulent flow of air; and an acoustic chamber in fluid communication with the windway and comprising a gas flow inlet at a first end of the acoustic chamber and a gas flow outlet at a second end of the acoustic chamber, the acoustic chamber configured to produce a back pressure dependent upon the flow rate of the sample portion of the flow of air; and wherein the turbulent flow of air interacts with the back pressure to produce an inaudible acoustic signal having an acoustic frequency dependent upon the flow rate of the gas flow delivered into the plenum chamber and/or the pressure of pressurised air in the plenum chamber.

The acoustic generator may be in fluid communication with the plenum chamber. The acoustic generator may be further in fluid communication with ambient air pressure external to the plenum chamber.

According to another example of the technology, in a respiratory treatment system for treating a respiratory disorder in a patient, the system comprising a pressure generator configured to generate a flow of air having a flow rate for treating the respiratory disorder; an air conduit in fluid communication with an air outlet of the pressure generator; and an air inlet of a patient interface, there is provided a method for determining treatment parameters associated with a respiratory therapy treatment. The method may comprise the step of providing an acoustic receiver adapted to receive acoustic noise signals emitted from the pressure generator and/or the patient interface in use. The method may further comprise the step of receiving the acoustic signal with the acoustic receiver and generating an electrical signal representative of the acoustic signal. The method may further comprise the step of receiving the electrical signal with a processor adapted to analyse the electrical signal. The method may further comprise the step of analysing the acoustic signal with the processor to determine frequency spectral components in the acoustic signal.

According to a particular arrangement of the eleventh aspect, in a respiratory treatment system for treating a respiratory disorder in a patient, the system comprising a pressure generator configured to generate a flow of air having a flow rate for treating the respiratory disorder; an air conduit in fluid communication with an air outlet of the pressure generator; and an air inlet of a patient interface, there is provided a method for determining treatment parameters associated with a respiratory therapy treatment, the method comprising the steps of: providing an acoustic receiver adapted to receive acoustic noise signals emitted from the pressure generator and/or the patient interface in use; receiving the acoustic signal with the acoustic receiver and generating an electrical signal representative of the acoustic signal; receiving the electrical signal with a processor adapted to analyse the electrical signal; and analysing the acoustic signal with the processor to determine frequency spectral components in the acoustic signal.

The method may further comprise the step of correlating the frequency spectral components to characteristic signals generated by one or more mechanical components of the pressure generator.

The method may further comprise the step of correlating the frequency spectral components to characteristic pneumatic noise signals generated by either the pressure generator, the air conduit or the patient interface.

The method may further comprise the step of calculating one or more treatment parameters associated with the respiratory treatment system. The one or more treatment parameters may be selected from the group comprising: gas flow rate; gas pressure; vent flow rate, leak flow rate, blower rotation speed, impeller blade pass frequency.

According to another example of the technology, a method provides automatic configuration of a respiratory pressure therapy (RPT) device adapted for treating a respiratory disorder in a patient. The respiratory pressure therapy (RPT) device may comprise an RPT inlet configured to receive a supply of air at ambient pressure. The RPT device may further comprise a blower comprising an impeller coupled to a shaft and an electric motor, the impeller may be constructed and arranged to receive a supply of air from the inlet and to direct the supply of air radially outwardly. The RPT device may further comprise an RPT outlet comprising a connector structured to make a sealed positive pressure connection with another component. The RPT device may further comprise a controller configured to control the blower to maintain a positive pressure at the outlet within a range of about 4 cmH$_2$O to about 25cmH$_2$O. The method for automatic configuration of a respiratory pressure therapy (RPT) device may comprise the step of providing a patient interface. The patient interface may comprise a plenum chamber pressurisable to a therapeutic pressure of at least 4 cmH$_2$O above ambient air pressure, the plenum chamber including a plenum chamber inlet port sized and structured to receive a flow of air at the therapeutic pressure for breathing by a patient. The patient interface may further comprise a seal-forming structure constructed and arranged to maintain the therapeutic pressure in the plenum chamber throughout the patient's respiratory cycle in use. The method may further comprise the step of connecting an air circuit to the RPT outlet and to the plenum chamber of the patient interface for delivering a pressurised flow of breathable gas to the patient for treatment of the respiratory disorder. The method may further comprise the step of providing an acoustic generator located adjacent to or in the patient interface. The method may further comprise the step of providing the pressurised flow of breathable gas to the patient interface such that the acoustic generator generates an inaudible acoustic signal having a unique frequency in relation to a particular type of patient interface connected to the air circuit. The method may further comprise the step of providing an acoustic receiver. The method may further comprise the step of receiving the acoustic signal with the acoustic receiver and generating a signal representative of the type of patient interface connected to the air circuit. The method may further comprise the step of configuring operating parameters of the RPT device consistent with the type of patient interface connected to the air circuit for effective treatment of the respiratory disorder.

According to a particular arrangement of the twelfth aspect, there is provided a method for automatic configuration of a respiratory pressure therapy (RPT) device adapted for treating a respiratory disorder in a patient, the respiratory pressure therapy (RPT) device comprising: an RPT inlet configured to receive a supply of air at ambient pressure; a blower comprising an impeller coupled to a shaft and an electric motor, the impeller may be constructed and arranged to receive a supply of air from the inlet and to direct the supply of air radially outwardly, an RPT outlet comprising a connector structured to make a sealed positive pressure connection with another component; a controller configured to control the blower to maintain a positive pressure at the outlet within a range of about 4 cmH$_2$O to about 25cmH$_2$O; providing a patient interface comprising: a plenum chamber pressurisable to a therapeutic pressure of at least 4 cmH$_2$O above ambient air pressure, the plenum chamber including a plenum chamber inlet port sized and structured to receive a flow of air at the therapeutic pressure for breathing by a patient, a seal-forming structure constructed and arranged to maintain the therapeutic pressure in the plenum chamber throughout the patient's respiratory cycle in use; connecting an air circuit to the RPT outlet and to the plenum chamber of the patient interface for delivering a pressurised flow of breathable gas to the patient for treatment of the respiratory disorder; providing an acoustic generator located adjacent to or in the patient interface; providing the pressurised flow of breathable gas to the patient interface such that the acoustic generator generates an inaudible acoustic signal having a unique frequency in relation to a particular type of patient interface connected to the air circuit; providing an acoustic receiver; receiving the acoustic signal with the acoustic receiver and generating a signal representative of the type of patient interface connected to the air circuit; and configuring operating parameters of the RPT device consistent with the type of patient interface connected to the air circuit for effective treatment of the respiratory disorder.

According to a further example of the technology, there is provided a method for monitoring a respiratory pressure therapy treatment adapted for treating a respiratory disorder in a patient. The method may comprise the step of providing a respiratory pressure therapy (RPT) device. The RPT device may comprise an RPT inlet configured to receive a supply of air at ambient pressure. The RPT device may further comprise a blower comprising an impeller coupled to a shaft and an electric motor, the impeller may be constructed and arranged to receive a supply of air from the inlet and to direct the supply of air radially outwardly. The RPT device may further comprise an RPT outlet comprising a connector structured to make a sealed positive pressure connection with another component. The RPT device may further comprise a controller configured to control the blower to maintain a positive pressure at the outlet within a range of about 4 cmH$_2$O to about 25cmH$_2$O. The method may further comprise the step of providing a patient interface. The patient interface may comprise a plenum chamber pressurisable to a therapeutic pressure of at least 6 cmH$_2$O above ambient air pressure, the plenum chamber including a plenum chamber inlet port sized and structured to receive a flow of air at the therapeutic pressure for breathing by a patient. The patient interface may further comprise a seal-forming structure constructed and arranged to maintain the therapeutic pressure in the plenum chamber throughout the patient's respiratory cycle in use. The method may further comprise the step of connecting an air circuit to the RPT outlet and to the plenum chamber of the patient interface for delivering a pressurised flow of breathable gas generated by the blower to the patient for treatment of the respiratory disorder. The method may further comprise the step of providing an acoustic generator located adjacent to or in the patient interface. The method may further comprise the step of providing the pressurised flow of breathable gas to the patient interface such that the acoustic generator generates an inaudible acoustic signal having a frequency spectrum dependent upon either a gas flow rate or a gas pressure of the flow of breathable gas. The method may further comprise the step of providing an acoustic receiver coupled to an acoustic processor. The method may further comprise the step of receiving the acoustic signal with the acoustic receiver and generating a signal representative of either the gas flow rate or the gas pressure of the flow of breathable gas. The method may further comprise the step of analysing the acoustic signal with the acoustic processor to determine frequency spectral components in the acoustic frequency. The method may further comprise the step of determining the gas pressure and/or flow rate of the pressurised flow of breathable gas.

According to a particular arrangement of such an example, there is provided a method for monitoring a respiratory pressure therapy treatment adapted for treating a respiratory disorder in a patient, the method comprising: providing a respiratory pressure therapy (RPT) device comprising: an RPT inlet configured to receive a supply of air at ambient pressure; a blower comprising an impeller coupled to a shaft and an electric motor, the impeller may be constructed and arranged to receive a supply of air from the inlet and to direct the supply of air radially outwardly, an RPT outlet comprising a connector structured to make a sealed positive pressure connection with another component; a controller configured to control the blower to maintain a positive pressure at the outlet within a range of about 4 cmH$_2$O to about 25cmH$_2$O providing a patient interface comprising: a plenum chamber pressurisable to a therapeutic pressure of at least 6 cmH$_2$O above ambient air pressure, the plenum chamber including a plenum chamber inlet port sized and structured to receive a flow of air at the therapeutic pressure for breathing by a patient; a seal-forming structure constructed and arranged to maintain the therapeutic pressure in the plenum chamber throughout the patient's respiratory cycle in use; connecting an air circuit to the RPT outlet and to the plenum chamber of the patient interface for delivering a pressurised flow of breathable gas generated by the blower to the patient for treatment of the respiratory disorder; providing an acoustic generator located adjacent to or in the patient interface; providing the pressurised flow of breathable gas to the patient interface such that the acoustic generator generates an inaudible acoustic signal having a frequency spectrum dependent upon either a gas flow rate or a gas pressure of the flow of breathable gas; providing an acoustic receiver coupled to an acoustic processor; receiving the acoustic signal with the acoustic receiver and generating a signal representative of either the gas flow rate or the gas pressure of the flow of breathable gas; analysing the acoustic signal with the acoustic processor to determine frequency spectral components in the acoustic frequency; and determining the gas pressure and/or flow rate of the pressurised flow of breathable gas.

According to a yet additional example of the technology, a method provides monitoring a respiratory pressure therapy treatment adapted for treating a respiratory disorder in a patient. The method may comprise the step of providing a respiratory pressure therapy (RPT) device. The RPT device may comprise an RPT inlet configured to receive a supply of air at ambient pressure. The RPT device may comprise a blower comprising an impeller coupled to a shaft and an electric motor, the impeller may be constructed and arranged to receive a supply of air from the inlet and to direct the supply of air radially outwardly. The RPT device may comprise an RPT outlet comprising a connector structured to make a sealed positive pressure connection with another component. The RPT device may comprise a controller configured to control the blower to maintain a positive pressure at the outlet within a range of about 4 cmH$_2$O to about 25 cmH$_2$O. The method may further comprise the step of providing a patient interface. The patient interface may comprise a plenum chamber pressurisable to a therapeutic pressure of at least 6 cmH$_2$O above ambient air pressure, the plenum chamber including a plenum chamber inlet port sized and structured to receive a flow of air at the therapeutic pressure for breathing by a patient. The patient interface may further comprise a seal-forming structure constructed and arranged to maintain the therapeutic pressure in the plenum chamber throughout the patient's respiratory cycle in use. The method may further comprise the step of connecting an air circuit to the RPT outlet and to the plenum chamber of the patient interface for delivering a pressurised flow of breathable gas generated by the blower to the patient for treatment of the respiratory disorder. The method may further comprise the step of providing an acoustic generator located adjacent to or in the patient interface. The method may further comprise the step of providing the pressurised flow of breathable gas to the patient interface such that the acoustic generator generates an inaudible acoustic signal having a frequency spectrum dependent upon either a gas flow rate or a gas pressure of the flow of breathable gas. The method may further comprise the step of providing an acoustic receiver coupled to an acoustic processor. The method may further comprise the step of receiving the acoustic signal with the acoustic receiver and generating a signal representative of either the gas flow rate or the gas pressure of the flow of breathable gas. The method may further comprise the step of analysing the acoustic signal with the acoustic processor to determine frequency spectral components in the acoustic frequency. The method may further comprise the step of determining the gas pressure and/or flow rate of the pressurised flow of breathable gas.

According to a particular arrangement of such an example, the method for monitoring a respiratory pressure therapy treatment adapted for treating a respiratory disorder in a patient may include: providing a respiratory pressure therapy (RPT) device comprising: an RPT inlet configured to receive a supply of air at ambient pressure; a blower comprising an impeller coupled to a shaft and an electric motor, the impeller may be constructed and arranged to receive a supply of air from the inlet and to direct the supply of air radially outwardly, an RPT outlet comprising a connector structured to make a sealed positive pressure connection with another component; a controller configured to control the blower to maintain a positive pressure at the outlet within a range of about 4 cmH₂O to about 25cmH₂O; providing a patient interface comprising: a plenum chamber pressurisable to a therapeutic pressure of at least 6 cmH₂O above ambient air pressure, the plenum chamber including a plenum chamber inlet port sized and structured to receive a flow of air at the therapeutic pressure for breathing by a patient, a seal-forming structure constructed and arranged to maintain the therapeutic pressure in the plenum chamber throughout the patient's respiratory cycle in use; connecting an air circuit to the RPT outlet and to the plenum chamber of the patient interface for delivering a pressurised flow of breathable gas generated by the blower to the patient for treatment of the respiratory disorder; providing an acoustic generator located adjacent to or in the patient interface; providing the pressurised flow of breathable gas to the patient interface such that the acoustic generator generates an inaudible acoustic signal having a frequency spectrum dependent upon either a gas flow rate or a gas pressure of the flow of breathable gas; providing an acoustic receiver coupled to an acoustic processor; receiving the acoustic signal with the acoustic receiver and generating a signal representative of either the gas flow rate or the gas pressure of the flow of breathable gas; analysing the acoustic signal with the acoustic processor to determine frequency spectral components in the acoustic frequency; and determining the gas pressure and/or flow rate of the pressurised flow of breathable gas.

The acoustic receiver may comprise a microphone connected to the RPT device. The acoustic receiver may comprise a microphone of a mobile computing device located in acoustic vicinity of the acoustic generator. The mobile computing device may comprise a processor adapted to receive electrical signals from the microphone, the electrical signals being representative of the acoustic signal. The processor may be further adapted to process the received electrical signals to determine frequency spectral components of the acoustic signal. The processor may be further adapted to calculate gas pressure and/or gas flow rate of the flow of breathable gas from the spectral components.

According to another example of the technology, a computer program product may have a computer readable medium having a computer program recorded therein for automatic configuration of a respiratory pressure therapy (RPT) device for treatment of a respiratory disorder, the computer program product comprising: computer program code means for receiving with an acoustic receiver a signal representative of an acoustic signal, the acoustic signal being generated by an acoustic generator coupled via an air circuit to a patient interface suitable for treatment of a respiratory disorder, wherein the acoustic signal has a frequency spectrum uniquely representative of a type of patient interface suitable for providing a respiratory pressure therapy and generating a signal representative of the type of patient interface; computer program code means for determining optimised configuration parameters for an RPT (respiratory pressure therapy) device consistent with the type of patient interface connected to the air circuit for effective treatment of the respiratory disorder; and computer program code means for configuring an RPT device adapted to provide a respiratory pressure therapy using the optimised configuration parameters for treatment of the respiratory disorder.

According to a further example of the technology, a computer program product may have a computer readable medium having a computer program recorded therein for monitoring a respiratory pressure therapy treatment adapted for treating a respiratory disorder in a patient, the computer program product comprising: computer program code means for computer program code means for, with an acoustic receiver, receiving a signal representative of an inaudible acoustic signal, the acoustic signal being generated by an acoustic generator coupled to a patient interface suitable for treatment of a respiratory disorder, wherein the acoustic signal has a frequency spectrum dependent upon a gas flow rate and/or a gas pressure of a pressurised flow of breathable gas supplied to the patient interface; computer program code means for analysing the received signal and determine a frequency spectrum of the inaudible acoustic signal; computer program means for determining the gas pressure and/or flow rate of the pressurised flow of breathable gas.

An aspect of one form of the present technology is a method of manufacturing apparatus.

An aspect of certain forms of the present technology is a medical device that is easy to use, e.g. by a person who does not have medical training, by a person who has limited dexterity, vision or by a person with limited experience in using this type of medical device.

An aspect of one form of the present technology is a portable RPT device that may be carried by a person, e.g., around the home of the person.

An aspect of one form of the present technology is a patient interface that may be washed in a home of a patient, e.g., in soapy water, without requiring specialised cleaning equipment. An aspect of one form of the present technology is a humidifier tank that may be washed in a home of a patient, e.g., in soapy water, without requiring specialised cleaning equipment.

5.8 Glossary

For the purposes of the present technology disclosure, in certain forms of the present technology, one or more of the following definitions may apply. In other forms of the present technology, alternative definitions may apply.

5.8.1 General

Air: In certain forms of the present technology, air may be taken to mean atmospheric air, and in other forms of the present technology air may be taken to mean some other combination of breathable gases, e.g. atmospheric air enriched with oxygen.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

Continuous Positive Airway Pressure (CPAP) therapy: Respiratory pressure therapy in which the treatment pressure is approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Flow rate: The volume (or mass) of air delivered per unit time. Flow rate may refer to an instantaneous quantity. In some cases, a reference to flow rate will be a reference to a scalar quantity, namely a quantity having magnitude only. In other cases, a reference to flow rate will be a reference to a vector quantity, namely a quantity having both magnitude and direction. Flow rate may be given the symbol Q. 'Flow rate' is sometimes shortened to simply 'flow' or 'airflow'.

Leak: The word leak will be taken to be an unintended flow of air. In one example, leak may occur as the result of an incomplete seal between a mask and a patient's face. In another example leak may occur in a swivel elbow to the ambient.

Patient: A person, whether or not they are suffering from a respiratory condition.

Pressure: Force per unit area. Pressure may be expressed in a range of units, including $cmH_2O$, g-f/cm 2 and hectopascal. 1 $cmH_2O$ is equal to 1 g-f/cm 2 and is approximately 0.98 hectopascal. In this specification, unless otherwise stated, pressure is given in units of $cmH_2O$.

Respiratory Pressure Therapy (RPT): The application of a supply of air to an entrance to the airways at a treatment pressure that is typically positive with respect to atmosphere.

Seal: May be a noun form ("a seal") which refers to a structure, or a verb form ("to seal") which refers to the effect. Two elements may be constructed and/or arranged to 'seal' or to effect 'sealing' therebetween without requiring a separate 'seal' element per se.

5.8.2 Patient Interface

Plenum chamber: a mask plenum chamber will be taken to mean a portion of a patient interface having walls at least partially enclosing a volume of space, the volume having air therein pressurised above atmospheric pressure in use. A shell may form part of the walls of a mask plenum chamber.

Shell: A shell will be taken to mean a curved, relatively thin structure having bending, tensile and compressive stiffness. For example, a curved structural wall of a mask may be a shell. In some forms, a shell may be faceted. In some forms a shell may be airtight. In some forms a shell may not be airtight.

Vent: (noun): A structure that allows a flow of air from an interior of the mask, or conduit, to ambient air for clinically effective washout of exhaled gases. For example, a clinically effective washout may involve a flow rate of about 10 litres per minute to about 100 litres per minute, depending on the mask design and treatment pressure.

5.9 Other Remarks

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

The term "about" is used herein to refer to quantities that vary by as much as 30%, preferably by as much as 20%, and more preferably by as much as 10% to a reference quantity. The use of the word 'about' to qualify a number is merely an express indication that the number is not to be construed as a precise value.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior technology. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Thus, throughout this specification, unless the context requires otherwise, the words "comprise", "comprises" and "comprising" will be understood to imply the inclusion of a stated step or element or group of steps or elements but not the exclusion of any other step or element or group of steps or elements. Any one of the terms: "including" or "which includes" or "that includes" as used herein is also an open term that also means including at least the elements/features that follow the term, but not excluding others. Thus, "including" is synonymous with and means "comprising".

The various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, various inventive concepts may be embodied as a processor readable medium or computer readable storage medium (or multiple such storage media) (e.g., a computer memory, one or more floppy discs, compact discs, optical discs, magnetic tapes, flash memories, circuit configurations in Field Programmable Gate Arrays or other semiconductor devices, or other non-transitory medium or tangible computer storage medium) encoded with one or more programs or processor control instructions that, when executed on one or more computers or other processors, perform methods that implement the various embodiments of the technology discussed above. The computer readable medium or media can be transportable, such that the program or programs stored thereon can be loaded onto one or more different computers or other processors to implement various aspects of the present technology as discussed above.

The terms "program" or "software" are used herein in a generic sense to refer to any type of computer code or set of computer-executable instructions that can be employed to program a computer or other processor to implement various aspects of embodiments as discussed above. Additionally, it should be appreciated that according to one aspect, one or more computer programs that when executed perform methods of the present technology need not reside on a single computer or processor, but may be distributed in a modular fashion amongst a number of different computers or processors to implement various aspects of the present technology. For example, some versions of the present technology may include a server with access to any of the computer readable or processor-readable mediums as described herein. The server may be configured to receive requests for downloading the processor-control instructions or processor-executable instructions of the medium to an electronic device, such as a smart mobile phone or smart speaker, over a network such as a communications network, an internet or the Internet. Thus, the electronic device may also include such a medium to execute the instructions of the medium. Similarly, the present technology may be implemented as a method of a server having access to any of the mediums described herein. The method(s) may include receiving, at the server, a request for downloading the processor-executable instructions of the medium to an electronic device over the network; and transmitting the instructions of the medium to the electronic device in response to the request. Optionally, the server may have access to the medium to execute the instructions of the medium.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

Although the technology herein has been described with reference to particular examples, it is to be understood that these examples are merely illustrative of the principles and applications of the technology. For example, although the acoustic generator(s) and acoustic monitoring techniques are described herein in particular examples concerning the use, and component(s) of, RPT device(s), it will be understood that such acoustic generator(s) and acoustic monitoring techniques may be similarly implemented with the component(s) of any respiratory therapy (RT) device such as a high flow therapy (HFT) device that provides a controlled flow of air at therapeutic flow levels through a patient interface. Thus, the HFT device is similar to a pressure-controlled RPT device but configured with a controller adapted for flow control. In such examples, the acoustic generator(s) may be configured for measuring a gas characteristic associated with the high flow therapy generated by the HFT device and may be integrated to sample the gas flow of a patient circuit, a conduit coupler thereof, and/or a patient interface of the HFT device. Thus, the HFT device may optionally include an acoustic receiver, as well as the processing techniques for acoustic analysis as described herein, for receiving the acoustic/sound signal generated by the acoustic generator implemented HFT device.

In some instances herein, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

| 5.10 REFERENCE SIGNS LIST | |
| --- | --- |
| 1000 | patient |
| 1100 | bed partner |
| 3000 | patient interface |
| 3100 | seal - forming structure |
| 3200 | plenum chamber |
| 3300 | structure |
| 3400 | vent |
| 3600 | connection port |
| 3700 | forehead support |
| 4000 | RPT device |

-continued

5.10 REFERENCE SIGNS LIST

| | |
|---|---|
| 4010 | external housing |
| 4012 | upper portion |
| 4014 | portion |
| 4015 | panel |
| 4016 | chassis |
| 4018 | handle |
| 4020 | pneumatic block |
| 4110 | air filters |
| 4112 | inlet air filter |
| 4114 | outlet air filter |
| 4120 | muffler |
| 4122 | inlet muffler |
| 4124 | outlet muffler |
| 4140 | pressure generator |
| 4142 | blower |
| 4144 | motor |
| 4170 | air circuit |
| 4180 | supplemental oxygen |
| 4270 | transducer(s) |
| 8101 | Microphone sound signal (passive detection) |
| 8102 | Flow generator sound signal (passive detection) |
| 8201 | Scaled patent flow from acoustic signal |
| 8202 | Patient breathing cycle air flow |
| 8301 | Dominant output frequency (example 1) |
| 8302 | Dominant output frequency (example 2) |
| 8303 | Mode hop in dominant output frequency (example 2) |
| 8304 | Dominant frequency of acoustic signal output at 10 cm $H_2O$ |
| 8305 | Dominant frequency of acoustic signal output at 15 cm $H_2O$ |
| 8500 | acoustic generator |
| 8500a | acoustic generator |
| 8500b | acoustic generator |
| 8501 | first end of acoustic generator |
| 8502 | second end of acoustic generator |
| 8510 | windway |
| 8511 | windway inlet |
| 8512 | windway outlet |
| 8515 | windway axis |
| 8520 | vortex outlet |
| 8530 | blade formation |
| 8531 | blade leading edge |
| 8540 | Bore |
| 8541 | Bore outlet |
| 8542 | Horn |
| 8600 | alternate arrangement of an acoustic generator |
| 8602 | second end of acoustic generator |
| 8630 | blade formation |
| 8631 | blade leading edge |
| 8642 | horn |
| 8800 | flow path |
| 8810 | wall boundary |

The invention claimed is:

1. A system for treating a respiratory disorder in a patient, the system comprising a patient interface, a pressure generator configured to generate, for treating the respiratory disorder, a downstream air flow having a flow rate and a pressure, and an air flow path in fluid communication with an air outlet of the pressure generator and an air inlet of the patient interface, the system comprising a sensor for measuring a gas characteristic of a flow of breathable gas being directed to a patient interface for treatment of a respiratory disorder, said sensor comprising:

a first acoustic generator and a second acoustic generator, the first and second acoustic generators separated by a distance along a section of the air flow path to the patient interface, the first and second acoustic generators configured to sample the flow of breathable gas within the air flow path;

wherein the first and second acoustic generators are configured to generate acoustic signals that produce a detectable beat frequency representative of a flow rate or a pressure of the air flow path.

2. The system of claim 1, wherein one acoustic generator of the first and second acoustic generators is located adjacent to or in said patient interface, said one acoustic generator comprising a whistle in fluid communication with said downstream air flow.

3. The system of claim 2, wherein said whistle is adapted to generate an acoustic signal having an acoustic frequency dependent on the flow rate of the downstream air flow delivered to the patient interface, wherein the acoustic signal is inaudible to humans.

4. The system of claim 3, wherein said whistle is adapted to generate an acoustic signal having an acoustic frequency dependent the pressure in the patient interface, wherein the acoustic signal is inaudible to humans.

5. The system of claim 3, wherein said acoustic signal comprises an ultrasonic signal.

6. The system of claim 5, wherein said acoustic signal comprises a dominant acoustic component having a frequency greater than at least 20,000 Hz.

7. The system of claim 5, wherein said acoustic signal comprises a dominant acoustic component having a frequency greater than at least 18,000 Hz.

8. The system of claim 5, wherein said acoustic signal comprises a dominant acoustic component having a frequency greater than at least 17,000 Hz.

9. The system of claim 3, wherein said acoustic signal comprises a frequency that is inaudible to humans.

10. The system of claim 3, wherein said one acoustic generator comprises:

a windway comprising a windway inlet and a windway outlet, the windway inlet adapted to receive, into the windway, a sample portion of said downstream air flow;

a blade formation adjacent said windway outlet and adapted to interact with said sample portion of said downstream air flow to produce a turbulent flow of air;

an acoustic chamber in fluid communication with said windway and comprising a gas flow inlet at a first end of said acoustic chamber and a gas flow outlet at a second end of said acoustic chamber, said acoustic chamber configured to produce a back pressure dependent upon a flow rate of the sample portion of said downstream air flow; and wherein said turbulent flow of air interacts with said back pressure to produce the inaudible acoustic signal.

11. The system of claim 3, wherein another acoustic generator of the first and second acoustic generators is located adjacent said air outlet of said pressure generator and in fluid communication with said downstream air flow.

12. The system of claim 11, wherein said another acoustic generator comprises:

a windway comprising a windway inlet and a windway outlet, the windway inlet adapted to receive, into the windway, a sample portion of said downstream air flow;

a blade formation adjacent said windway outlet and adapted to interact with said sample portion of said downstream air flow to produce a turbulent flow of air;

an acoustic chamber in fluid communication with said windway and comprising a gas flow inlet at a first end of said acoustic chamber and a gas flow outlet at a second end of said acoustic chamber, said acoustic chamber configured to produce a back pressure dependent upon a flow rate of the sample portion of said downstream air flow exiting said air outlet of said pressure generator; and wherein said turbulent flow of air interacts with said back pressure to produce another acoustic signal having an acoustic frequency dependent upon the flow rate or the pressure of the downstream air flow exiting the air outlet of said pressure generator.

13. The system of claim 11, wherein said another acoustic generator and said one acoustic generator are matched such that the inaudible acoustic signal and an another acoustic signal produced by the another acoustic generator have substantially equal acoustic frequencies in response to a given flow rate or pressure of the downstream air flow.

14. The system of claim 13, wherein in use, the acoustic signals generated by said one acoustic generator and said another acoustic generator interact to produce a combined acoustic beat signal representative of a difference in flow rate or pressure between the downstream air flow exiting the air outlet of said pressure generator and the downstream air flow delivered to said patient interface.

15. The system of claim 1, further comprising an acoustic receiver configured to detect acoustic signals generated by the first and second acoustic generators.

16. The system of claim 15, wherein said acoustic receiver further is adapted to detect an acoustic beat frequency formed from interaction of the acoustic signals generated by the first and second acoustic generators.

17. A method for measuring a gas flow rate of a flow of breathable gas directed to a patient interface in a system for treating a respiratory disorder in a patient, the system comprising the patient interface, a pressure generator configured to generate, for treating the respiratory disorder, a downstream air flow having a flow rate and a pressure, and an air flow path in fluid communication with an air outlet of the pressure generator and an air inlet of the patient interface, sampling the flow of breathable gas within the air flow path to the patient interface with first and second acoustic generators, the first and second acoustic generators separated by a distance along a section of the air flow path;

generating, with the first and second acoustic generators, acoustic signals that produce a detectable beat frequency representative of a flow rate or a pressure of the air flow path.

18. The method of claim 17, wherein one acoustic generator of the first and second acoustic generators is located adjacent to or in said patient interface, said one acoustic generator comprising a whistle in fluid communication with said downstream air flow.

19. The method of claim 18, wherein said whistle is adapted to generate an acoustic signal having an acoustic frequency dependent on the flow rate of the downstream air flow delivered to the patient interface, wherein the acoustic signal is inaudible to humans.

20. The method of claim 18, wherein said whistle is adapted to generate an acoustic signal having an acoustic frequency dependent the pressure in the patient interface, wherein the acoustic signal is inaudible to humans.

21. The method of claim 18, wherein said whistle is adapted to generate an acoustic signal comprising an ultrasonic signal, wherein the acoustic signal is inaudible to humans.

\* \* \* \* \*